US012049491B2

(12) United States Patent
Lim et al.

(10) Patent No.: US 12,049,491 B2
(45) **Date of Patent: *Jul. 30, 2024**

(54) MULTIBLOCK COPOLYPEPTIDES OF ELASTIN-BASED POLYPEPTIDES AND MUSSEL FOOT PROTEINS WITH STIMULI-RESPONSIVENESS AND SURFACE-ADHESIVE, METHODS OF PREPARING THEREOF AND USE THEREOF

(71) Applicant: Industry-University Cooperation Foundation Hanyang University Erica Campus, Ansan-si (KR)

(72) Inventors: Dong Woo Lim, Seoul (KR); Jae Hee Lee, Busan (KR); Jae Sang Lee, Ansan-si (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 998 days.

This patent is subject to a terminal disclaimer.

(21) Appl. No.: 16/500,177

(22) PCT Filed: Apr. 5, 2018

(86) PCT No.: PCT/KR2018/004029

§ 371 (c)(1),
(2) Date: Mar. 10, 2020

(87) PCT Pub. No.: WO2018/186702

PCT Pub. Date: Oct. 11, 2018

(65) Prior Publication Data

US 2020/0199199 A1 Jun. 25, 2020

(30) Foreign Application Priority Data

Apr. 5, 2017 (KR) ........................ 10-2017-0044225
Apr. 5, 2018 (KR) ........................ 10-2018-0039787

(51) Int. Cl.

| | |
|---|---|
| ***C07K 14/78*** | (2006.01) |
| ***A61K 9/107*** | (2006.01) |
| ***A61L 24/00*** | (2006.01) |
| ***A61L 24/10*** | (2006.01) |
| ***C07K 14/435*** | (2006.01) |
| *B82Y 5/00* | (2011.01) |

(52) U.S. Cl.

CPC .............. *C07K 14/78* (2013.01); *A61K 9/107* (2013.01); *A61L 24/0031* (2013.01); *A61L 24/108* (2013.01); *C07K 14/43504* (2013.01); *B82Y 5/00* (2013.01)

(58) Field of Classification Search

CPC ................ C07K 14/78; C07K 2319/00; C07K 2317/31; A61F 2250/0067; A61F 2210/0004; A61F 2210/0076; A61F 2/02; G01N 2333/78; B82Y 5/00; B82Y 30/00

See application file for complete search history.

(56) References Cited

U.S. PATENT DOCUMENTS

2004/0171545 A1* 9/2004 Chaikof .................. A61L 31/10 514/16.4
2016/0220727 A1 8/2016 Lu et al.

FOREIGN PATENT DOCUMENTS

| | | | |
|---|---|---|---|
| KR | 10-1722503 B1 | 4/2017 | |
| KR | 10-2017-0113209 A | 10/2017 | |
| WO | WO 2015/116665 A2 | 8/2015 | |
| WO | WO 2015/126480 A1 | 8/2015 | |
| WO | WO2015126480 A2 * | 8/2015 | ........... C97K 14/435 |

OTHER PUBLICATIONS

Kowalczyk et al. Elastin-like polypeptides as a promising family of genetically-engineered protein based polymers. World J Microbiol Biotechnol (2014) 30:2141-2152. (Year: 2014).*

Lee et al. Thermo-Reversible Self-Assembly of Nanoparticles Derived from Elastin-Mimetic Polypeptide. Adv. Mater. 2000, 12, No. 15, Aug. 2, p. 1105-1110. (Year: 2000).*

Kim et al. Physics of Engineered Protein Hydrogels. J. Polym. Sci., Part B: Polym. Phys. 2013, 51, 587-601. (Year: 2013).*

Sever, Mary J. et al., "Metal-Mediated Cross-Linking in the Generation of a Marine-Mussel Adhesive", *Angewandte Chemie International Edition*, vol. 43, Issue 4, 2004, (pp. 448-450).

Lee, Haeshin et al., "Single-molecule mechanics of mussel adhesion", PNAS, vol. 103, No. 35, Aug. 29, 2006 (pp. 12999-13003).

Silverman, Heather G. et al., "Understanding Marine Mussel Adhesion", *Marine Biotechnology*, vol. 9, 2007 (pp. 661-681).

Ito, Yoshiki et al., "Genetically engineered synthesis of artificial proteins incorporated with adhesive functional amino acid residues into repetitive sequence of elastin", *Polymer Preprints*, Japan, vol. 53, No. 2, Mar. 29, 2010 (2 pages in English).

Glassman, Matthew J. et al., "End Block Design Modulates the Assembly and Mechanics of Thermoresponsive, Dual-Associative Protein Hydrogels", *Macromolecules*, 2015 (pp. 1832-1842).

Roberts, Stefan et al., "Elastin-like polypeptides as models of intrinsically disordered proteins", *FEBS letters*, vol. 589, Issue 19, Part A, Sep. 14, 2015 (pp. 2477-2486).

Waite, J. Herbert, "Mussel adhesion-essential footwork." *Journal of Experimental Biology*, vol. 220, Issue 4, 2017 (pp. 517-530).

International Search Report issued on Jul. 13, 2018 in counterpart International Patent Application No. PCT/KR2018/004029 (3 pages in English and 3 pages in Korean).

* cited by examiner

*Primary Examiner* — Aradhana Sasan
*Assistant Examiner* — Jia-Hai Lee
(74) *Attorney, Agent, or Firm* — NSIP Law

(57) ABSTRACT

The present disclosure relates to a multiblock copolypeptide having stimulus responsivity and surface adhesiveness. The multiblock copolypeptide of the present disclosure, which is composed of an elastin-based polypeptide and a mussel foot protein, can form self-assembled core-shell structures and hydrogels exhibiting reversible change in response to temperature stimulation and can be used usefully for biomedical applications due to remarkably superior surface adhesiveness.

19 Claims, 11 Drawing Sheets

Specification includes a Sequence Listing.

【FIG. 1】
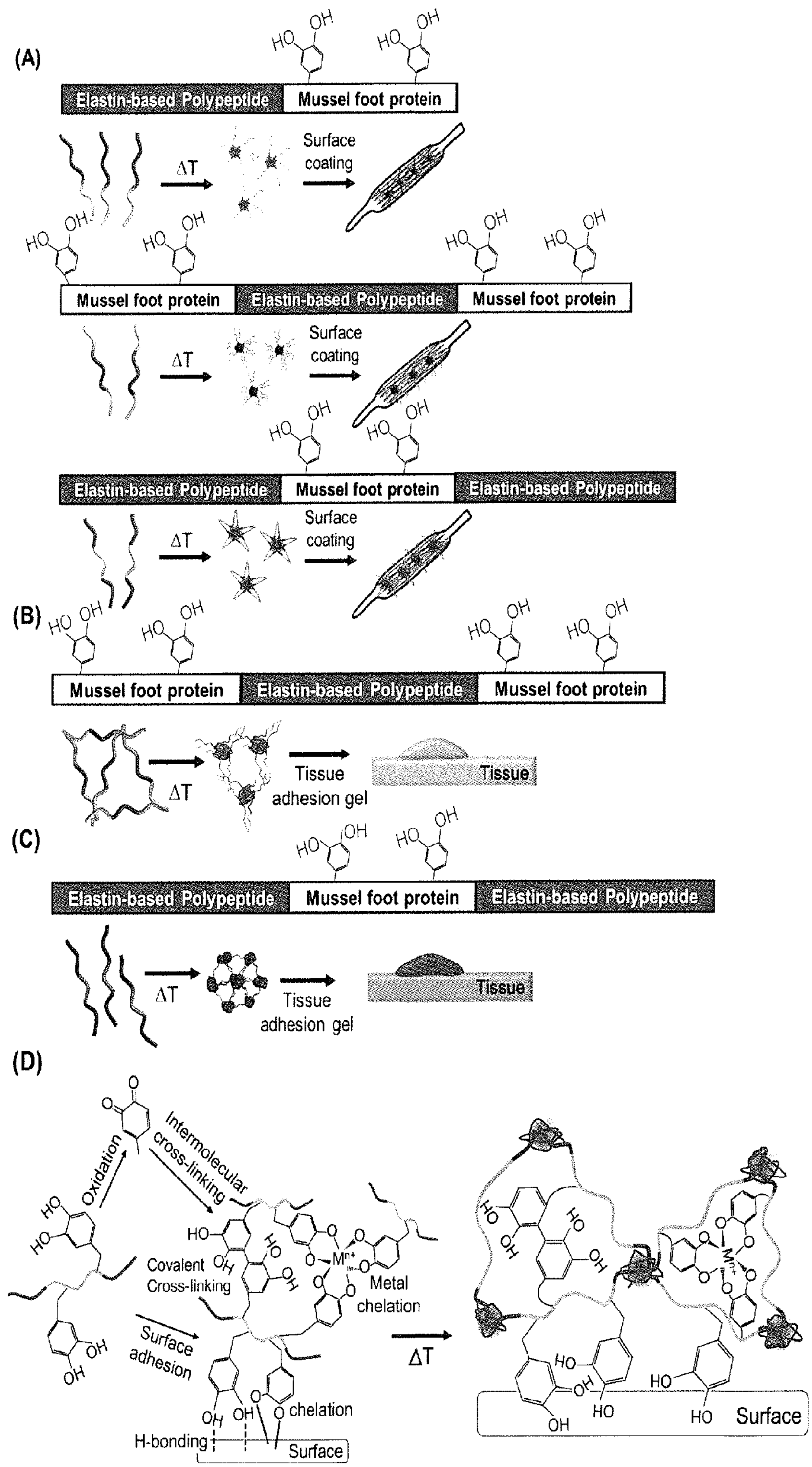

【FIG. 2】
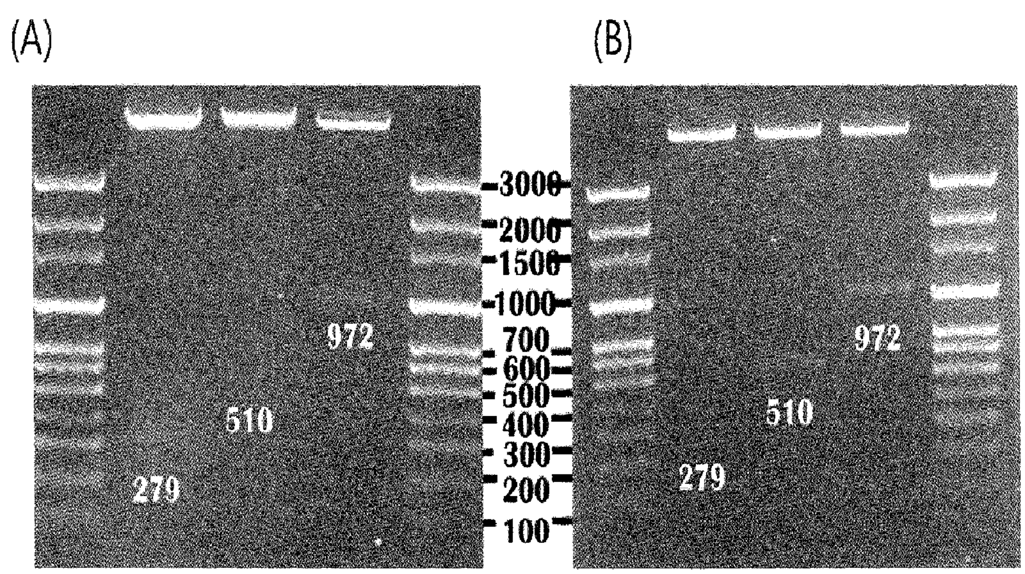

【FIG. 3】
(A)
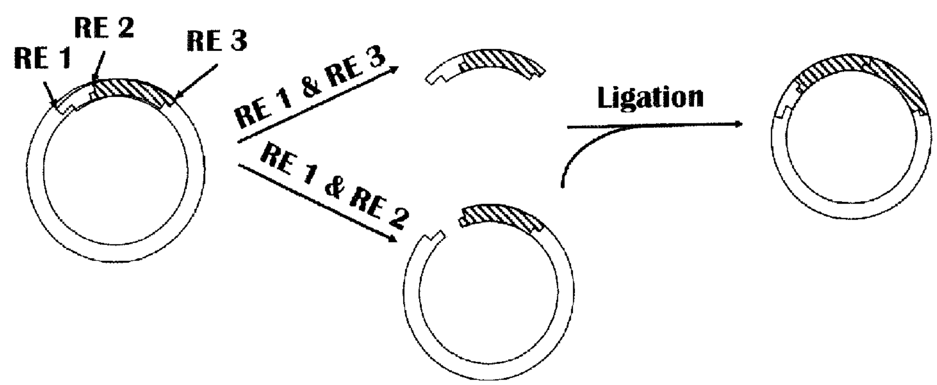
(B)
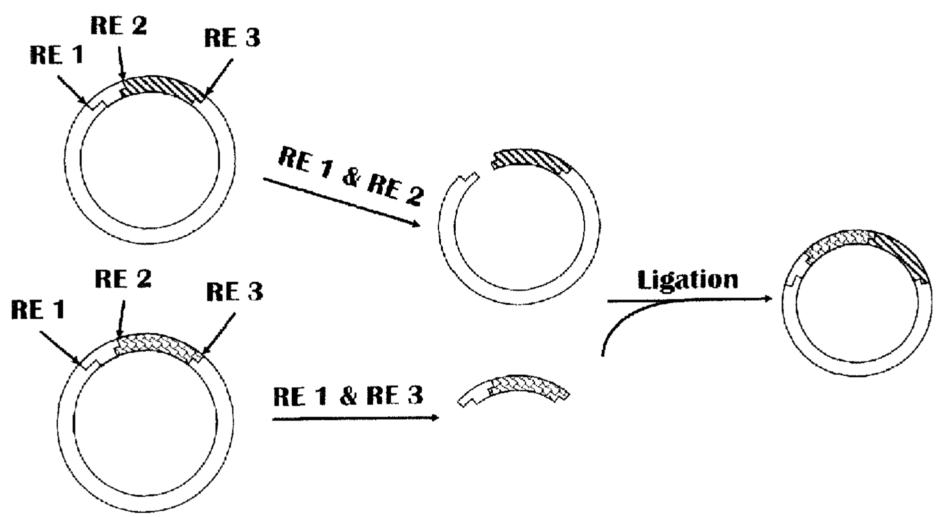

【FIG. 4】
(A)
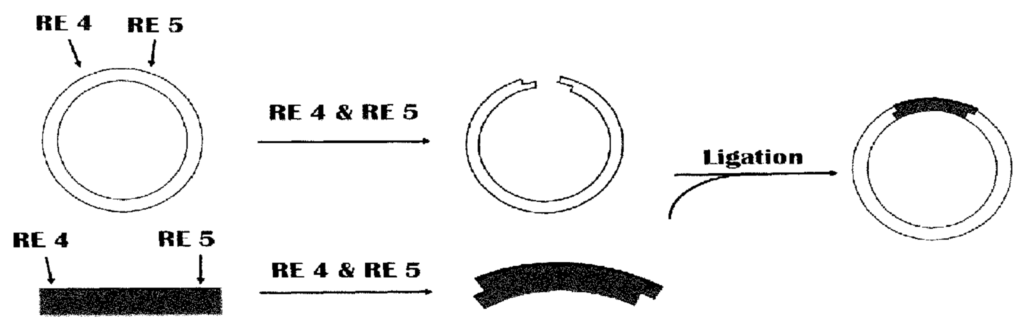
(B)
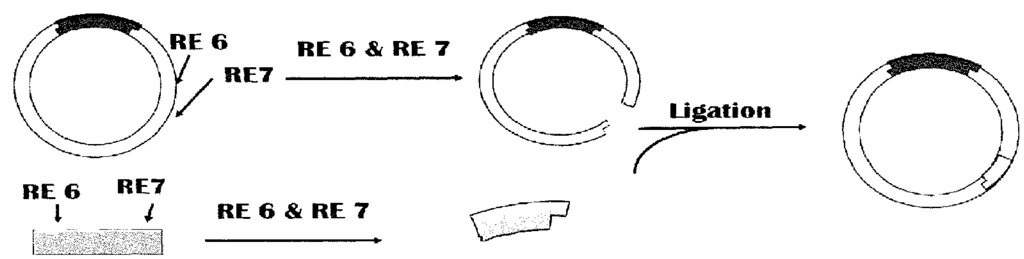

【FIG. 5】
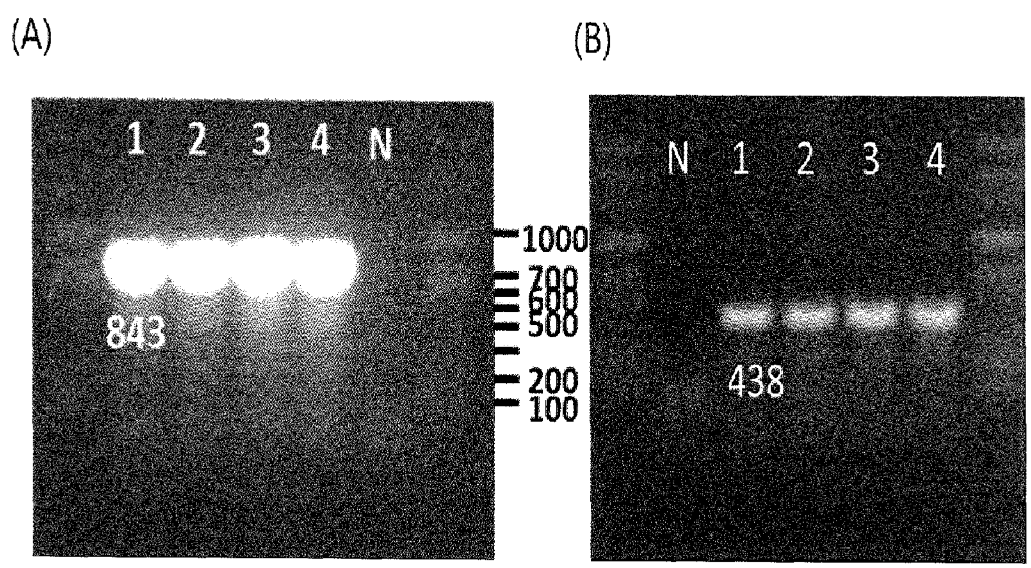

【FIG. 6】
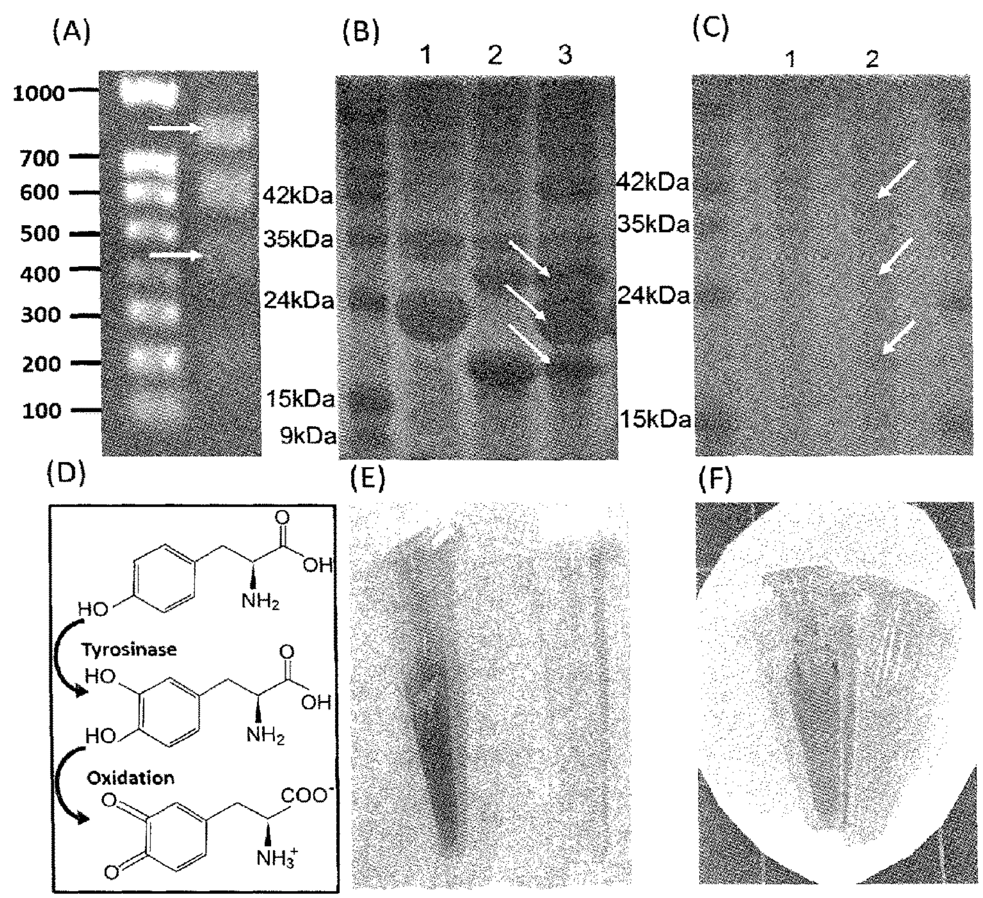
【FIG. 7】
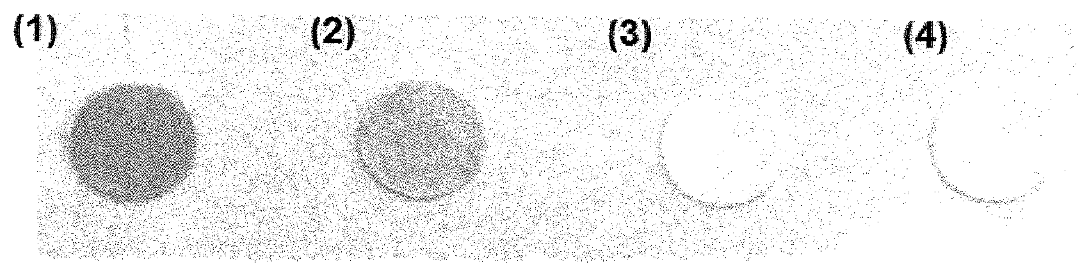

【FIG. 8】
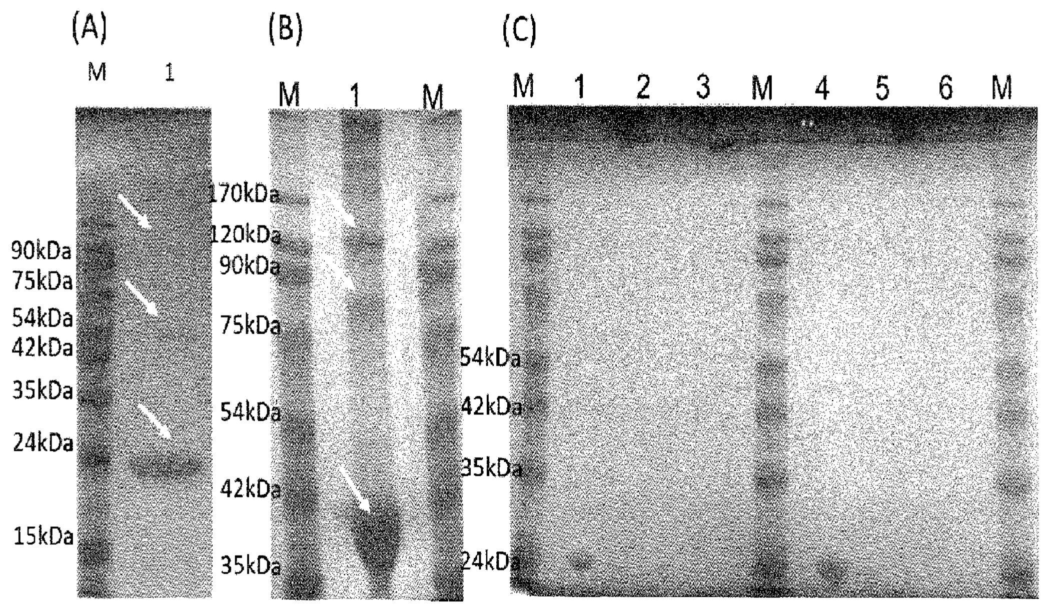
【FIG. 9】
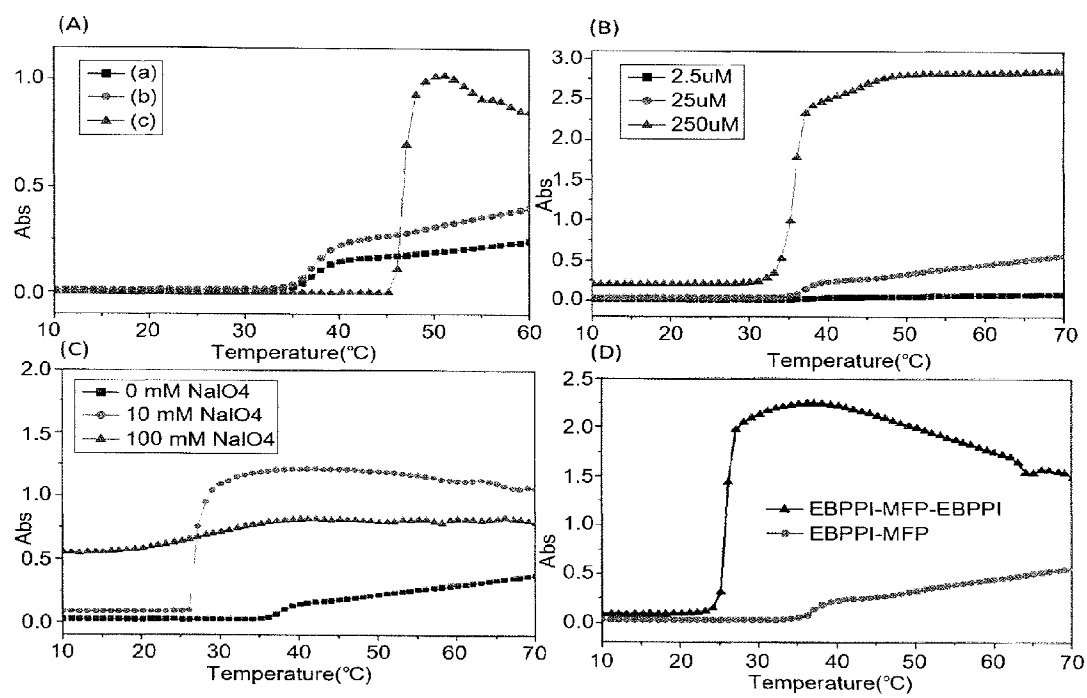

【FIG. 10】
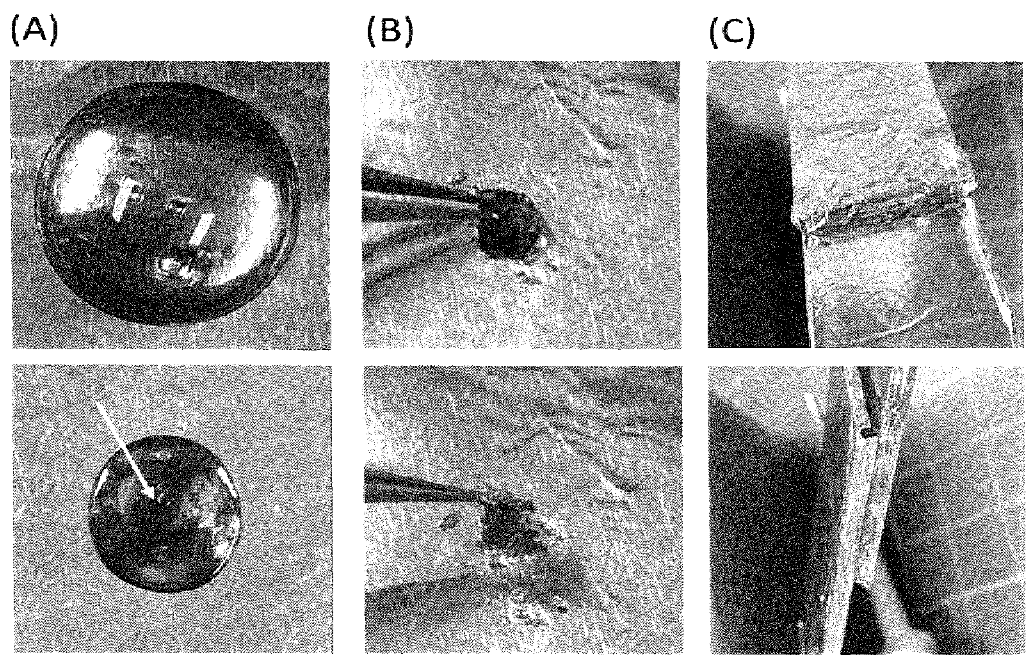

【FIG. 11】
(A)
(B)
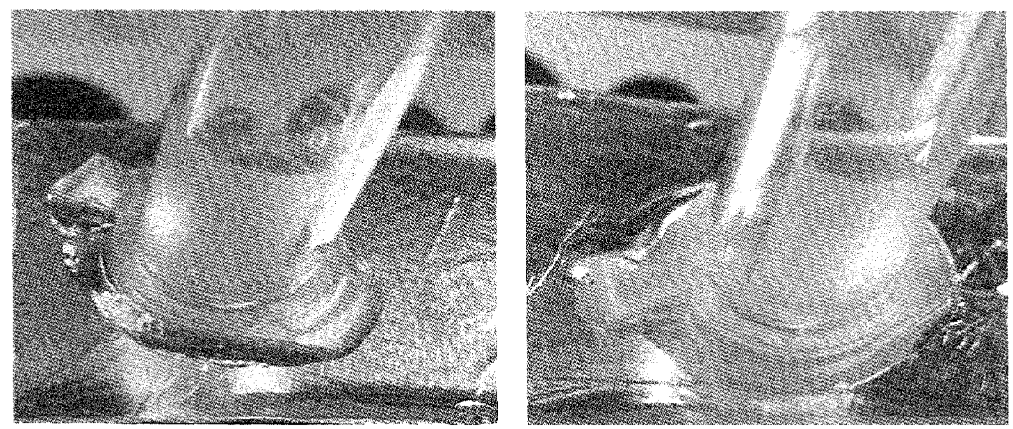

【FIG. 12】
(A)
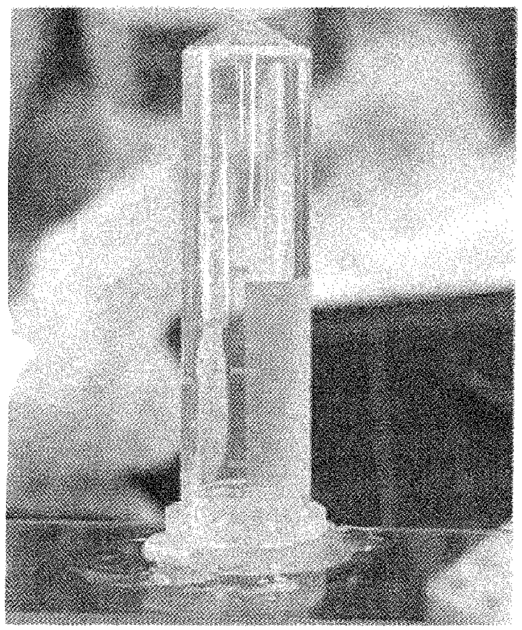
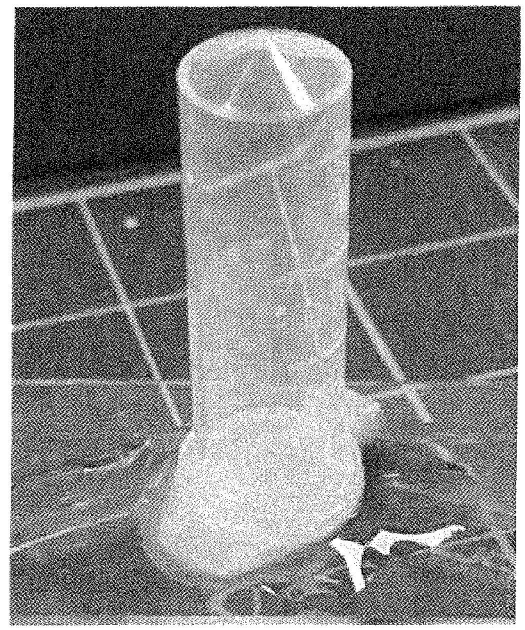
(B)
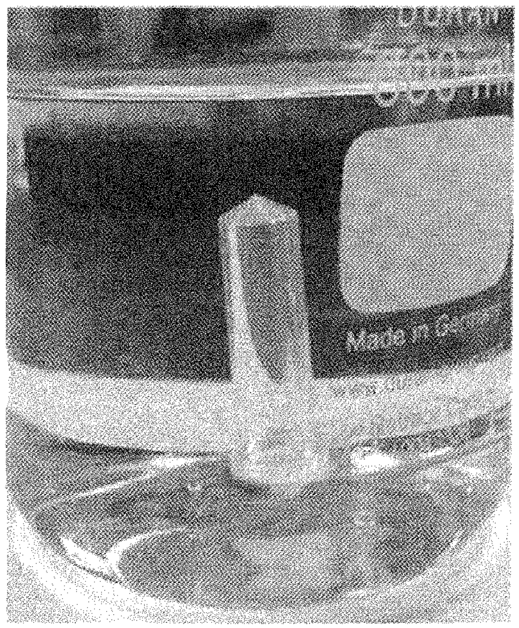
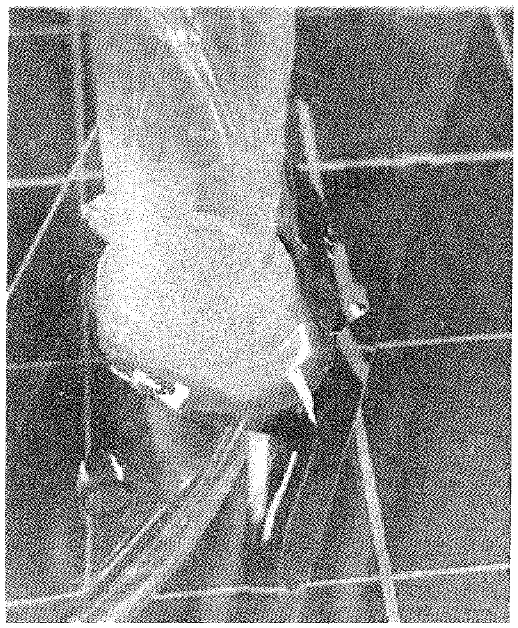

【FIG. 13】
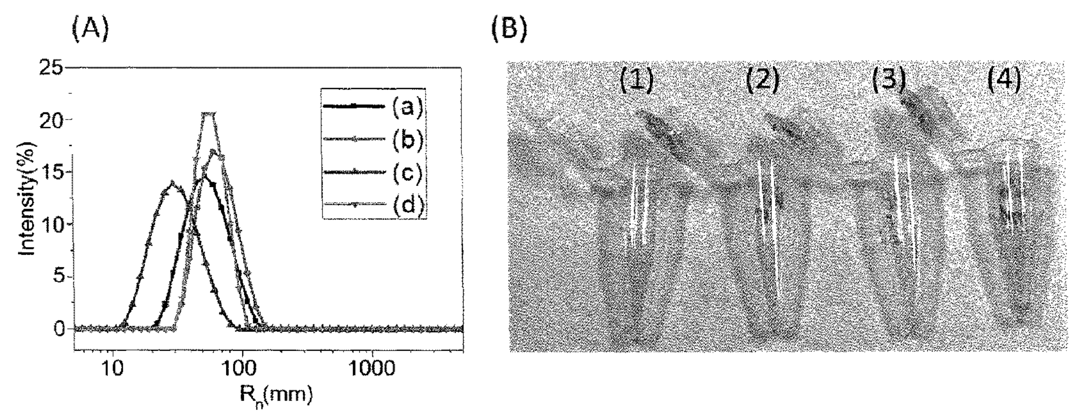
【FIG. 14】
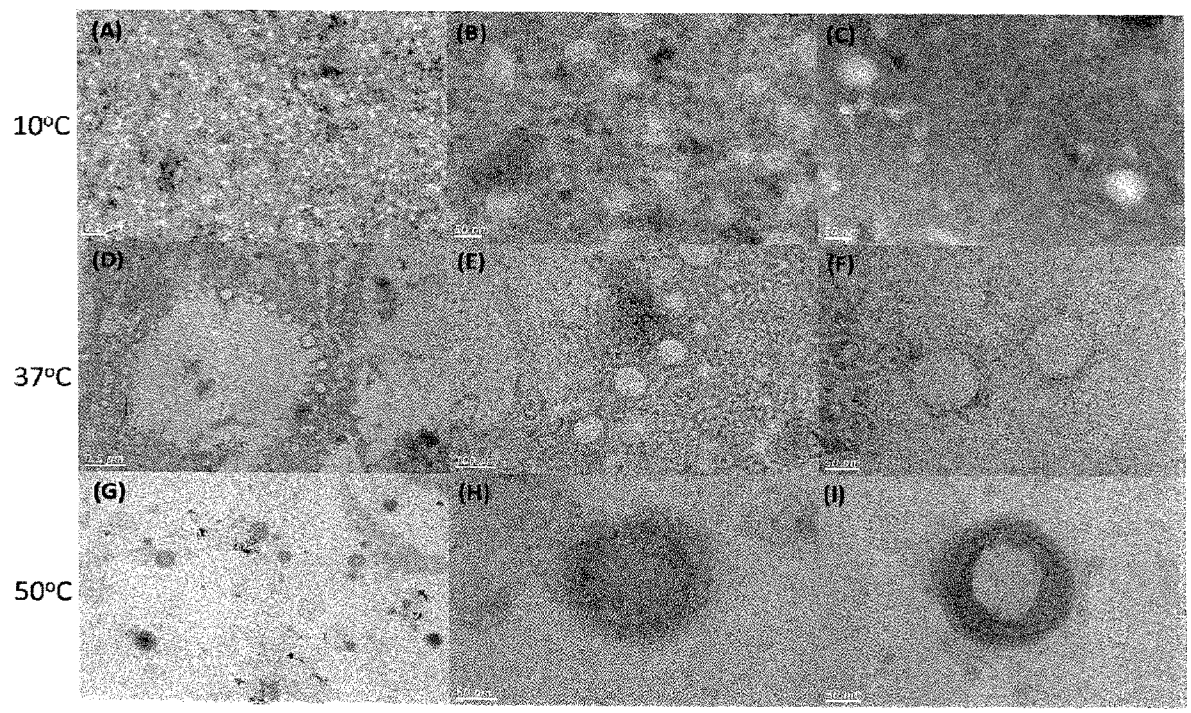

MULTIBLOCK COPOLYPEPTIDES OF ELASTIN-BASED POLYPEPTIDES AND MUSSEL FOOT PROTEINS WITH STIMULI-RESPONSIVENESS AND SURFACE-ADHESIVE, METHODS OF PREPARING THEREOF AND USE THEREOF

CROSS REFERENCE TO RELATED APPLICATIONS

This application is a U.S. National Stage Application of International Application No. PCT/KR2018/004029, filed on Apr. 5, 2018, which claims the benefit under 35 USC 119(a) and 365(b) of Korean Patent Application No. 10-2017-0044225, filed on Apr. 5, 2017, and Korean Patent Application No. 10-2018-0039787, filed on Apr. 5, 2018 in the Korean Intellectual Property Office, the entire disclosure of which is incorporated herein by reference for all purposes.

TECHNICAL FIELD

The present disclosure relates to a multiblock copolypeptide having stimulus responsivity and surface adhesiveness, more particularly to a multiblock copolypeptide composed of an elastin-based polypeptide and a mussel foot protein, a method for preparing the multiblock copolypeptide, a self-assembled nanostructure of a core-shell structure including the multiblock copolypeptide, and a hydrogel including the multiblock copolypeptide.

BACKGROUND ART

Self-assembly of protein-based copolymer blocks having responsivity to change in environment such as temperature, pH and ionic strength to micelle or hydrogel structures has been studied for decades due to their high biocompatibility and controllable resolution. Protein-based polypeptide blocks self-assembled to core-shell micelles have attracted considerable interests as a drug delivery system. In particular, triblock polypeptides have been studied for tissue engineering applications because sol-gel transition occurs due to physical or chemical crosslinking. Besides, various protein-based materials have been developed for drug delivery and tissue engineering applications.

Bioadhesives refer to materials having adhesive properties to various biomaterials such as cell membranes, cell walls, lipids, proteins, DNAs, growth factors, cells, tissues, etc. They are applicable to various biomedical applications such as tissue adhesives or hemostatics, scaffolds for tissue engineering, drug delivery carriers, tissue fillers, wound healing, prevention of intestinal adhesion, etc. Strong adhesion and crosslinking abilities are required for the bioadhesives and their function should be maintained for a long period of time in vivo. The currently commercially available or practically used bioadhesives include cyanoacrylate instant glues, fibrin glue, gelatin glue, polyurethane-based adhesives, etc. However, bioadhesives using synthetic polymers are very weak in the aqueous environment in vivo, and cyanoacrylate-based bioadhesives have side effects such as immune response, etc. In addition, fibrin-based bioadhesives actually used for patients at present are limited due to very low adhesion ability despite the lack of side effects. Gelatin tissue adhesives have the problem of tissue toxicity due to crosslinking reactions between formalin or glutaraldehyde used as a crosslinking agent and proteins. Polyurethane-based tissue adhesives have the problem of biological toxicity of aromatic diisocyanates used for synthesis.

Mussel can inhabit various underwater surfaces of harsh environments due to its foot protein. The dihydroxyphenylalanine (DOPA) of the mussel foot protein (MFP) plays an important role in surface adhesion. The mussel foot protein is into six types from type 1 to type 6. Each MFP has DOPA residues with different contents and thus exhibits different surface adhesiveness. For example, MFPs 1, 2 and 4 show intramolecular and intermolecular crosslinking, whereas MFPs 3, 5 and 6 exhibit surface adhesiveness through interaction between inorganic and organic molecules. Accordingly, DOPA plays an important chemical contribution to adhesiveness through intramolecular and intermolecular crosslinking (Silverman H. G. et al., *Marine Biotechnology,* 9(6), 661-681, 2007; Lee Haeshin. et al., *Proceedings of the National Academy of Sciences,* 103 (35), 12999-13003, 2006). DOPA having a catechol side chain with a tyrosine residue hydroxylated by tyrosinase can bind to metal ions, oxides and semimetals through coordination or hydrogen bonding (Sever, M. J. et al., *Angewandte Chemie,* 116(4), 454-456, 2004).

Recently, although it was reported that a block polypeptide composed of an elastin-based polypeptide and a resilin-like polypeptide exhibits phase transition behavior and can be self-assembled, its surface adhesiveness was not disclosed (Korean Patent Publication No. 10-2017-0113209).

The inventors of the present disclosure have made consistent efforts to find polypeptides having stimulus responsivity and surface adhesiveness that can be used in biomedical applications. As a result, they have identified that a multiblock copolypeptide composed of an elastin-based polypeptide (EBP) and a mussel foot protein (MFP) may be used to form self-assembled core-shell structures and hydrogels exhibiting reversible change in response to temperature stimulation and exhibiting remarkably superior surface adhesiveness, and have completed the present disclosure.

DISCLOSURE

Technical Problem

The present disclosure is directed to providing a multiblock copolypeptide having stimulus responsivity and surface adhesiveness.

The present disclosure is also directed to providing a gene encoding the multiblock copolypeptide, a recombinant vector including the gene, a recombinant microorganism with the gene or the recombinant vector introduced, and a method for preparing a multiblock copolypeptide using the recombinant microorganism.

The present disclosure is also directed to providing a self-assembled nanostructure of a core-shell structure, wherein an EBP block of the multiblock copolypeptide forms a core structure and an MFP block forms a shell structure in response to temperature stimulation, and a drug delivery composition containing the self-assembled nanostructure.

The present disclosure is also directed to providing a hydrogel formed from crosslinking of block polypeptides of the multiblock copolypeptide in response to temperature stimulation, a bioadhesive composition containing the hydrogel, and a surgical suture containing the hydrogel.

Technical Solution

The present disclosure provides a multiblock copolypeptide composed of an elastin-based polypeptide (EBP) and a mussel foot protein (MFP).

The present disclosure also provides a gene encoding the multiblock copolypeptide, a recombinant vector including the gene, and a recombinant microorganism with the gene or the recombinant vector introduced.

The present disclosure also provides a method for preparing a multiblock copolypeptide, which includes: (a) a step of producing a multiblock copolypeptide by culturing the recombinant microorganism; and (b) a step of obtaining the produced multiblock copolypeptide.

The present disclosure also provides a self-assembled nanostructure of a core-shell structure wherein an EBP block of the multiblock copolypeptide forms a core structure and an MFP block forms a shell structure in response to temperature stimulation, and a drug delivery composition containing the self-assembled nanostructure.

The present disclosure also provides a hydrogel prepared through crosslinking between block polypeptides of the multiblock copolypeptide in response to temperature stimulation.

The present disclosure also provides a bioadhesive composition and a surgical suture containing the hydrogel.

Advantageous Effects

A multiblock copolypeptide of the present disclosure forms self-assembled core-shell structures and hydrogels exhibiting reversible change in response to temperature stimulation. Because it exhibits remarkably superior surface adhesiveness, it can be used usefully for biomedical applications.

BRIEF DESCRIPTION OF DRAWINGS

FIG. 1 schematically shows various block copolypeptides composed of EBP and MFP ((A): diblock and triblock copolypeptides forming a core-shell (micelle) structure, (B): MFP-EBP-MFP triblock copolypeptide forming a hydrogel, (C): EBP-MFP-EBP triblock copolypeptide forming a hydrogel, (D): stimulus responsivity and surface adhesiveness mechanisms of an EBP-MFP-EBP triblock copolypeptide).

FIG. 2 shows a result of investigating MFP DNA of the present disclosure by agarose gel electrophoresis ((A): Mcfp5, (B) Mgfp5, lane (M): size marker, lane (1): one MFP repeat unit, lane (2): two MFP repeat units, lane (3): four MFP repeat units).

FIG. 3 schematically shows cloning of an EBP-MFP block copolypeptide gene of the present disclosure ((A): multiple cloning of MFP, (B): EBP-MFP block copolypeptide cloning).

FIG. 4 schematically shows cloning of tyrosinase and ORF438 genes of the present disclosure ((A): tyrosinase cloning, (B): ORF438 cloning).

FIG. 5 shows a result of investigating (A) tyrosinase and (B) ORF438 DNA of the present disclosure by agarose gel electrophoresis (lanes (1) and (2) DNA template: 25 ng, lanes (3) and (4) DNA template: 50 ng, lane (N): negative control group).

FIG. 6 shows (A) a agarose gel electrophoresis (1.2%) result of tyrosinase gene (824 bp) and ORF438 gene (438 bp) DNAs; (B) an SDS-PAGE result of tyrosinase (~35 kDa), EBP-MFP diblock copolypeptide (~24 kDa) and ORF438 (~15 kDa) coexpressed in *E. coli* (lane (1): EBP-MFP diblock copolypeptide, lane (2): tyrosinase and ORF438, lane (3): diblock copolypeptide, tyrosinase and ORF438 coexpressed in *E. coli*); (C) an SDS-PAGE result of EBP-MFP-EBP triblock copolypeptide (~41 kDa), tyrosinase (~35 kDa) and ORF438 (~15 kDa) coexpressed in *E. coli* (lane (1): EBP-MFP-EBP triblock copolypeptide, lane (2): triblock copolypeptide, tyrosinase and ORF438 coexpressed in *E. coli*); (D) schematic chemical mechanism of tyrosine modification of EBP-MFP block copolypeptide; (E) a result of confirming hydroxylation of EBPPI$[G_1A_4F_1]_6$-MFP$[Mgfp5]_1$ diblock copolypeptide through a coexpression system of tyrosinase, ORF438 and diblock copolypeptide in *E. coli* by NBT staining; and (F) a result of confirming hydroxylation of EBPPI$[G_1A_4F_1]_6$-MFP$[Mgfp5]_1$-EBPPI$[G_1A_4F1]_6$ triblock copolypeptide in *E. coli* through a coexpression system of tyrosinase, ORF438 and triblock copolypeptide by NBT staining.

FIG. 7 shows a result of investigating the tyrosine residue modification of a diblock copolypeptide of the present disclosure by treating with mushroom-derived tyrosinase and then staining with NBT/glycinate ((1) dopamine hydrochloride as a positive control group, (2) EBPPI$[G_1A_4F_1]_6$-MFP$[Mgfp5]_1$ treated with mushroom-derived tyrosinase, (3) unmodified EBPPI$[G_1A_4F_1]_6$-MFP$[Mgfp5]_1$ as a negative control group, (4) EBPPI$[G_1A_4F_1]_6$).

FIG. 8 shows an SDS-PAGE of a copper-stained block copolypeptide of the present disclosure ((A): EBPPI$[G_1A_4F_1]_6$-MFP$[Mgfp5]_1$ diblock copolypeptide treated with mushroom-derived tyrosinase, (B): EBPPI$[G_1A_4F_1]_6$-MFP$[Mgfp5]_1$-EBPPI$[G_1A_4F_1]_6$ triblock copolypeptide treated with mushroom-derived tyrosinase, (C): EBPPI$[G_1A_4F_1]_6$-MFP$[Mgfp5]_1$ diblock copolypeptide treated with $NaIO_4$ of various concentrations; lane (M): standard protein marker, lane (1): EBPPI$[G_1A_4F_1]_6$-MFP$[Mgfp5]_1$, lane (2): EBPPI$[G_1A_4F_1]_6$-MFP$[Mgfp5]_1$ treated with 5 mM $NaIO_4$, lane (3): EBPPI$[G_1A_4F_1]_6$-MFP$[Mgfp5]_1$ treated with 50 mM $NaIO_4$, lane (4): hydroxylated EBPPI$[G_1A_4F_1]_6$-MFP$[Mgfp5]_1$, lane (5): hydroxylated EBPPI$[G_1A_4F_1]_6$-MFP$[Mgfp5]_1$ treated with 5 mM $NaIO_4$, lane (6): hydroxylated EBPPI$[G_1A_4F_1]_6$-MFP$[Mgfp5]_1$ treated with 50 mM $NaIO_4$; The diblock and triblock copolypeptides were treated with mushroom-derived tyrosinase to modify the tyrosine residue.).

FIG. 9 shows a result of thermal profiling under different conditions ((A) (a): EBPPI$[G_1A_4F_1]_6$-MFP$[Mgfp5]_1$ diblock copolypeptide treated with mushroom-derived tyrosinase, (b): unmodified EBPPI$[G_1A_4F_1]_6$-MFP$[Mgfp5]_1$ diblock copolypeptide (c): monoblock EBPPI$[G_1A_4F_1]_6$ as a control group; (B) EBPPI$[G_1A_4F_1]_6$-MFP$[Mgfp5]_1$ treated with mushroom-derived tyrosinase depending on the concentration of the diblock copolypeptide; (C) EBPPI$[G_1A_4F_1]_6$-MFP$[Mgfp5]_1$ treated with mushroom-derived tyrosinase depending on the concentration of $NaIO_4$; (D) EBPPI$[G_1A_4F_1]_6$-MFP$[Mgfp5]_1$ diblock treated with 25 μM mushroom-derived tyrosinase and EBPPI$[G_1A_4F_1]_6$-MFP$[Mgfp5]_1$-EBPPI$[G_1A_4F_1]_6$ triblock copolypeptide treated with mushroom-derived tyrosinase).

FIG. 10 shows (A) photographs of mushroom-derived tyrosinase-catalyzed EBPPI$[G_1A_4F_1]_6$-MFP$[Mgfp5]_1$ diblock copolypeptide treated with $NaIO_4$ of different concentrations (10-100 mM); (B) photographs of 30 wt % diblock copolypeptide treated with 100 mM $NaIO_4$; and (C) photographs of 40 wt % diblock copolypeptide treated with 10 mM $NaIO_4$.

FIG. 11 shows (A) photographs of mushroom-derived tyrosinase-catalyzed EBPPI$[G_1A_4F_1]_6$-MFP$[Mgfp5]_1$-EBPPI$[G_1A_4F_1]_6$ triblock copolypeptide (10 wt %) treated with 10 mM $NaIO_4$; and (B) a photograph of mushroom-derived tyrosinase-catalyzed EBPPI$[G_1A_4F_1]_6$-MFP$[Mgfp5]_1$-EBPPI$[G_1A_4F_1]_6$ triblock copolypeptide adhered onto a surface under the condition of (A) (left) and a photograph of 20 wt % EBP triblock copolypeptide treated under the condition of (A) as a control group (right).

FIG. 12 shows (A) photographs of a hydroxylated block copolypeptide (10 wt %) treated with 10 mM $NaIO_4$ in a coexpression system; and (B) photographs of testing adhesiveness of a hydroxylated block copolypeptide in a coexpression system in the presence of water.

FIG. 13 shows (A) a result of measuring the hydrodynamic radius of mushroom-derived tyrosinase-catalyzed, hydroxylated or unmodified block copolypeptide by DLS (The hydrodynamic radius of the block copolypeptide was measured at 12.5 μM in a 10 mM phosphate buffer (pH 5). The hydrodynamic radius of the block copolypeptide above the phase transition is 50-70 nm, which suggests that the block copolypeptide exists as a specific structure. (a): unmodified EBPPI$[G_1A_4F_1]_6$-MFP$[Mgfp5]_1$ diblock copolypeptide at 10° C., (b): unmodified EBPPI$[G_1A_4F_1]_6$-MFP$[Mgfp5]_1$ diblock copolypeptide at 45° C., (c): EBPPI$[G_1A_4F_1]_6$-MFP$[Mgfp5]_1$ diblock copolypeptide treated with mushroom-derived tyrosinase at 10° C., (d): EBPPI$[G_1A_4F_1]_6$-MFP$[Mgfp5]_1$ diblock copolypeptide treated with mushroom-derived tyrosinase at 45° C.); and (B) a result of confirming the surface adhesiveness of a hydroxylated EBPPI$[G_1A_4F_1]_6$-MFP$[Mgfp5]_1$ diblock copolypeptide in a coexpression system using a fluorescent dye ((1) nonspecific reaction between tube surface and fluorescent dye, (2) surface adhesiveness of EBP diblock copolypeptide and fluorescent dye, (3) surface adhesiveness of hydroxylated EBPPI$[G_1A_4F_1]_6$-MFP$[Mgfp5]_1$ diblock copolypeptide below transition temperature, (4) surface adhesiveness of hydroxylated EBPPI$[G_1A_4F_1]_6$-MFP$[Mgfp5]_1$ diblock copolypeptide above transition temperature).

FIG. 14 shows transmission electron microscopic images of mushroom-derived tyrosinase-catalyzed, hydroxylated EBPPI$[G_1A_4F_1]_6$-MFP$[Mgfp5]_1$ diblock copolypeptide depending on temperature ((A, B, C) The EBPPI$[G_1A_4F_1]_6$-MFP$[Mgfp5]_1$ diblock copolypeptide nanostructure observed at 10° C. has scales of 0.2 μm, 50 nm and 50 nm, respectively. (D, E, F) The EBPPI$[G_1A_4F_1]_6$-MFP$[Mgfp5]_1$ diblock copolypeptide structure observed at 37° C. has scales of 0.5 mm, 100 nm and 50 nm, respectively. (G, H, I) The EBPPI$[G_1A_4F_1]_6$-MFP$[Mgfp5]_1$ diblock copolypeptide structure observed at 50° C. has scales of 0.5 μm, 100 nm and 50 nm, respectively.).

BEST MODE

In the present disclosure, it was confirmed that a multiblock copolypeptide composed of an elastin-based polypeptide (EBP) and a mussel foot protein (MFP) forms self-assembled core-shell structures and hydrogels exhibiting reversible change in response to temperature stimulation and exhibiting remarkably superior surface adhesiveness.

Accordingly, in an aspect, the present disclosure relates to a multiblock copolypeptide composed of an elastin-based polypeptide (EBP) and a mussel foot protein (MFP).

In the present disclosure, the term "copolypeptide" refers to a polypeptide which is a copolymer.

In the present disclosure, the term "polypeptide" refers to any polymer chain of amino acids. The terms "peptide" and "protein" may be used interchangeably with the term polypeptide and also refer to a polymer chain of amino acids. The term "polypeptide" includes natural or synthetic proteins, protein fragments and polypeptide analogues of protein sequences. The polypeptide may be a monomer or a polymer.

The term "phase transition" refers to change in the state of matter, e.g., change from water to water vapor or from ice to water.

Basically, the polypeptide having such a phase transition behavior according to the present disclosure is a stimulus responsivity elastin-based polypeptide (EBP). The "elastin-based polypeptide" is also called an "elastin-like polypeptide (ELP)". They are the terms widely used in the related art.

The EBP undergoes reversible phase transition at a transition temperature ($T_t$), also called a lower critical solution temperature (LOST). It is highly soluble below $T_t$ but becomes insoluble above $T_t$.

In the present disclosure, the physical and chemical properties of EBP are regulated by a combination of the pentapeptide repeat unit Val-Pro-(Gly or Ala)-$X_{aa}$-Gly [VP(G or A)XG]. Specifically, the third amino acid of the repeat unit determines relative mechanical properties. For examples, in the present disclosure, the third amino acid Gly determines elasticity and Ala determines plasticity. The elasticity or plasticity is the property occurring after the transition.

Meanwhile, both the hydrophobicity of the guest residue $X_{aa}$, which is the fourth amino acid, and the multimerization of the pentapeptide repeat unit affect the $T_t$.

The mussel foot protein of the present disclosure may be adhered to various surfaces through DOPA. The DOPA having a catechol side chain provides surface adhesivity through hydrogen bonding or coordination with surface molecules, and the quinone, which is an oxidized form of the DOPA, exhibits cohesive force through intermolecular crosslinking. Although the quinone cannot interact with surface molecules because it is an oxidized form of the DOPA, it provides powerful cohesive force in water by forming intramolecular and intermolecular crosslinkages through aryl-aryl coupling, metal chelation, and Michael-type addition reaction with amine-containing proteins. The crosslinkages formed by the quinone result in a hardened sheath and exhibit moisture resistance. Therefore, DOPA and quinone are essential factors in surface adhesion, which is determined depending on pH condition. When mussel secretes MFP for surface adhesion, the pH around the mussel foot is below 3.0, and the oxidation of DOPA is restricted for adsorption of surface oxides through hydrogen bonding and metal ion coordination. After surface adhesion, the MFP is exposed to seawater (pH ~8.3). As a result, the DOPA is induced to be oxidized to quinone, and crosslinking and protein coagulation occur. In addition, the hydrophilic amino acids of MFP such as Ser and Gly participate in cohesive interactions through hydrogen bonding, cation-pi interaction or electrostatic and hydrophobic interaction (Waite, J. H., *Journal of Experimental Biology,* 220(4), 517-530, 2017).

In the present disclosure, a new type of multifunctional block copolypeptide composed of an EBP block and an MFP block is designed, synthesized and characterized reasonably. Based on the surface adhesiveness of naturally occurring MFP, the present disclosure aims at combining the MFP with the EBP block, which is a stimulus-responsive protein, for biomimetic adhesion in water, formation of self-assembled structures and application to biomedicine. In order to achieve strong interfacial underwater adhesiveness, the gene sequences of California mussel foot protein 5 (*Mytilus californianus* foot protein 5 (Mcfp5)) and Mediterranean mussel foot protein 5 (*Mytilus galloprovincialis* foot protein 5 (Mgfp5)), which exhibit the highest tyrosine content (~30%) from among all mussel foot proteins, were selected. The tyrosine content of MFP is related with the efficiency and strength of surface adhesion (Silverman H. G. et al., *Marine Biotechnology,* 9(6), 661-681, 2007).

In the present disclosure, the multiblock copolypeptide may be composed of an arrangement selected from a group consisting of $(EBP)_n(MFP)_n$, $(EBP)_n(MFP)_n(EBP)_n$ and $(MFP)_n(EBP)_n(MFP)_n$, wherein the n, which is an integer 1 or greater, is the number of EBP or MFP repeat unit.

In the present disclosure, the elastin-based polypeptide (EBP) may be composed of an amino acid sequence selected from a group consisting of a [VPGXG VPGXG VPGXG VPGXG VPGXG VPGXG] block, a [VPAXG VPAXG VPAXG VPAXG VPAXG VPAXG] block and an [IPAXG IPAXG IPAXG IPAXG IPAXG IPAXG] block, wherein the X is an amino acid excluding proline.

In the present disclosure, the X (or $X_{aa}$) is referred to as a "guest residue". EBPs of various types according to the present disclosure can be prepared by introducing different $X_{aa}$'s.

The polypeptide may have multi-stimuli responsivity.

The term "multi-stimuli responsivity" means responsivity to more than one stimulus. Specifically, the stimulus may be one or more selected from a group consisting of temperature, pH, ionic strength and a ligand.

In the present disclosure, the ligand refers to a substance binding specifically to a certain target substance, for example, an antibody, an antigen, an enzyme, a substrate, a receptor, a peptide, a DNA, an RNA, an aptamer, protein A, protein G, avidin, biotin, a chelate compound, a metal ion (e.g., calcium ion, etc.), etc.

In the present disclosure, the [VPGXG VPGXG VPGXG VPGXG VPGXG VPGXG] block is represented by the amino acid sequence of SEQ ID NO 1, the [VPAXG VPAXG VPAXG VPAXG VPAXG VPAXG] block is represented by the amino acid sequence of SEQ ID NO 2, and the [IPAXG IPAXG IPAXG IPAXG IPAXG IPAXG] block is represented by the amino acid sequence of SEQ ID NO 3.

In the present disclosure, the term "amino acid" means a natural amino acid or an artificial amino acid, specifically a natural amino acid. For example, the amino acid may be glycine, alanine, serine, valine, leucine, isoleucine, methionine, glutamine, asparagine, cysteine, histidine, phenylalanine, arginine, tyrosine, tryptophan, etc.

The properties of these amino acids are well known in the art. Specifically, they exhibit hydrophilic (negatively charged or positively charged) or hydrophobic properties, and exhibit aliphatic or aromatic properties.

The abbreviations such as Gly (G), Ala (A), etc. used in the present disclosure are abbreviations of amino acids. The abbreviations of amino acids include glycine (Gly, G), alanine (Ala, A), valine (Val, V), leucine (Leu, L), isoleucine (Ile, I), proline (Pro, P), phenylalanine (Phe, F), tyrosine (Tyr, Y), tryptophan (Trp, W), cysteine (Cys, C), methionine (Met, M), serine (Ser, S), threonine (Thr, T), lysine (Lys, K), arginine (Arg, R), histidine (His, H), aspartic acid (Asp, D), glutamic acid (Glu, E), asparagine (Asn, N) and glutamine (Gln, Q). These abbreviations are widely used in the art.

In the present disclosure, a "hydrophilic amino acid" refers to an amino acid exhibiting hydrophilic property and includes lysine, arginine, etc., and a "hydrophobic amino acid" refers to an amino acid exhibiting hydrophobic property and includes phenylalanine, leucine, etc.

In the present disclosure, the X of the [VPGXG VPGXG VPGXG VPGXG VPGXG VPGXG] block may include: A (Ala), G (Gly) and I (Ile) at a ratio of 1:4:1; K (Lys), G (Gly) and I (Ile) at a ratio of 1:4:1; D (Asp), G (Gly) and I (Ile) at a ratio of 1:4:1; E (Glu), G (Gly) and I (Ile) at a ratio of 1:4:1; G (Gly), A (Ala) and F (Phe) at a ratio of 1:3:2; K (Lys), A (Ala) and F (Phe) at a ratio of 1:3:2; D (Asp), A (Ala) and F (Phe) at a ratio of 1:3:2; K (Lys) and F (Phe) at a ratio of 3:3; D (Asp) and F (Phe) at a ratio of 3:3; H (His), A (Ala) and I (Ile) at a ratio of 3:2:1; H (His) and G (Gly) at a ratio of 5:1; or G (Gly), C (Cys) and F (Phe) at a ratio of 1:3:2.

In the present disclosure, the X of the [VPAXG VPAXG VPAXG VPAXG VPAXG VPAXG] block may include: A (Ala), G (Gly) and I (Ile) at a ratio of 1:4:1; K (Lys), G (Gly) and I (Ile) at a ratio of 1:4:1; D (Asp), G (Gly) and I (Ile) at a ratio of 1:4:1; E (Glu), G (Gly) and I (Ile) at a ratio of 1:4:1; or G (Gly), A (Ala) and F (Phe) at a ratio of 1:3:2.

In the present disclosure, the X of the [IPAXG IPAXG IPAXG IPAXG IPAXG] block may include G (Gly), A (Ala) and F (Phe) at a ratio of 1:4:1 or 1:3:2.

In the present disclosure, the different EBPs having Val-Pro-(Gly or Ala)-$X_{aa}$-Gly [VP(G or A)XG] as pentapeptide repeat units are named as follows. The $X_{aa}$ may be any amino acid excluding Pro. First, the repetition of the Val-Pro-Ala-$X_{aa}$-Gly (VPAXG) pentapeptide with plasticity is defined as an elastin-based polypeptide with plasticity (EBPP). Meanwhile, the repetition of the Val-Pro-Gly-$X_{aa}$-Gly (VPGXG) pentapeptide is referred to as an elastin-based polypeptide with elasticity (EBPE). And, the repetition of the Ile-Pro-Ala-$X_{aa}$-Gly (IPAXG) pentapeptide is defined as elastin-based polypeptide with plasticity with the first position replaced by Ile (EBPPI). In $[X_iY_jZ_k]_n$, the capital letters in the brackets represent the single-letter amino acid codes for the guest residues, i.e., the amino acids at the 4th position of the EBP pentapeptide ($X_{aa}$ or X), and their subscripts represent the ratio of the guest residues of the EBP monomer gene. The subscript n of the $[X_iY_jZ_k]_n$ represents the total number of repetitions of EBP of SEQ ID NO 1 [VPGXG VPGXG VPGXG VPGXG VPGXG VPGXG], SEQ ID NO 2 [VPAXG VPAXG VPAXG VPAXG VPAXG VPAXG] or SEQ ID NO 3[IPAXG IPAXG IPAXG IPAXG IPAXG IPAXG] of the present disclosure. For example, EBPP $[G_1A_3F_2]_{12}$ is an EBPP block consisting of 12 repeat units of SEQ ID NO 2 [VPAXG VPAXG VPAXG VPAXG VPAXG VPAXG], wherein the ration of Gly, Ala and Phe at the 4th guest residue position ($X_{aa}$) is 1:3:2.

The gene and amino acid sequences of the EBP blocks of the present disclosure are shown in Tables 1 and 2, respectively.

TABLE 1

| Gene sequences of EBP library | |
|---|---|
| EBPE$[A_1G_4I_1]$ (SEQ ID NO 4) | GTC CCA GGT GGA GGT GTA CCC GGC GCG GGT GTC CCA GGT GGA GGTGTA CCT GGG GGT GGG GTC CCT GGT ATT GGC GTA CCT GGA GGC GGC |
| EBPP$[A_1G_4I_1]$ (SEQ ID NO 5) | GTT CCA GCT GGC GGT GTA CCT GCT GCT GCT GTT CCG GCC GGT GGTGTT CCG GCG GGC GGC GTG CCT GCA ATA GGA GTT CCC GCT GGT GGC |

TABLE 1 -continued

| Gene sequences of EBP library | |
|---|---|
| EBPE[$K_1G_4I_1$] (SEQ ID NO 6) | GTT CCG GGT GGT GGT GTT CCG GGT AAA GGT GTT CCG GGT GGT GGTGTT CCG GGT GGT GGT GGT GTT CCG GGT ATC GGT GTT CCG GGT GGC |
| EBPP[$K_1G_4I_1$] (SEQ ID NO 7) | GTT CCG GCG GGT GGT GTT CCG GCG AAA GGT GTT CCG GCG GGT GGTGTT CCG GCG GGT GGT GTT CCG GCG ATC GGT GTT CCG GCG GGT GGC |
| EBPE[$D_1G_4I_1$] (SEQ ID NO 8) | GTT CCG GGT GGT GGT GTT CCG GGT GAT GGT GTT CCG GGT GGT GGTGTT CCG GGT GGT GGT GGT GTT CCG GGT ATC GGT GTT CCG GGT GGC |
| EBPP[$D_1G_4I_1$] (SEQ ID NO 9) | GTT CCG GCG GGT GGT GTT CCG GCG GAT GGT GTT CCG GCG GGT GGTGTT CCG GCG GGT GGT GTT CCG GCG ATC GGT GTT CCG GCG GGT GGC |
| EBPE[$E_1G_4I_1$] (SEQ ID NO 10) | GTT CCG GGT GGT GGT GTT CCG GGT GAA GGT GTT CCG GGT GGT GGTGTT CCG GGT GGT GGT GGT GTT CCG GGT ATC GGT GTT CCG GGT GGC |
| EBPP[$E_1G_4I_1$] (SEQ ID NO 11) | GTT CCG GCG GGT GGT GTT CCG GCG GAA GGT GTT CCG GCG GGT GGTGTT CCG GCG GGT GGT GTT CCG GCG ATC GGT GTT CCG GCG GGT GGC |
| EBPE[$G_1A_3F_2$] (SEQ ID NO 12) | GTC CCG GGT GCG GGC GTG CCG GGA TTT GGA GTT CCG GGT GCG GGTGTT CCA GGC GGT GGT GTT CCG GGC GCG GGC GTG CCG GGC TTT GGC |
| EBPP[$G_1A_3F_2$] (SEQ ID NO 13) | GTG CCG GCG GCG GGC GTT CCA GCC TTT GGT GTG CCA GCG GCG GGAGTT CCG GCC GGT GGC GTG CCG GCA GCG GGC GTG CCG GCT TTT GGC |
| EBPP[$K_1A_3F_2$] (SEQ ID NO 14) | GTG CCG GCG GCG GGC GTT CCA GCC TTT GGT GTG CCA GCG GCG GGAGTT CCG GCC AAA GGC GTG CCG GCA GCG GGC GTG CCG GCT TTT GGC |
| EBPP[$D_1A_3F_2$] (SEQ ID NO 15) | GTG CCG GCG GCG GGC GTT CCA GCC TTT GGT GTG CCA GCG GCG GGAGTT CCG GCC GAT GGC GTG CCG GCA GCG GGC GTG CCG GCT TTT GGC |
| EBPP[$K_3F_3$] (SEQ ID NO 16) | GTT CCA GCG TTT GGC GTG CCA GCG AAA GGT GTT CCG GCG TTT GGGGTT CCC GCG AAA GGT GTG CCG GCC TTT GGT GTG CCG GCC AAA GGC |
| EBPP[$D_3F_3$] (SEQ ID NO 17) | GTT CCA GCG TTT GGC GTG CCA GCG GAT GGT GTT CCG GCG TTT GGGGTT CCC GCG GAT GGT GTG CCG GCC TTT GGT GTG CCG GCC GAT GGC |
| EBPP[$H_3A_3I_1$] (SEQ ID NO 18) | GTG CCG GCG CAT GGA GTT OCT GCC GCC GGT GTT OCT GCG CAT GGTGTA CCG GCA ATT GGC GTT CCG GCA CAT GGT GTG CCG GCC GCC GGC |
| EBPP[$H_5G_1$] (SEQ ID NO 19) | GTT CCG GCC GGA GGT GTA CCG GCG CAT GGT GTT CCG GCA CAT GGTGTG CCG GCT CAC GGT GTG OCT GCG CAT GGC GTT CCT GCG CAT GGC |
| EBPP[$G_1C_3F_2$] (SEQ ID NO 20) | GTG CCG GCG TGC GGC GTT CCA GCC TTT GGT GTG CCA GCG TGC GGA GTT CCG GCC GGT GGC GTG CCG GCA TGC GGC GTG CCG GCT TTT GGC |
| EBPPI[$G_1A_4F_1$] (SEQ ID NO 21) | ATT OCT GCA GCC GGT ATC CCG GCC GGT GGC ATT CCG GCA GCC GGC ATT CCG GCC GCC GGC ATC CCG GCA TTT GGC ATT CCT GCA GCA GGC |
| EBPPI[$G_1A_3F_2$] (SEQ ID NO 22) | ATT CCG GCC GCA GGC ATT OCT GCA TTT GGT ATT CCG GCG GCA GGC ATT OCT GCC GGT GGC ATC CCG GCA GCG GGC ATT CCG GCC TTT GGC |

TABLE 2

| Amino acid sequences of EBP library | |
|---|---|
| EBPE[$A_1G_4I_1$] (SEQ ID NO 23) | VPGGG VPGAG VPGGG VPGGG VPGIG VPGGG |
| EBPP[$A_1G_4I_1$] (SEQ ID NO 24) | VPAGG VPAAG VPAGG VPAGG VPAIG VPAGG |
| EBPE[$K_1G_4I_1$] (SEQ ID NO 25) | VPGGG VPGKG VPGGG VPGGG VPGIG VPGGG |
| EBPP[$K_1G_4I_1$] (SEQ ID NO 26) | VPAGG VPAKG VPAGG VPAGG VPAIG VPAGG |
| EBPE[$K_1G_4I_1$] (SEQ ID NO 27) | VPGGG VPGDG VPGGG VPGGG VPGIG VPGGG |
| EBPP[$K_1G_4I_1$] (SEQ ID NO 28) | VPAGG VPADG VPAGG VPAGG VPAIG VPAGG |
| EBPE[$E_1G_4I_1$] (SEQ ID NO 29) | VPGGG VPGEG VPGGG VPGGG VPGIG VPGGG |
| EBPP[$E_1G_4I_1$] (SEQ ID NO 30) | VPAGG VPAEG VPAGG VPAGG VPAIG VPAGG |
| EBPE[$G_1A_3F_2$] (SEQ ID NO 31) | VPGAG VPGFG VPGAG VPGGG VPGAG VPGFG |
| EBPP[$G_1A_3F_2$] (SEQ ID NO 32) | VPAAG VPAFG VPAAG VPAGG VPAAG VPAFG |
| EBPP[$K_1A_3F_2$] (SEQ ID NO 33) | VPAAG VPAFG VPAAG VPAGG VPAAG VPAFG |
| EBPP[$D_1A_3F_2$] (SEQ ID NO 34) | VPAAG VPAFG VPAAG VPAGG VPAAG VPAFG |
| EBPP[$K_3F_3$] (SEQ ID NO 35) | VPAFG VPAKG VPAFG VPAKG VPAFG VPAKG |
| EBPP[$D_3F_3$] (SEQ ID NO 36) | VPAFG VPADG VPAFG VPADG VPAFG VPADG |
| EBPP[$H_3A_3I_1$] (SEQ ID NO 37) | VPAHG VPAAG VPAHG VPAIG VPAHG VPAAG |
| EBPP[$H_5G_1$] (SEQ ID NO 38) | VPAGG VPAHG VPAHG VPAHG VPAHG VPAHG |
| EBPP[$G_1C_3F_2$] (SEQ ID NO 39) | VPACG VPAFG VPACG VPAGG VPACG VPAFG |
| EBPPI[$G_1A_4F_1$] (SEQ ID NO 40) | IPAAG IPAGG IPAAG IPAAG IPAFG IPAAG |
| EBPPI[$G_1A_3F_2$] (SEQ ID NO 41) | IPAAG IPAFG IPAAG IPAGG IPAAG IPAFG |

In the present disclosure, the mussel foot protein (MFP) may be California mussel foot protein 5 (*Mytilus califomianus* foot protein 5 (Mcfp5)) or Mediterranean mussel foot protein 5 (*Mytilus galloprovincialis* foot protein 5 (Mgfp5)).

In MFP[Mgfp5]$_n$ and MFP[Mcfp5]$_n$, the characters and numbers in the brackets represent the species of mussel and the type of foot protein, and the subscript 'n' represents the number of repetition of the MFP blocks. For example, MFP[Mgfp5]$_1$ means Mediterranean mussel ((*Mytilus galloprovincialis*), MFP type 5, and one MFP block repeat unit. Finally, diblock and triblock copolypeptides composed of EBP and MFP are denoted by using a hyphen between the MFP block and the EBP block. For example, a diblock copolypeptide may be denoted as EBPPI[G1A4F1]$_n$-MFP [Mgfp5]$_n$, and a triblock copolypeptide may be denoted as EBPPI[G1A4F1]$_n$-MFP[Mgfp5]$_n$-EBPPI[G1A4F1]$_n$.

The gene and amino acid sequences of the MFP blocks of the present disclosure are shown in Tables 3 and 4, respectively.

TABLE 3

| Gene sequences of MFP library | |
|---|---|
| MFP [Mgfp5] (SEQ ID NO 42) | TCT AGT GAA GAA TAT AAA GGT GGT TAT TAC CCC GGC AAC ACC TAT CAT TAT CAT AGT GGG GGC AGT TAT CAC GGC AGC GGC TAC CAT GGC GGC TAT AAA GGT AAA TAC TAC GGT AAA GCG AAA AAA TAC TAT TAT AAA TAC AAA AAC AGC GGC AAA TAT AAG TAC CTG AAA AAA GCT CGT AAA TAC CAT CGT AAA GGC TAT AAA AAA TAT TAC GGC GGC GGC AGT TCG |
| MFP [Mcfp5] (SEQ ID NO 43) | GTG GGT AGC GGC TAT GAC GGC TAT TCA GAT GGC TAC TAT CCT GGT AGT GCA TAT AAC TAC CCG TCA GGG TCC CAT GGC TAC CAT GGT CAT GGC TAT AAA GGC AAA TAC TAT GGC AAA GGC AAA AAA TAT TAC TAT AAA TAT AAA CGC ACC GGC AAG TAT AAA TAT CTG AAA AAA GCG CGC AAA TAT CAT CGC AAG GGC TAT AAA AAA TAC TAT GGT GGC GGC TCC AGT |

TABLE 4

| Amino acid sequences of MFP library | |
|---|---|
| MFP [Mgfp5] (SEQ ID NO 44) | SSEEYKGGYY PGNTYHYHSG GSYHGSGYHG GYKGKYYGKA KKYYYKYKNS GKYKYLKKAR KYHRKGYKKY YGGGSS |
| MFP [Mcfp5] (SEQ ID NO 45) | VGSGYDGYSD GYYPGSAYNY PSGSHGYHGH HYKGKYYGKG KKYYYKYKRT GKYKYLKKAR KYHRKGYKKY YGGGSS |

In In the present disclosure, the multiblock copolypeptide may be represented by an amino acid sequence of SEQ ID NOS 50-70 and may be represented by a base sequence of SEQ ID NOS 71-91.

In another aspect, the present disclosure relates to a gene encoding the multiblock copolypeptide.

In another aspect, the present disclosure relates to a recombinant vector including the gene.

In another aspect, the present disclosure relates to a recombinant microorganism with the gene or the recombinant vector introduced.

In the present disclosure, a gene encoding tyrosinase or an expression vector including a gene encoding tyrosinase may be further introduced in the recombinant microorganism for coexpression.

In the present disclosure, the mussel foot protein (MFP) may form DOPA having a hydroxylated catechol side chain at the tyrosine residue by tyrosinase, and the DOPA may bind to a metal ion, an oxide and a semimetal through coordination or hydrogen bonding.

In the present disclosure, the DOPA is stained specifically by NBT and glycinate through an oxidation-reduction reaction.

In the present disclosure, the expression vector may further include the ORF438 gene.

In another aspect, the present disclosure relates to a method for preparing a multiblock copolypeptide, including: (a) a step of producing a multiblock copolypeptide by culturing the recombinant microorganism; and (b) a step of obtaining the produced multiblock copolypeptide.

In the present disclosure, a gene encoding tyrosinase or an expression vector including a gene encoding tyrosinase may be further introduced in the recombinant microorganism of the step (a) for coexpression of the multiblock copolypeptide and tyrosinase.

In the present disclosure, a tyrosine residue of the multiblock copolypeptide may be modified to a DOPA (3,4-dihydroxyphenylalanine) residue by the tyrosinase.

The method for preparing a multiblock copolypeptide of the present disclosure is economical because the expensive tyrosinase can be expressed in large quantities in bacteria.

In the present disclosure, the vector refers to a DNA construct including the base sequence of a polynucleotide encoding a target protein, which is operably linked to an appropriate control sequence to express the target protein in a suitable host cell. The control sequence may include a promoter that can initiate transcription, an optional operator sequence for regulating the transcription, a sequence encoding a suitable mRNA ribosome binding site, and a sequence regulating the termination of transcription and translation, and may be prepared variously depending on purposes. The promoter of the vector may be constitutive or inducible. After the vector is transformed into a suitable host cell, it can replicate or function independently of the host genome, and can be integrated into the genome itself.

The vector used in the present disclosure is not particularly limited as long as it is able to replicate in a host cell, and any vector known in the art can be used. Examples of commonly used vectors may include a natural or recombinant plasmid, phagemid, cosmid, virus and bacteriophage. For instance, pWE15, M13, λMBL3, λMBL4, λIXII, λASHII, λAPII, λt10, λt11, Charon4A and Charon21A may be used as a phage vector or a cosmid vector. As a plasmid vector, pBR, pUC, pBluescriptII, pGEM, pTZ, pCL and pET may be used. The vector that can be used in the present disclosure is not particularly limited, and any known expression vector may be used.

The expression "expression control sequence" refers to a DNA sequence that is essential for expression of a coding sequence operably linked to other DNA sequences in a specific host cell. This control sequence includes a promoter for initiating transcription, an optional operator sequence for controlling the transcription, a sequence for encoding a suitable mRNA ribosome binding site, and a sequence for controlling termination of transcription and translation. For example, a control sequence specific to a prokaryote includes a promoter, an optional operator sequence and a ribosome binding site. For a eukaryote, a control sequence includes a promoter, a polyadenylation signal, and an enhancer. In a plasmid, a promoter is the factor with the greatest effect on amount of gene expression. For high level of expression, an SRa promoter, a cytomegalovirus-derived promoter, etc. may be used.

To express the DNA sequence of the present disclosure, any one of various expression control sequences may be applied to a vector. For example, useful expression control sequences include early and late promoters of SV40 or adenovirus, a lac system, a trp system, a TAC or TRC system, T3 and T7 promoters, a major operator and promoter region of phage λ, a control region of fd code protein, a promoter for 3-phophoglycerate kinase or other glycolytic enzymes, promotors for the phosphatases, e.g., Pho5, a promoter for a yeast alpha-mating system, other sequences of constructs known for controlling the expression of genes of prokaryotes, eukaryotes or viruses and combinations thereof. The T7 RNA polymerase promoter Φ10 can be usefully used to express protein NSPs in *E. coli.*

A nucleic acid is operably linked when it is arranged with another nucleic acid sequence in a functional relationship. The nucleic acid may be a gene and a control sequence(s) linked to be capable of expressing the gene when it binds to a control sequence(s) (e.g., transcription-activating protein). For example, a DNA for a pre-sequence or a secretory leader is operably linked to a DNA for a polypeptide when it is expressed as a pre-protein participating in secretion of the polypeptide; a promoter or an enhancer is operably linked to a coding sequence when it affects the transcription of the sequence; and a ribosome binding site is operably linked to a coding sequence when it affects the transcription of the sequence, or is operably linked to a coding sequence when it is arranged to facilitate translation. Generally, the term "operably linked" means that the linked DNA sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to the conventional method.

The term "expression vector" used herein generally means a double-stranded DNA fragment functioning as a recombinant carrier into which a heterologous DNA fragment is inserted. Here, the heterologous DNA means a hetero-type DNA, which is not naturally found in a host cell. The expression vector may be self-replicable regardless of the host chromosomal DNA once it is present in the host cell, and may produce several copies of the vector and (heterologous) DNA inserted thereinto.

As is well known in the art, in order to increase the expression level of a transfected gene in a host cell, the corresponding gene should be operably linked to transcription and translation expression control sequences which are operated in a selected expression host. Specifically, the expression control sequences and the corresponding gene are included in one expression vector together with a bacterial selection marker and a replication origin. When the expression host is a eukaryotic cell, the expression vector should further include an expression marker which is useful in the eukaryotic expression host.

A variety of combinations of expression host/vector may be used to express a gene encoding the polypeptide of the present disclosure. Examples of expression vectors suitable for eukaryotic hosts include expression control sequences derived from SV40, bovine papillomavirus, adenovirus, adeno-associated virus, cytomegalovirus and retrovirus. Expression vectors that may be used for bacterial hosts include bacterial plasmids that can be obtained from *E. coli*, e.g., pBluescript, pGEX2T, pUCvector, colE1, pCR1, pBR322, pMB9 and derivatives thereof, plasmids having broader host ranges such as RP4, phage DNAs, e.g., various phage lambda derivatives such as λgt10, λgt11 and NM989, and other DNA phages such as M13 and filamentous single-stranded DNA phages. Expression vectors suitable for yeast cells are 2μ plasmid and derivatives thereof. A vector suitable for insect cells is pVL 941.

In another aspect, the present disclosure relates to a host cell transformed or transfected with the expression vector described above. The term "transformation", as used herein, means that DNA can be replicated as a factor outside of chromosome or by means of completion of the entire chromosome by introducing the DNA as a host. As used herein, the term "transfection" means that an expression vector is accepted by a host cell regardless of whether or not any coding sequence is actually expressed.

The host cell of the present disclosure refers to a recombinant microorganism into which a vector having a polynucleotide encoding one or more target protein is introduced, or a recombinant microorganism transfected to express the target protein as a polynucleotide encoding one or more target protein is incorporated into the chromosome. The host cell may be a prokaryotic or eukaryotic cell. In general, a host cell exhibiting high DNA introduction efficiency and high expression efficiency of the introduced DNA is used. Examples of the host cell that can be used include known eukaryotic and prokaryotic host cells such as *E. coli, Pseudomonas, Bacillus, Streptomyces*, fungi and yeast, insect cells such as *Spodoptera frugiperda* (SF9), animal cells such as CHO and mouse cells, African green monkey cells such as COS 1, COS 7, BSC 1, BSC 40 and BMT 10, and tissue-cultured human cells. When COS cells are used, since SV40 large T antigen is expressed in the COS cells, the plasmid having the origin of replication of SV40 is present as a large number of copies of the episome in the cells and higher expression can be expected. The introduced DNA sequence may be obtained from the same species as the host cell, may be of a species different from the host cell, or may be a hybrid DNA sequence including any heterologous or homologous DNA.

Of course, it should be understood that not all vectors and expression control sequences function equally in expressing the DNA sequences of the present disclosure. Likewise not all hosts function equally for the same expression system. However, those skilled in the art can make appropriate choices from among various vectors, expression control sequences and hosts without departing from the scope of the present disclosure without undue experimental burden. For example, in selecting a vector, the host must be considered, since the vector must be replicated in it. The number of copies of the vector, the ability to control the number of copies, and the expression of other proteins encoded by the vector, such as antibiotic markers, must also be considered. In selecting expression control sequences, several factors must be considered. For example, the relative strength of the sequence, controllability and compatibility with the DNA sequences of the present disclosure should be considered, particularly with regard to possible secondary structures. Single cell hosts must be selected in consideration of the selected vector, the toxicity of the product encoded by the DNA sequence of the present disclosure, the secretory properties, the ability to accurately fold the protein, the culture and fermentation requirements, the easiness of purification of the product encoded by the DNA sequence of the present disclosure from the host, etc. Within the scope of these variables, one skilled in the art can select various vector/expression control sequence/host combinations that can express the DNA sequences of the present disclosure in fermentation or large-scale animal culture. As a screening method when cloning the cDNA of the NSP protein by expression cloning, a binding method, a panning method, a film emulsion method, etc. can be applied.

In the present disclosure, as a method for inserting the gene into the chromosome of a host cell, a commonly known gene manipulication method may be used. Methods of non-viral delivery include electroporation, lipofection, microinjection, biolistics, virosomes, liposomes, immunoliposomes, polycation or lipid:nucleic acid conjugates, naked DNAs, artificial virions, and agent-enhanced DNA uptake. Sonoporation using, e.g., the Sonitron 2000 system (Rich-Mar) can also be used for delivery of nucleic acids. Additional exemplary nucleic acid delivery systems include those provided by Amaxa Biosystems (Cologne, Germany), Maxcyte, Inc. (Rockville, Md.) and BTX Molecular Delivery Systems (Holliston, Mass.). The lipofection method is described in, e.g., U.S. Pat. Nos. 5,049,386, 4,946,787 and 4,897,355, and lipofection reagents are sold commercially (e.g., Transfectam™ and Lipofectin™). Cationic and neutral lipids that are suitable for efficient receptor-recognition lipofection of polynucleotides include those of Feigner (WO 91/17424 and WO 91/16024). Delivery can be made into cells (through ex-vivo introduction) or target tissues (through in-vivo introduction). The preparation of lipid: nucleic acid complexes, including targeted liposomes such as immunolipid complexes, is well known to one of skill in the art (Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028 and 4,946,787).

The tropism of a retrovirus can be altered by incorporating foreign envelope proteins, thereby expanding the potential population of target cells. Lentiviral vectors are retroviral vectors that are able to transduce or infect non-dividing cells and typically produce high viral titers. The selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV) and combinations thereof (Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In case of temporarily expressing a sucrose phosphorylase protein, an adenoviral-based system is frequently used. Adenoviral-based vectors provide very high transduction efficiency in many cell types and do not require cell division. When these vectors are used, high titer and high levels of expression may be obtained and a large-scale production is possible with a relatively simple system. In addition, adeno-associated viral ("AAV") vectors are also used to transduce cells with target nucleic acids, for example, for in-vitro production of nucleic acids and peptides, and for in-vivo and ex-vivo gene therapy (West et al., *Virology.,* 160:38-47, 1987; U.S. Pat. No. 4,797,368; WO 93/24641; Kotin, *Human Gene Therapy.,* 5:793-801, 1994; Muzyczka, *J. Clin. Invest.,* 94:1351, 1994), and the construction of recombinant AAV vectors is already known (U.S. Pat. No. 5,173,414; Tratschin et al., *Mol. Cell. Biol.,* 5:3251-3260, 1985; Tratschin, et al., *Mol. Cell. Biol.,* 4:20722081, 1984; Hermonat & Muzyczka, *PNAS.,* 81:6466-6470, 1984; Samulski et al., *J Virol.,* 63:3822-3828, 1989). In clinical trials, genes are transferred using at least six viral vector, which involves complementation of defective vectors by genes inserted into helper cell lines to generate the transducing agent. pLASN and MFG-S are examples of retroviral vectors that have been used in clinical trials (Dunbar et al., *Blood.,* 85:3048, 1995; Kohn et al., *Nat. Med.,* 1:1017, 1995; Malech et al., *PNAS.,* 94:12133, 1997), PA317/pLASN is the first therapeutic vector used in a gene therapy trial (Blaese et al.,

*Science.,* 270:475-480, 1995), and transduction efficiencies of 50% or greater have been observed for MFG-S packaged vectors (Ellem et al., *Immunol Immunother.,* 44(1):10-20, 1997; Dranoff et al., *Hum. Gene Ther.,* 1:111-2, 1997).

Recombinant adeno-associated virus vectors (rAAV) are a promising alternative gene delivery system based on the defective and nonpathogenic parvovirus adeno-associated type 2 virus. All vectors are derived from a plasmid that retains the AAV 145 bp inverted terminal repeats flanking the transgene expression cassette. Efficient gene transfer and stable transgene delivery due to integration into the genomes of the transduced cell are key features for this vector system (Wagner et al., *Lancet.,* 351:9117, 1998; Kearns et al., *Gene Ther.,* 9:748-55, 1996).

In the present disclosure, "coexpression" refers to expression of two or more genes at the same time.

In an exemplary embodiment of the present disclosure, the tyrosine residue of the MFP block is hydroxylated by two methods ((1) bacterial coexpression system (coexpression of ORF438, tyrosinase and block copolypeptide in *E. coli*) and (2) catalytic reaction by mushroom-derived tyrosinase). The diblock and triblock copeptides composed of EBP (block A) and MFP (block B) designed into AB-, ABA-and BAB-types form self-assembled micelle structures and injectable hydrogels and can be used as biocoating and bioadhesive materials having surface adhesivity. First, a purified EBP-MFP block copolypeptide is changed to DOPA as the tyrosine residue was modified by mushroom-derived tyrosinase. In order to investigate surface adhesiveness, each block copolypeptide was dissolved in 10 mM phosphate buffer (pH 5) (for preventing autoxidation of DOPA) and incubated with $NaIO_4$ (for intermolecular crosslinking). As a result, different surface adhesivity was observed for the oxidizing agent at concentrations of 10-100 mM depending on the type of the block copolypeptide. Through this, it can be seen that DOPA and quinone are essential components in achieving bulk adhesivity. In the MFP, DOPA plays an important role in surface adhesion. Quinone, which is an oxidized form of DOPA, provides cohesive force through intermolecular crosslinking. In addition, the EBP block exhibiting phase transition at LOST or above provides improved cohesive force for physically crosslinked hydrogelation and surface adhesion. Second, the EBP-MFP block copolypeptide, ORF438 and tyrosinase were coexpressed in *E. coli* to hydroxdylate the tyrosine residue of the block copolypeptide without further treatment. As a result, it was confirmed that the EBP-MFP block copolypeptide has superior adhesivity as compared to the EBP-MFP block copolypeptide modified by mushroom-derived tyrosinase and is useful for industrial scales (FIG. 12). In addition, the strength of surface adhesion of the block copolypeptide coexpressed in the form of micelles and hydrogels was investigated. As a result, it was confirmed that the EBP-MFP block copolypeptide of the present disclosure has a great potential as micelles and hydrogels having surface adhesiveness (FIG. 10, FIG. 11, FIG. 13 and FIG. 14).

In another aspect, the present disclosure relates to a self-assembled nanostructure of a core-shell structure, wherein an EBP block of the multiblock copolypeptide forms a core structure and an MFP block forms a shell structure in response to temperature stimulation. In the present disclosure, the core-shell structure means a micelle structure.

In general, the micelle refers to a thermodynamically stable and uniform spherical structure composed of low-molecular-weight materials having amphiphilic, e.g., hydrophilic ad hydrophobic, groups at the same time. When a nonaqueous drug is administered by dissolving in a compound having a micelle structure, the drug is present inside the micelle. Since the micelle enables target-oriented drug release in response to the change in temperature or pH in vivo, it has a high potential for use as a carrier for drug delivery.

In the present disclosure, a self-assembled nanostructure is formed as MFP and EBPPI with different block lengths are fused in response to thermal stimulus. The EBPPI-MFP diblock copolypeptide molecule may be self-assembled into a core-shell nanostructure in response to temperature (FIG. 1(A)). MFP is fused to the N-terminal or C-terminal of EBPPI[G1A4F1]6 and exhibits surface adhesiveness in the presence of water. The surface-adhesive micelle may be applied to a stent as a surface-coated nanostructure, and may serve as a passage and drug delivery carrier by being inserted into the lumen of a blood vessel.

In another aspect, the present disclosure relates to a drug delivery composition containing the self-assembled nanostructure.

The self-assembled nanostructure according to the present disclosure may be used as a matrix of artificial cells, as a scaffold for drug delivery. The drug is not particularly limited and includes a chemical substance, a small molecule, a peptide or protein drug, a nucleic acid, a virus, an antibacterial agent, an anticancer agent, an antiinflammatory agent, etc.

The small molecule may be, for example, a contrast agent (e.g., T1 contrast agents, T2 contrast agents such as supraparamagnetic materials, radioisotopes, etc.), a fluorescence marker, a dye, etc., although not being limited thereto.

The peptide or protein drug includes a hormone, hormone analogue, an enzyme, an enzyme inhibitor, a signal transducing protein or a fragment thereof, an antibody or a fragment thereof, a single-chain antibody, a binding protein or a binding domain thereof, an antigen, an adherence protein, a structural protein, a regulatory protein, a toxin protein, a cytokine, a transcriptional regulatory factor, a blood coagulation factor, a vaccine, etc., although not being limited thereto. More specifically, it includes fibroblast growth factor (FGF), vascular endothelial growth factor (VEGF), transforming growth factor (TGF), bone morphogenetic protein (BMP), human growth hormone (hGH), porcine growth hormone (pGH), granulocyte colony-stimulating factor (G-CSF), erythropoietin (EPO), macrophage colony-stimulating factor (M-CSF), tumor necrosis factor (TNF), epithelial growth factor (EGF), platelet-derived growth factor (PDGF), interferons, interleukins, calcitonin, nerve growth factor (NGF), growth hormone-releasing hormone, angiotensin, luteinizing hormone-releasing hormone (LHRH), luteinizing hormone-releasing hormone agonist (LHRH agonist), insulin, thyrotropin-releasing hormone (TRH), angiostatin, endostatin, somatostatin, glucagon, endorphine, bacitracin, mergain, colistin, monoclonal antibodies, vaccines or mixtures thereof, although not being limited thereto.

The nucleic acid may be RNA, DNA or cDNA, and the sequence of the nucleic acid may be a coding region sequence or a non-coding region sequence (e.g., antisense oligonucleotide or siRNA).

The virus may be an entire virus or a viral core including the nucleic acid of the virus (i.e., nucleic acid of virus packaged without viral envelope). Examples of the virus and viral core that can be delivered include papillomavirus, adenovirus, baculovirus, retroviral core, semilkiviral core, etc., although not being limited thereto.

The antibacterial agent may be minocycline, tetracycline, ofloxacin, fosfomycin, mergain, profloxacin, ampicillin, penicillin, doxycycline, thienamycin, cephalosporin, nocardicin, gentamicin, neomycin, kanamycin, paromomycin, micronomicin, amikacin, tobramycin, dibekacin, cefotaxime, cefaclor, erythromycine, ciprofloxacin, levofloxacin, enoxacin, vancomycin, imipenem, fusidic acid and mixtures thereof, although not being limited thereto.

The anticancer agent may be paclitaxel, taxotere, adriamycin, endostatin, angiostatin, mitomycin, bleomycin, cisplatin, carboplatin, doxorubicin, daunorubicin, idarubicin, 5-fluorouracil, methotrexate, actinomycin-D and mixtures thereof, although not being limited thereto.

The antiinflammatory agents may be acetaminophen, aspirin, ibuprofen, diclofenac, indometacin, piroxicam, fenoprofen, flubiprofen, ketoprofen, naproxen, suprofen, loxoprofen, cinnoxicam, tenoxicam and mixtures thereof, although not being limited thereto.

In another aspect, the present disclosure relates to a hydrogel prepared as the multiblock copolypeptide forms crosslinkages between the block polypeptides in response to temperature stimulation.

The hydrogel of the present disclosure has mechanical flexibility similar to that of actual tissue and contains a lot of water, but the bonds of the gel is not broken by the water. Therefore, it is widely applied to medical adhesives, etc., which require adhesion on the water-containing surface and resistance to water. Accordingly, the hydrogel having superior tissue adhesiveness according to the present disclosure is applicable to various biomedical applications for tissue adhesives, hemostatics, scaffolds for tissue engineering, drug delivery carriers, tissue fillers, wound healing, prevention of intestinal adhesion, etc.

In the present disclosure, two triblock copolypeptides having various block sequences and lengths were prepared. MFP[Mgfp5]$_1$-EBPPI[$G_1A_4F_1$]$_6$-MFP[Mgfp5]$_1$ and EBPPI [$G_1A_4F_1$]$_6$-MFP[Mgfp5]$_1$-EBPPI[$G_1A_4F_1$]$_6$ triblock copolypeptides were prepared as injectable hydrogels having surface adhesiveness (FIG. 1(B) and FIG. 1(C)).

In the present disclosure, the EBP block is used as a physical crosslinking agent having stimulus responsivity, whereas the MFP block is used for surface adhesiveness and introduction of chemical crosslinking through formation of quinone. The MFP-EBP-MFP and EBP-MFP-EBP triblock copolypeptides can be self-assembled to hydrogels through oxidation in response to change in temperature or treatment with $NaIO_4$. The mechanisms of surface adhesion, intermolecular crosslinking and stimulus responsivity of the triblock copolypeptides are shown in FIG. 1(D).

In the present disclosure, the hydrogel may be formed through oxidation or noncovalent interaction of a DOPA (3,4-dihydroxyphenylalanine) residue included in the mussel foot protein (MFP).

In another aspect, the present disclosure relates to a bioadhesive composition containing the hydrogel.

The bioadhesive composition of the present disclosure can be used in various fields including skin, blood vessels, digestive organs, cranial nerve, plastic surgery, orthopedic surgery, etc. by replacing cyanoacrylate-based adhesives, fibrin glues, etc. For example, the biocompatible tissue adhesive of the present disclosure can replace surgical suture and can be used for obstruction of unnecessary blood vessels, stanching and suture of soft tissue such as facial tissue, cartilage, etc. and hard tissue such as bone, tooth, etc. and household medicine. Various applications of the biocompatible bioadhesive composition of the present disclosure can be summarized as follows.

In an exemplary embodiment, the bioadhesive of the present disclosure can be applied to the inner and outer surfaces of the human body. That is to say, the bioadhesive of the present disclosure can be applied topically onto the outer surface of the human body such as skin or onto the surface of internal organs exposed during surgery. In addition, the bioadhesive of the present disclosure may be used to bond damaged tissue, prevent leakage of air/fluid from tissue, adhere a medical device to tissue or fill the defective part of tissue. In the present disclosure, the term "biological tissue" is not particularly limited and includes, for example, skin, bone, nerve, axon, cartilage, blood vessel, cornea, muscle, fascia, brain, prostate gland, breast, endometrium, lung, spleen, small intestine, liver, testicle, ovary, cervix, rectum, stomach, lymph node, bone marrow, kidney, etc.

In another exemplary embodiment, the bioadhesive of the present disclosure may be used for wound healing. For example, the biocompatible bioadhesive of the present disclosure may be used for wound dressing.

In another exemplary embodiment, the bioadhesive of the present disclosure may be used for skin suture. That is to say, the bioadhesive of the present disclosure may be used topically to suture a wound, replacing a stitching fiber. In addition, the bioadhesive of the present disclosure may also be used for hernia repair. For example, it may be used for surface coating of a mesh used for hernia repair.

In another exemplary embodiment, the bioadhesive of the present disclosure may also be used for suturing and prevention of leakage of a tubular structure such as blood vessel. In addition, the bioadhesive of the present disclosure may also be used for hemostasis.

In another exemplary embodiment, the bioadhesive of the present disclosure may be used as an anti-adhesive agent after surgery. Adhesion refers to the phenomenon of tissues nearby surgical site adhering to the wound following surgery. Adhesion occurs in about 97% of cases after surgery, and may cause severe problems in 5-7%. Often, the surgical site is minimized or an antiinflammatory agent is used to prevent the adhesion. Further, to prevent fibrosis, TPA (tissue plasminogen activator) may be activated or a physical barrier such as a crystalline solution, a polymer solution, a solid membrane, etc. may be used. But, these methods may cause toxicity and other adverse effects in vivo. The bioadhesive of the present disclosure may be applied to a tissue exposed after surgery to prevent adhesion between the tissue and surrounding tissues.

In another aspect, the present disclosure relates to a surgical suture including the hydrogel.

In another aspect, the present disclosure may relate to a scaffold for tissue engineering, which includes the hydrogel of the present disclosure.

Tissue engineering refers to a process of culturing cells separated from the tissue of a patient on a scaffold to prepare a cell-scaffold complex, and then transplanting the prepared cell-scaffold complex into the body. Tissue engineering is applied to regeneration of almost all organs such as artificial skin, artificial bone, artificial cartilage, artificial cornea, artificial blood vessel, artificial muscle, etc. The bioadhesive hydrogel of the present disclosure may provide a scaffold similar to a biological tissue, in order to optimize regeneration of the biological tissues and organs in tissue engineering. Further, the scaffold of the present disclosure may be used to easily implement an artificial extracellular matrix, and may be utilized as a medical material such as cosmetics, wound dressing, dental matrix, etc.

To the hydrogel of the present disclosure, a variety of physiologically active substances involved in promoting cell growth and differentiation and helping regeneration and recovery of tissues via interaction with cells or tissues of a living body may be easily adhered. The physiologically active substances generally refer to biomolecules which may be included in order to implement an artificial extracellular matrix having a similar structure to that of a natural extracellular matrix. The physiologically active substances may include cells, proteins, nucleic acids, sugars, enzymes, etc., and for example, cells, proteins, polypeptides, polysaccharides, monosaccharides, oligosaccharides, fatty acids, nucleic acids, etc., specifically, cells. The cells may be all cells including prokaryotic cells and eukaryotic cells, and may be exemplified by immunocytes and embryonic cells, including osteoblasts, fibroblasts, hepatocytes, neurons, cancer cells, B cells, white blood cells, etc. In addition, the physiologically active substances may include a plasmid nucleic acid as a nucleic acid material, hyaluronic acid, heparin sulfate, chondroitin sulfate, or alginate as a sugar material, or a hormone protein as a protein material, although not being limited thereto.

Hereinafter, the present disclosure will be described in detail through examples. However, the following examples are for illustrative purposes only and it will be apparent to those of ordinary skill in the art that the scope of the present disclosure is not limited by the examples.

EXAMPLE 1

Preparation of Experimental Materials

A pET-21a vector and BL21 (DE3) *E. coli* were purchased from Novagen Inc. (Madison, Wis., U.S.). Top10 competent cells were purchased from Invitrogen (Carlsbad, Calif., U.S.). Oligonucleotides were synthesized chemically by Cosmo Gene Tech (Seoul, South Korea). The thermosensitive alkaline phsphatase Fast AP and restriction endonucleases including BamHI and XbaI were purchased from Fermentas (Ontario, Canada). Other restriction endonucleases including BseRI, AcuI, etc. were acquired from New England Biolabs (Ipswich, Mass., U.S.). T4 DNA ligase was obtained from Elpis Biotech (Taejeon, South Korea). All kits for DNA minipreparation, gel extraction and PCR purification were obtained from Geneall Biotechnology (Seoul, South Korea). Dyne Agarose High was obtained from Dyne Bio (Seongnam, South Korea). All the Top10 cells were grown in TB DRY medium (MO BIO Laboratories, Carlsbad, Calif., U.S.) and SOC (super optimal broth with catabolite repression) medium (Formedium, UK) supplemented with 20 mM glucose. All the BL21 (DE3) cells were grown in the Circlegrow medium obtained from MP Biomedicals (Solon, Ohio, U.S.). The precast gel, Ready Gel (Tris-HCl, 2-20%), was obtained from Bio-Rad (Hercules, Calif., U.S.). Phosphate-buffered saline (PBS, pH 7.4), ampicillin and polyethyleneimine (PEI) were purchased from Sigma-Aldrich (St Louis, Mo.).

EXAMPLE 2

Synthesis of MFP Gene

MFP gene was acquired from *M. galloprovincialis*- and *M. californianus*-derived foot protein 5. A pUC plasmid including the MFP gene sequence was treated at 37° C. with a buffer containing 10 U of XbaI and 15 U of Acu1 for 30-60 minutes and then an mpET-21a plasmid vector was treated with 10 U of XbaI and 15 U of BseRI. Subsequently, ligation was conducted by incubating 90 pmol of MFP dsDNA and 30 pmol of a linearized mpET-21a cloning vector in a T4 DNA ligase buffer containing 1 U of T4 DNA ligase at 16° C. for 30 minutes. The ligated plasmid was transformed into Top 10 chemocompetent cells and then coated on an SOC plate supplemented with 50 μg/mL ampicillin. Then, the inserted sequence was identified by DNA sequencing (Table 3).

In order to achieve strong adhesivity by increasing the number of DOPA molecules, the MFP gene sequence was multimerized up to 4 repeat units. The sequence and size of the multimerized gene encoding the MFP gene were identified by DNA sequencing and DNA agarose gel electrophoresis.

As a result, the length of MFP varied from 231 bp to 924 bp as shown in FIG. 2, because the MFP was repeated 1, 2 and 4 times.

EXAMPLE 3

Establishment of Block Copolypeptide Gene Composed of EBP and MFP

A block copolypeptide library composed of EBP and MFP was synthesized using plasmids having EBP or MFP monoblock genes. The plasmids including EBP, represented by the gene and amino acid sequences shown in Table 1 and Table 2, were treated at 37° C. for 30-60 minutes with a buffer containing 10 U of XbaI and 15 U of BseRI and then purified with a PCR purification kit. The plasmids having the MFP block gene were treated at 37° C. for 30-60 minutes with a buffer containing 10 U of XbaI and 15 U of AcuI. The MFP genes represented by the amino acid sequences shown in Table 3 were separated by agarose gel electrophoresis and then purified with a gel purification kit. A plasmid having an EBP block was used as a vector and the MFP gene was fused as an insert. Ligation was conducted by incubating 90 pmol of the purified insert and 30 pmol of the linearized vector in a ligase buffer containing 1 U of T4 DNA ligase at 16° C. for 30-60 minutes. Subsequently, the product was transformed into Top10 competent cells and then streaked on an SOC plate supplemented with 50 μg/mL ampicillin. In order to synthesize diblock and triblock copolypeptides of EBP and MFP, the EBPPI-MFP diblock gene was synthesized by inserting the MFP gene to the 5'- or 3'-end of the EBPPI gene. The MFP-EBPPI-MFP or EBPPI-MFP-EBPPI triblock gene was synthesized by inserting the MFP or EBPPI gene to the 5'- or 3'-end of the EBPPI-MFP diblock gene. Other diblock and triblock copolypeptide genes were synthesized by varying the sequence and length of EBP and MFP blocks.

The triblock copolypeptide was synthesized by RDL (recursive directional ligation) using the diblock copolypeptide as a building block (FIG. 3(B)). The EBPPI[G1A4F1]6-MFP[Mgfp5]1-EBPPI[G1A4F1]6 triblock copolypeptide gene was synthesized by fusing the EBPPI[G1A4F1]6 gene to the N-terminal of the MFP[Mgfp5]1-EBPPI[G1A4F1]6 diblock copolypeptide gene seamlessly by RDL.

The length and molecular weight of the diblock copolypeptide are given in Table 5.

TABLE 5

| Diblock copolypeptides | Nucleotide chain length (bp) | M.W (kDa) |
|---|---|---|
| MFP[Mgfp5]$_1$-EBPP[G$_1$A$_3$F$_2$]$_{24}$ (SEQ ID NO 50) | 2400 | 69.55 |

TABLE 5 -continued

| Diblock copolypeptides | Nucleotide chain length (bp) | M.W (kDa) |
|---|---|---|
| MFP[Mgfp5]$_2$-EBPP[$G_1A_3F_2$]$_{24}$ (SEQ ID NO 51) | 2631 | 78.47 |
| MFP[Mgfp5]$_4$-EBPP[$G_1A_3F_2$]$_{24}$ (SEQ ID NO 52) | 3093 | 96.31 |
| MFP[Mgfp5]$_1$-EBPPI[$G_1A_3F_2$]$_{24}$ (SEQ ID NO 53) | 780 | 25.23 |
| MFP[Mgfp5]$_2$-EBPPI[$G_1A_3F_2$]$_{24}$ (SEQ ID NO 54) | 1011 | 34.15 |
| MFP[Mgfp5]$_4$-EBPPI[$G_1A_3F_1$]$_6$ (SEQ ID NO 55) | 1470 | 51.98 |
| MFP[Mgfp5]$_1$-EBPPI[$G_1A_4F_1$]$_6$ (SEQ ID NO 56) | 780 | 24.40 |
| MFP[Mgfp5]$_2$-EBPPI[$G_1A_4F_1$]$_6$ (SEQ ID NO 57) | 1011 | 33.20 |
| MFP[Mgfp5]$_4$-EBPPI[$G_1A_4F_1$]$_6$ (SEQ ID NO 58) | 1470 | 50.15 |

The length and molecular weight of the triblock copolypeptide are given in Table 6.

TABLE 6

| Triblock copolypeptides | Chain length (bp) | M.W (kDa) |
|---|---|---|
| EBPPI[$G_1A_3F_2$]$_6$-MFP[Mgfp$_5$]$_1$-EBPPI[$G_1A_3F_2$]$_6$ (SEQ ID NO 59) | 1320 | 41.13 |
| EBPPI[$G_1A_3F_2$]$_6$-MFP[Mgfp$_5$]$_2$-EBPPI[$G_1A_3F_2$]$_6$ (SEQ ID NO 60) | 1551 | 50.05 |
| EBPPI[$G_1A_3F_2$]$_6$-MFP[Mgfp$_5$]$_4$-EBPPI[$G_1A_3F_2$]$_6$ (SEQ ID NO 61) | 2010 | 67.88 |
| EBPPI[$G_1A_4F_1$]$_6$-MFP[Mgfp$_5$]$_1$-EBPPI[$G_1A_4F_1$]$_6$ (SEQ ID NO 62) | 1320 | 40.10 |
| EBPPI[$G_1A_4F_1$]$_6$-MFP[Mgfp$_5$]$_2$-EBPPI[$G_1A_4F_1$]$_6$ (SEQ ID NO 63) | 1551 | 49.50 |
| EBPPI[$G_1A_4F_1$]$_6$-MFP[Mgfp$_5$]$_4$-EBPPI[$G_1A_4F_1$]$_6$ (SEQ ID NO 64) | 2010 | 67.10 |
| MFP[Mgfp$_5$]$_1$-EBPPI[$G_1A_3F_2$]$_6$-MFP[Mgfp$_5$]$_1$ (SEQ ID NO 65) | 1050 | 34.16 |
| MFP[Mgfp$_5$]$_2$-EBPPI[$G_1A_3F_2$]$_6$-MFP[Mgfp$_5$]$_2$ (SEQ ID NO 66) | 1500 | 52.40 |
| MFP[Mgfp$_5$]$_4$-EBPPI[$G_1A_3F_2$]$_6$-MFP[Mgfp$_5$]$_4$ (SEQ ID NO 67) | 2436 | 94.77 |
| MFP[Mgfp$_5$]$_1$-EBPPI[$G_1A_4F_1$]$_6$-MFP[Mgfp$_5$]$_1$ (SEQ ID NO 68) | 1050 | 33.40 |
| MFP[Mgfp$_5$]$_2$-EBPPI[$G_1A_4F_1$]$_6$-MFP[Mgfp$_5$]$_2$ (SEQ ID NO 69) | 1500 | 52.35 |
| MFP[Mgfp$_5$]$_4$-EBPPI[$G_1A_4F_1$]$_6$-MFP[Mgfp$_5$]$_4$ (SEQ ID NO 70) | 2436 | 88.03 |

EXAMPLE 4

PCR of Tyrosinase and ORF438 and Vector Construction for Bacterial Coexpression

*E. coli* cells were grown in TB dry medium containing 50 μg/mL ampicillin. pIJ702, a plasmid including tyrosinase and *S. lividans* including ORF438 were acquired from American Type Culture Collection (ATCC, 35387). The single colony of *S. lividans* was grown in R2 YE medium at 30° C. A plasmid including both tyrosinase and ORF438 was purified from *S. lividans*. The tyrosinase gene was purified by polymerase chain reaction (PCR) using pSA-tyr-5p and pSA-tyr-3' primers (pSA-tyr-5p (SEQ ID NO 46): 5'-g gaG GAT CCg acc gtc cgc aag aac cag-3'; pSA-tyr-3' (SEQ ID NO 47): 5'-gga AAG CTT gac gtc gaa ggt gta gtg ccg-3'). The amplified PCR product was treated with BamI and HindIII. Similarly, the ORF438 gene was amplified by PCR using pSA-438-5' and pSA-438-3' primers and the amplified product was treated with EcoRV and KpnI (pSA-438-5' (SEQ ID NO 48): 5'-c acG ATA TCg ccg gaa ctc acc cgt cgt-3', pSA-438-3' (SEQ ID NO 49): 5'-caa GTT ACC gtt gga ggg gaa ggg gag gag-3'). The expression vector, pACYCDuet-1 plasmid (Merck, Darmstadt, Germany), was treated with the same restriction enzymes as for the PCR product and the cleaved product was introduced. Finally, the DNA sequence was identified by DNA sequencing.

EXAMPLE 5

Coexpression of Block Copolypeptide, ORF438 and Tyrosinase and Purification of Block Copolypeptide

*E. coli* BL21 (DE3) cells including a plasmid having pET21a with the block copolypeptide and pACYC of ORF438 and tyrosinase were grown in Circlegrow medium. The cells were inoculated to 50 mL of TB medium supplemented with 50 μg/mL ampicillin (Duchefa) and 50 μg/mL chloramphenicol (Duchefa) per mL of the colony. Preculturing was conducted at 37° C. and 200 rpm overnight under shaking. After inoculating 500 mL of high nutrition medium (Circlegrow) containing 50 μg/mL ampicillin and chloramphenicol to the pre-cultured medium, incubation was conducted at 37° C. and 200 rpm until OD600 of 0.6-0.8 was reached. In order to induce protein expression, incubation was conducted further at 37° C. and 200 rpm overnight after adding isopropyl-β-D-thiogalactopyranoside (IPTG) with a final concentration of 1 mM. Then, the cells were obtained by conducting centrifugation at 4° C. and 4,500 rpm for 10 minutes. The expressed EBPPI-MFP block copolypeptide was purified by ITC (inverse transition cycling). The cell pellet was resuspended in 5% acetic acid containing 8 M urea. Subsequently, the cells were lysed by sonicating (VC-505, Sonic and Materials Inc., Danbury, Conn.) in an ice bath for 10 seconds and cooling for 30 seconds. The cell lysate was centrifuged in a 50-mL centrifugal tube at 4° C. and 13000 rpm for 15 minutes in order to precipitate insoluble residues in the cell lysate. Then, the supernatant including the soluble EBPPI-MFP block copolypeptide was transferred to a fresh 50-mL centrifugal tube and nucleic acid contaminants were precipitated by conducting centrifugation at 4° C. and 13000 rpm for 15 minutes. The ITC (inverse transition cycling) of EBPPI was conducted several times by adding sodium chloride with a final concentration of 0.5-1.0 M. The EBPPI-MFP block copolypeptide was aggregated due to the salt effect and separated from the lysate by conducting centrifugation at 37° C. and 13,000 rpm for 15 minutes. The aggregated block copolypeptide was resuspended at 4° C. in a well containing 30 mL of sodium acetate buffer (pH 5.0) and 4 M urea. In order to remove any aggregated protein contaminant, the resuspended protein solution was centrifuged at 4° C. and 13,000 rpm for 15 minutes. The aggregation and resuspension were repeated 5-10 times until the purity of the block copolypeptide reached about 95%. The purity was measured by sodium dodecyl sulfate-polyacrylamide gel electrophoresis (SDS-PAGE).

For hydroxylation of the tyrosine residue of the block copolypeptide, the block copolypeptide, tyrosinase (~32 kDa) and ORF438 (~15 kDa) were coexpressed as soluble forms.

As a result, the recombinant EBPPI$[G_1A_4F_1]_6$-MFP $[Mgfp5]_1$ diblock copolypeptide was coexpressed in *E. coli* together with tyrosinase and ORF438 by the pET21a vector including the diblock copolypeptide and the pACYC binary vector system including tyrosinase and ORF438.

As seen from FIG. 5 and FIG. 6(A), the tyrosinase and ORF438 genes were identified from the amplified tyrosinase and the ORF438-coded pACYC duet vector.

FIG. 6(B) shows (1) the diblock copolypeptide expressed in the bacteria with pET21 alone, (2) tyrosinase and ORF438 expressed in the bacteria with the pACYC duet vector alone, and (3) the coexpressed diblock copolypeptide of the pET21a vector and tyrosinase and ORF438 of the pACYC duet vector. The number of copies of the plasmid for each vector was higher for the block copolypeptide in the pET vector (~40) than for the pACYC duet vector encoding tyrosinase and ORF438 (~12). That is to say, the block copolypeptide of the pET vector alone was expressed in large quantities as compared to the coexpression system.

FIG. 6(C) shows (1) the EBPPI$[G_1A_4F_1]_6$-MFP$[Mgfp5]_1$-EBPPI$[G_1A_4F_1]_6$ triblock copolypeptide expressed with pET21 alone, and (2) the coexpressed triblock copolypeptide of the pET21a vector and tyrosinase and ORF438 of the pACYC duet vector.

As shown in FIG. 6(E) and FIG. 6(F), the block copolypeptide coexpressed with tyrosinase and ORF438 was stained violet, whereas the control group block copolypeptide expressed alone was stained yellow. It can be seen that the block copolypeptide coexpressed with tyrosinase and ORF438 undergoes hydroxylation.

EXAMPLE 6

Hydroxylation of Tyrosine Residue of EBP-MFP Block Copolypeptide by Mushroom-Derived Tyrosinase The tyrosine residue of the EBP-MFP block copolypeptide was changed to DOPA through modification by mushroom-derived tyrosinase (Sigma Aldrich, T3824) (FIG. 6(D)).

The EBP-MFP block copolypeptide was resuspended in 10 mM phosphate buffer supplemented with 10 mM sodium borate and pH was adjusted to 7.0 using ascorbic acid. Then, mushroom-derived tyrosinase with a final concentration of ~0.01 mg/mL was added. The solution was shaken gently at room temperature (RT) for 3 hours. The tyrosinase-treated EBP-MFP block copolypeptide underwent phase transition at 40° C. as the temperature was raised. In order to remove the tyrosinase, purification was conducted by centrifuging at 40° C. and 16,000 rpm for 10 minutes. The modified block copolypeptide was resupspended in 10 mM phosphate buffer (pH 5) in an ice bath and the sample was centrifuged at 4° C. and 16,000 rpm for 15 minutes to remove insoluble materials.

In particular, the EBP-MFP block copolypeptide was freeze-dried after adding 5% acetic acid (pH 3) in order to prevent autoxidation during the purification. It is because quinone, which is an oxidized form of DOPA, induces intermolecular covalent bonding and reduces interaction with surface molecules under oxidizing conditions.

The EBPPI$[G_1A_4F_1]_6$-MFP$[Mgfp5]_1$ diblock copolypeptide expressed alone in *E. coli* was purified by ITC, and the tyrosine residue of the diblock copolypeptide was changed to DOPA by catalytic reaction by mushroom-derived tyrosinase.

As seen from FIG. 7, the hydroxylated diblock copolypeptide developed violet color upon NBT staining due to hydroxylation of the tyrosine residue. In contrast, unmodified diblock copolypeptide of the control group developed whitish yellow color.

EXAMPLE 7

Characterization of EBP-MFP Block Copolypeptide

The purity and molecular weight of the block copolypeptide were characterized by SDS-PAGE including copper staining. The phase transition behavior of the block copolypeptide was characterized by UV-visible spectrophotometry.

The MFPs with different block lengths were fused with EBPPI and formed self-assembled nanostructures in response to thermal stimulation.

The EBPPI-MFP diblock copolypeptide, the MFP-EBPPI-MFP triblock copolypeptide and the EBPPI-MFP-EBPPI triblock copolypeptide were self-assembled to core-shell nanostructures having a hydrodynamic radius ($R_h$) of 20-40 nm at concentrations of 12.5 μM or higher, whereas the triblock copolypeptides under concentrated conditions formed hydrogels in response to temperature.

FIGS. 8(A) and 8(B) show the copper-stained SDS-PAGE images of the mushroom-derived tyrosinase-catalyzed EBPPI$[G_1A_4F_1]_6$-MFP$[Mgfp5]_1$ diblock copolypeptide and the mushroom-derived tyrosinase-catalyzed EBPPI $[G_1A_4F_1]_6$-MFP$[Mgfp5]_1$-EBPPI$[G_1A_4F_1]_6$ triblock copolypeptide, respectively. The molecular weight of the hydroxylated EBPPI$[G_1A_4F_1]_6$-MFP$[Mgfp5]_1$ diblock copolypeptide is similar to the expectation (~24.6 kDa), and the molecular weight of the hydroxylated EBPPI$[G_1A_4F_1]_6$-MFP$[Mgfp5]_1$-EBPPI$[G_1A_4F_1]_6$ triblock copolypeptide is also similar to the expectation (~40.1 kDa).

The 48.0 kDa and 92.0 kDa hydroxylated EBPPI [G1A4F1]6-MFP[Mgfp5]1 diblock copolypeptides was identified to be in multimerized forms.

Likewise, the hydroxylated EBPPI$[G_1A_4F_1]_6$-MFP $[Mgfp5]_1$-EBPPI$[G_1A_4F_1]_6$ triblock copolypeptide was in multimerized forms with molecular weights of ~80.0 kDa and ~120.0 kDa.

The multimerized form of hydroxylated diblock and triblock copolypeptides are formed in 10 mM phosphate buffer (pH 5.0) due to intermolecular crosslinking by quinone formed through autoxidation of DOPA. This suggests that the block copolypeptides underwent mushroom-derived tyrosinase-catalyzed hydroxylation.

FIG. 8(C) shows the copper-stained SDS-PAGE images of the EBPPI$[G_1A_4F_1]_6$-MFP$[Mgfp5]_1$ diblock copolypeptides and hydroxylated forms thereof, which were treated with the oxidizing agent $NaIO_4$ at different concentrations.

When treated with $NaIO_4$, two tyrosine residues are formed and intermolecular crosslinking occurs between the unmodified EBPPI$[G_1A_4F_1]_6$-MFP$[Mgfp5]_1$ diblock copolypeptides. As a result, the chemically crosslinked diblock copolypeptide remains in the well during SDS-PAGE (lanes (2-3) in FIG. 8(C)).

In contrast, the hydroxylated diblock copolypeptide showed not only the formation of two tyrosine residues at neutral pH but also multimerization due to the formation of quinone induced by autoxidation of DOPA. That is to say, $NaIO_4$ induced intermolecular crosslinking through formation of quinone and two tyrosine residues, and the chemically crosslinked hydroxylated diblock copolypeptide showed no movement during SDS-PAGE.

The thermal characteristics of the EBPPI$[G_1A_4F_1]_6$-MFP $[Mgfp5]_1$ diblock copolypeptide were observed by measuring absorbance at 350 nm in a temperature range from 10° C. to 70° C. while heating at a rate of 1° C./min in 10 mM phosphate buffer (pH 5, for preventing oxidation).

FIG. 9(A) shows the thermal profiles of the control group EBPPI$[G_1A_4F_1]_6$ and the 25 μM EBPPI$[G_1A_4F_1]_6$-MFP $[Mgfp5]_1$ diblock copolypeptides hydroxylated by mushroom-derived tyrosinase or not. The monoblock, EBPPI $[G_1A_4F_1]_6$ showed complete solubility under aquatic conditions below $T_t$ (~45° C.), but showed rapid transition above LOST due to aggregation of EBPPI$[G_1A_4F_1]_6$.

In contrast, the EBPPI$[G_1A_4F_1]_6$-MFP$[Mgfp5]_1$ diblock copolypeptide showed thermal responsivity different from that of the EBPPI monoblock. Because the MFP block makes EBPPI$[G_1A_4F_1]_6$ more hydrophobic, the LOST of the EBPPI$[G_1A_4F_1]_6$-MFP$[Mgfp5]_1$ diblock copolypeptide was decreased to 35° C. regardless of hydroxylation by the mushroom-derived tyrosinase. In addition, the absorbance of the EBPPI$[G_1A_4F_1]_6$-MFP$[Mgfp5]_1$ diblock copolypeptide above the transition temperature shows thermally induced aggregation of the EBPPI block (core) and the water-soluble MFP block (shell), suggesting the formation of the self-assembled nanostructure.

The behavior of LOST depending on the concentrations of the block copolypeptide and the $NaIO_4$ oxidizing agent was analyzed. As a result, the 250 μM hydroxylated EBPPI $[G_1A_4F_1]_6$-MFP$[Mgfp5]_1$ diblock copolypeptide and the 25 μM diblock copolypeptide treated with 10 mM $NaIO_4$ showed rapid transition of the EBP block (FIGS. 9(B) and 9(C)). This is due not only to the formation of quinone induced by DOPA autoxidation and the noncovalent interaction of the MFP block but also to the two tyrosine residues formed at neutral pH. Especially, the aggregation of the MFP block at high concentrations is induced by noncovalent interactions such as hydrogen bonding, π-π stacking, and electrostatic and hydrophobic interactions.

FIG. 9(D) shows the thermal profiles of the 25 μM EBPPI$[G_1A_4F_1]_6$-MFP$[Mgfp5]_1$ diblock copolypeptide and EBPPI$[G_1A_4F_1]_6$-MFP$[Mgfp5]_1$-EBPPI$[G_1A_4F_1]_6$ triblock copolypeptide hydroxylated by mushroom-derived tyrosinase, obtained by measuring absorbance at 350 nm in 10 mM phosphate buffer (pH 5) at a heating rate of 1° C./min. The LOST of the triblock was decreased to 25° C., 10° C. lower than that of the EBPPI$[G_1A_4F_1]_6$-MFP$[Mgfp5]_1$ diblock copolypeptide. It is because the hydrophobic EBPPI blocks were introduced to both ends of the MFP$[Mgfp5]_1$ block. In addition, the thermal responsivity of the triblock copolypeptide is similar to that of the EBPPI$[G_1A_4F_1]_6$-MFP$[Mgfp5]_1$ diblock copolypeptide hydroxylated with 10 mM $NaIO_4$ as shown in FIG. 9(C). The triblock copolypeptide was aggregated at temperatures higher than the LOST of the EBPPI block. It is because the EBPPI block in the diblock and triblock copolypeptides is capable of forming both physical crosslinkages and chemical crosslinkages of MFP through formation of quinone.

EXAMPLE 8

Analysis of Bulk-Scale Surface Adhesiveness of (1) Block Copolypeptide Treated with Mushroom-Derived Tyrosinase and (2) Hydroxylated Block Copolypeptide in Coexpression System In order to test bulk-scale shear strength to an aluminum adherend, the strength of surface adhesion was analyzed depending on the block copolypeptide and the concentration of $NaIO_4$.

Hydroxylated diblock and triblock copolypeptides were prepared by treating with mushroom-derived tyrosinase or in a bacterial coexpression system. First, 10, 20 and 30 wt % of the EBPPI[G1A4F1]6-MFP[Mgfp5]1 diblock copolypeptide was dissolved in 10 mM phosphate buffer (pH 5) containing 10 mM and 100 mM $NaIO_4$. The surface of the adherend was rinsed with acetone, ethanol and water. Each block copolypeptide solution was applied on the adherend and then mixed with 10 mM $NaIO_4$ as an oxidizing agent. The adherend was covered with another adherend and then hardened at 4° C. for 1 hour. The surface adhesivity was compared with the EBPPI$[G_1A_3F_2]_{12}$-EBPP$[A_1G_4I_1]_6$-EBPPI$[G_1A_3F_2]_{12}$ triblock copolypeptide as a control group after hardening in DW at 25° C.

As shown in FIG. 10(B), the 30 wt % diblock copolypeptide treated with 100 mM $NaIO_4$ showed chemical gelation due to quinone-mediated intermolecular crosslinking. However, it showed lower surface adhesiveness than the diblock copolypeptide treated with 10 mM $NaIO_4$ (FIG. 10(C)). This means that the diblock copolypeptide treated with 100 mM $NaIO_4$ underwent more oxidation of DOPA to quinone as compared to that treated with 10 mM $NaIO_4$.

In addition, it was confirmed that the EBPPI$[G_1A_4F_1]_6$-MFP$[Mgfp5]_1$-EBPPI$[G_1A_4F_1]_6$ triblock copolypeptide (10 wt %) treated with 10 mM $NaIO_4$ exhibited stronger surface adhesiveness than the EBPPI$[G_1A_3F_2]_{12}$-EBPP$[G_1A_4F_1]_6$-EBPPI$[G_1A_3F_2]_{12}$ triblock copolypeptide of the control group. It is because the intermediate MFP block has surface adhesiveness (FIG. 11).

In addition, it was confirmed that the surface adhesion strength of the EBPPI$[G_1A_4F_1]_6$-MFP$[Mgfp5]_1$-EBPPI $[G_1A_4F_1]_6$ triblock copolypeptide is superior as compared to the EBPPI$[G_1A_4F_1]_6$-MFP$[Mgfp5]_1$ diblock copolypeptide. This is due to the cohesive force induced by the aggregation of the EBPPI block through physical crosslinking.

EXAMPLE 9

Characterization of Block Copolypeptide Expressed and Purified by Bacterial Coexpression and Investigation of Adhesvity of Hydrogel Hydroxylated block copolypeptides were prepared with various wt % using a bacterial coexpression system. First, 10 wt % of the EBPPI$[G_1A_4F_1]_6$-MFP$[Mgfp5]_1$ diblock copolypeptide was dissolved in 10 mM phosphate buffer (pH 5). Each block copolypeptide solution was mixed with 10-100 mM of the $NaIO_4$ oxidizing agent before being applied on an adherend. After applying each block copolypeptide on the adherend, it was covered with another adherend and hardened at 4° C. for 1 hour.

As shown in FIG. 12(A), 10 wt % of the hydroxylated EBPPI[$G_1A_4F_1$]$_6$-MFP[Mgfp5]$_1$ diblock copolypeptide showed strong bonding between the adherends in the bacterial coexpression system due to surface adhesiveness. In addition, the adherends showed strong adhesiveness in the aquatic environment (FIG. 12(B)).

The adhesivity of 10 wt % of the hydroxylated diblock copolypeptide in the bacterial coexpression system was compared with that of the mushroom-derived tyrosinase-treated diblock copolypeptide. It was confirmed that the hydroxylated block copolypeptide in the bacterial coexpression system exhibited stronger surface adhesivity.

For the hydroxylated diblock or triblock copolypeptide, the degree of hydroxylation of the tyrosine residue is increased coexpression system. Accordingly, it can be seen that stronger surface adhesivity can be achieved when the block copolypeptide is hydroxylated in the bacterial coexpression system. This is also useful in industrial scales.

EXAMPLE 10

Characterization of Core-Shell Structure of Diblock and Triblock Copolypeptides and Investigation of Surface Adhesiveness The characteristics of core-shell structures of EBP-MFP block copolypeptides with or without hydroxyl groups were analyzed by dynamic light scattering (DLS) (Malvern Instruments, Worcestershire, UK). The hydrodynamic radius ($R_h$) of the 12.5 μM block copolypeptide was measured in 10 mM phosphate buffer (pH 5) consecutively for 11 times after equilibrating at 10° C. and 45° C. for 1 minute.

As shown in (c) of FIG. 13(A), the EBPPI[$G_1A_4F_1$]$_6$-MFP[Mgfp5]$_1$ diblock copolypeptide hydroxylated by mushroom-derived tyrosinase had a hydrodynamic radius of 25-30 nm at 10° C. This means that the hydrophobic interaction MFP molecules is increased greatly due to cohesive force and, as a result, a structure compose of an MFP core is formed (FIG. 14(A), FIG. 14(B) and FIG. 14(C)). Also, as shown in (d), the EBPPI[$G_1A_4F_1$]$_6$-MFP[Mgfp5]$_1$ diblock copolypeptide hydroxylated by mushroom-derived tyrosinase had a hydrodynamic radius of 50-60 nm at 45° C. This means that a core-shell structure is formed as the EBP blocks which are soluble below transition temperature form hydrophobic cores above transition temperature through phase transition (FIG. 14(G), FIG. 14(H) and FIG. 14(I)).

In addition, the surface adhesiveness of the core-shell structure of the EBP-MFP block copolypeptide was investigated using a hydrophobic fluorescent dye.

The rhodamine 6G fluorescent dye with a final concentration of 0.5 w/v % was used to investigate the surface adhesiveness of the core-shell structure. The fluorescent dye was (1) placed in a vacant PCR tube (# PCR-02-C, Axygen), (2) mixed with the EBP diblock copolypeptide, (3) mixed with the EBPPI[$G_1A_4F_1$]$_6$-MFP[Mgfp5]$_1$ diblock copolypeptide hydroxylated through coexpression at 10° C., or (4) mixed with the EBPPI[$G_1A_4F_1$]$_6$-MFP[Mgfp5]$_1$ diblock copolypeptide hydroxylated through coexpression at 40° C. Each block copolypeptide was dissolved to 25 μM in 10 mM phosphate buffer (pH5). For (2), (3) and (4), pH was increased to 8 using sodium hydroxide and the mixtures were stabilized at 25° C., 50° C., 10° C. and 40° C., respectively, for 3 hours. Then, all the tubes were washed using distilled water and ethanol.

As shown in FIG. 13(B), only the tube of (4) showed the color of the fluorescent dye. A hydrophobic is formed by the block copolypeptide and the hydrophobic fluorescent dye is bound to the polypeptide core through hydrophobic interaction. For (2), although the fluorescent dye is bound to the EBP block which forms a hydrophobic core, the fluorescent dye is washed off the core-shell structure of the EBP diblock copolypeptide due to lack of surface adhesiveness. For (3), although the fluorescent dye is bound to the MFP block which forms a hydrophobic core, surface adhesiveness is decreased greatly due to the MFP block present in the core and the fluorescent dye is not observed after the washing. For (1), which is for investigating binding due to the nonspecific reaction between the fluorescent dye and the tube during the stabilization, the fluorescent dye was not observed after the washing. For (4), the color of the fluorescent dye was observed even after the washing due to the surface adhesiveness resulting from the interaction between the hydrophobic core of the EBP block formed above the transition temperature and the fluorescent dye.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A multiblock copolypeptide comprising:

an elastin-based polypeptide (EBP); and a mussel foot protein (MFP), wherein the multiblock copolypeptide is composed of an arrangement selected from either $(EBP)_n(MFP)_m(EBP)_n$ or $(MFP)_m(EBP)_n(MFP)_m$, wherein the n is an integer greater than or equal to 1 and less than or equal to 24, the m is an integer greater than or equal to 1 and less than or equal to 12, and each of the elastin-based polypeptide (EBP) comprises an [IPAXG IPAXG IPAXG IPAXG IPAXG IPAXG] block, wherein the X of the [IPAXG IPAXG IPAXG IPAXG IPAXG IPAXG] block comprises: G (Gly), A (Ala) and F (Phe) at a ratio of 1:4:1 or 1:3:2.

2. The multiblock copolypeptide according to claim 1, wherein the mussel foot protein (MFP) is California mussel foot protein 5 (*Mytilus californianus* foot protein 5 (Mcfp5)) or Mediterranean mussel foot protein 5 (*Mytilus galloprovincialis* foot protein 5 (Mgfp5)).

3. The multiblock copolypeptide according to claim 1, wherein the multiblock copolypeptide comprises an amino acid sequence obtained from a nucleic acid sequence of a gene.

4. The multiblock copolypeptide according to claim 1, wherein the multiblock copolypeptide comprises an amino acid sequence obtained using a recombinant vector.

5. The multiblock copolypeptide according to claim 1, wherein the multiblock copolypeptide comprises an amino acid sequence obtained using a recombinant microorganism.

6. The multiblock copolypeptide according to claim 5, wherein the recombinant microorganism comprises a gene encoding tyrosinase or an expression vector comprising a gene encoding tyrosinase.

7. The multiblock copolypeptide according to claim 1, wherein the multiblock copolypeptide is configured to form a self-assembled nanostructure of a core-shell structure , wherein the [IPAXG IPAXG IPAXG IPAXG IPAXG IPAXG] block forms a core structure and the MFP forms a shell structure in response to temperature stimulation.

8. The multiblock copolypeptide according to claim 7, wherein the multiblock copolypeptide is configured to deliver a drug composition via the self-assembled nanostructure.

9. The multiblock copolypeptide according to claim 1, wherein the multiblock copolypeptide is configured to form a hydrogel via crosslinking between block polypeptides of the multiblock copolypeptide in response to temperature stimulation.

10. The multiblock copolypeptide according to claim 9, wherein the hydrogel is formed through oxidation or non-covalent interaction of a DOPA (3,4-dihydroxyphenylalanine) residue comprised in the mussel foot protein (MFP).

11. The multiblock copolypeptide according to claim 1, wherein the multiblock copolypeptide is configured to form a hydrogel that functions as a bioadhesive composition.

12. The multiblock copolypeptide according to claim 1, wherein the multiblock copolypeptide is configured to form a hydrogel that functions as a surgical suture.

13. The multiblock copolypeptide according to claim 1, wherein the multiblock copolypeptide is configured to form crosslinking as to reversibly form a hydrogel in response to a temperature stimulation.

14. The multiblock copolypeptide according to claim 13, wherein the hydrogel exhibits interfacial underwater adhesiveness.

15. A multiblock copolypeptide comprising an arrangement selected from either $(EBP)_n(MFP)_m(EBP)_n$ or $(MFP)_m(EBP)_n(MFP)_m$, wherein EBP is an elastin-based polypeptide;

MFP is a mussel foot protein;

the n is an integer greater than or equal to 1 and less than or equal to 6;

the m is an integer greater than or equal to 1 and less than or equal to 6, and wherein each of the elastin-based polypeptide (EBP) comprises an [IPAXG IPAXG IPAXG IPAXG IPAXG IPAXG] block, and the elastin-based polypeptide (EBP) is configured to form crosslinking such that the multiblock copolypeptide forms a hydrogel in response to a temperature stimulation, and wherein the X of the [IPAXG IPAXG IPAXG IPAXG IPAXG IPAXG] block comprises: G (Gly), A (Ala) and F (Phe) at a ratio of 1:4:1 or 1:3:2.

16. The multiblock copolypeptide according to claim 15, wherein the hydrogel exhibits reversibility in response to a change in temperature.

17. The multiblock copolypeptide according to claim 15, wherein the hydrogel exhibits interfacial underwater adhesiveness.

18. The multiblock copolypeptide according to claim 15, wherein the mussel foot protein (MFP) is California mussel foot protein 5 (*Mytilus californianus* foot protein 5 (Mcfp5)) or Mediterranean mussel foot protein 5 (*Mytilus galloprovincialis* foot protein 5 (Mgfp5)).

19. A multiblock copolypeptide comprising:

an elastin-based polypeptide (EBP); and a mussel foot protein (MFP), wherein the multiblock copolypeptide comprises an amino acid sequence selected from a group consisting of SEQ ID NOS 53 to 70.

* * * * *

SEQUENCE LISTING

```
<160> NUMBER OF SEQ ID NOS: 91

<210> SEQ ID NO 1
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural(EBPE)

<400> SEQUENCE: 1

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly
            20                  25                  30


<210> SEQ ID NO 2
```

```
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural(EBPP)

<400> SEQUENCE: 2

Val Pro Ala Xaa Gly Val Pro Ala Xaa Gly Val Pro Ala Xaa Gly Val
1               5                   10                  15

Pro Ala Xaa Gly Val Pro Ala Xaa Gly Val Pro Ala Xaa Gly
            20                  25                  30


<210> SEQ ID NO 3
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural(EBPPI)

<400> SEQUENCE: 3

Ile Pro Ala Xaa Gly Ile Pro Ala Xaa Gly Ile Pro Ala Xaa Gly Ile
1               5                   10                  15

Pro Ala Xaa Gly Ile Pro Ala Xaa Gly Ile Pro Ala Xaa Gly
            20                  25                  30


<210> SEQ ID NO 4
<211> LENGTH: 90
<212> TYPE: DNA
<213> ORGANISM: Artificial Sequence
<220> FEATURE:
<223> OTHER INFORMATION: EBPE[A1G4I1]

<400> SEQUENCE: 4

gtcccaggtg gaggtgtacc cggcgcgggt gtcccaggtg gaggtgtacc tgggggtggg     60

gtccctggta ttggcgtacc tggaggcggc                                      90


<210> SEQ ID NO 5
<211> LENGTH: 90
<212> TYPE: DNA
<213> ORGANISM: Artificial Sequence
<220> FEATURE:
<223> OTHER INFORMATION: EBPP[A1G4I1]

<400> SEQUENCE: 5

gttccagctg gcggtgtacc tgctgctgct gttccggccg gtggtgttcc ggcgggcggc     60

gtgcctgcaa taggagttcc cgctggtggc                                      90


<210> SEQ ID NO 6
<211> LENGTH: 90
<212> TYPE: DNA
<213> ORGANISM: Artificial Sequence
<220> FEATURE:
<223> OTHER INFORMATION: EBPE[K1G4I1]

<400> SEQUENCE: 6

gttccgggtg gtggtgttcc gggtaaaggt gttccgggtg gtggtgttcc gggtggtggt     60

ggtgttccgg gtatcggtgt tccgggtggc                                      90


<210> SEQ ID NO 7
<211> LENGTH: 90
<212> TYPE: DNA
<213> ORGANISM: Artificial Sequence
```

```
<220> FEATURE:
<223> OTHER INFORMATION: EBPP[K1G4I1]

<400> SEQUENCE: 7

gttccggcgg gtggtgttcc ggcgaaaggt gttccggcgg gtggtgttcc ggcgggtggt     60

gttccggcga tcggtgttcc ggcgggtggc                                      90


<210> SEQ ID NO 8
<211> LENGTH: 90
<212> TYPE: DNA
<213> ORGANISM: Artificial Sequence
<220> FEATURE:
<223> OTHER INFORMATION: EBPE[D1G4I1]

<400> SEQUENCE: 8

gttccgggtg gtggtgttcc gggtgatggt gttccgggtg gtggtgttcc gggtggtggt     60

ggtgttccgg gtatcggtgt tccgggtggc                                      90


<210> SEQ ID NO 9
<211> LENGTH: 90
<212> TYPE: DNA
<213> ORGANISM: Artificial Sequence
<220> FEATURE:
<223> OTHER INFORMATION: EBPP[D1G4I1]

<400> SEQUENCE: 9

gttccggcgg gtggtgttcc ggcggatggt gttccggcgg gtggtgttcc ggcgggtggt     60

gttccggcga tcggtgttcc ggcgggtggc                                      90


<210> SEQ ID NO 10
<211> LENGTH: 90
<212> TYPE: DNA
<213> ORGANISM: Artificial Sequence
<220> FEATURE:
<223> OTHER INFORMATION: EBPE[E1G4I1]

<400> SEQUENCE: 10

gttccgggtg gtggtgttcc gggtgaaggt gttccgggtg gtggtgttcc gggtggtggt     60

ggtgttccgg gtatcggtgt tccgggtggc                                      90


<210> SEQ ID NO 11
<211> LENGTH: 90
<212> TYPE: DNA
<213> ORGANISM: Artificial Sequence
<220> FEATURE:
<223> OTHER INFORMATION: EBPP[E1G4I1]

<400> SEQUENCE: 11

gttccggcgg gtggtgttcc ggcggaaggt gttccggcgg gtggtgttcc ggcgggtggt     60

gttccggcga tcggtgttcc ggcgggtggc                                      90


<210> SEQ ID NO 12
<211> LENGTH: 90
<212> TYPE: DNA
<213> ORGANISM: Artificial Sequence
<220> FEATURE:
<223> OTHER INFORMATION: EBPE[G1A3F2]

<400> SEQUENCE: 12

gtcccgggtg cgggcgtgcc gggatttgga gttccgggtg cgggtgttcc aggcggtggt     60

gttccgggcg cgggcgtgcc gggctttggc                                      90
```

<210> SEQ ID NO 13
<211> LENGTH: 90
<212> TYPE: DNA
<213> ORGANISM: Artificial Sequence
<220> FEATURE:
<223> OTHER INFORMATION: EBPP[G1A3F2]

<400> SEQUENCE: 13
gtgccggcgg cgggcgttcc agcctttggt gtgccagcgg cgggagttcc ggccggtggc 60
gtgccggcag cgggcgtgcc ggcttttggc 90

<210> SEQ ID NO 14
<211> LENGTH: 90
<212> TYPE: DNA
<213> ORGANISM: Artificial Sequence
<220> FEATURE:
<223> OTHER INFORMATION: EBPP[K1A3F2]

<400> SEQUENCE: 14
gtgccggcgg cgggcgttcc agcctttggt gtgccagcgg cgggagttcc ggccaaaggc 60
gtgccggcag cgggcgtgcc ggcttttggc 90

<210> SEQ ID NO 15
<211> LENGTH: 90
<212> TYPE: DNA
<213> ORGANISM: Artificial Sequence
<220> FEATURE:
<223> OTHER INFORMATION: EBPP[D1A3F2]

<400> SEQUENCE: 15
gtgccggcgg cgggcgttcc agcctttggt gtgccagcgg cgggagttcc ggccgatggc 60
gtgccggcag cgggcgtgcc ggcttttggc 90

<210> SEQ ID NO 16
<211> LENGTH: 90
<212> TYPE: DNA
<213> ORGANISM: Artificial Sequence
<220> FEATURE:
<223> OTHER INFORMATION: EBPP[K3F3]

<400> SEQUENCE: 16
gttccagcgt ttggcgtgcc agcgaaaggt gttccggcgt ttggggttcc cgcgaaaggt 60
gtgccggcct ttggtgtgcc ggccaaaggc 90

<210> SEQ ID NO 17
<211> LENGTH: 90
<212> TYPE: DNA
<213> ORGANISM: Artificial Sequence
<220> FEATURE:
<223> OTHER INFORMATION: EBPP[D3F3]

<400> SEQUENCE: 17
gttccagcgt ttggcgtgcc agcggatggt gttccggcgt ttggggttcc cgcggatggt 60
gtgccggcct ttggtgtgcc ggccgatggc 90

<210> SEQ ID NO 18
<211> LENGTH: 90
<212> TYPE: DNA
<213> ORGANISM: Artificial Sequence
<220> FEATURE:
<223> OTHER INFORMATION: EBPP[H3A3I1]

<400> SEQUENCE: 18
gtgccggcgc atggagttcc tgccgccggt gttcctgcgc atggtgtacc ggcaattggc 60
gttccggcac atggtgtgcc ggccgccggc 90

<210> SEQ ID NO 19
<211> LENGTH: 90
<212> TYPE: DNA
<213> ORGANISM: Artificial Sequence
<220> FEATURE:
<223> OTHER INFORMATION: EBPP[H5G1]

<400> SEQUENCE: 19
gttccggccg gaggtgtacc ggcgcatggt gttccggcac atggtgtgcc ggctcacggt 60
gtgcctgcgc atggcgttcc tgcgcatggc 90

<210> SEQ ID NO 20
<211> LENGTH: 90
<212> TYPE: DNA
<213> ORGANISM: Artificial Sequence
<220> FEATURE:
<223> OTHER INFORMATION: EBPP[G1C3F2]

<400> SEQUENCE: 20
gtgccggcgt gcggcgttcc agcctttggt gtgccagcgt gcggagttcc ggccggtggc 60
gtgccggcat gcggcgtgcc ggcttttggc 90

<210> SEQ ID NO 21
<211> LENGTH: 90
<212> TYPE: DNA
<213> ORGANISM: Artificial Sequence
<220> FEATURE:
<223> OTHER INFORMATION: EBPPI[G1A4F1]

<400> SEQUENCE: 21
attcctgcag ccggtatccc ggccggtggc attccggcag ccggcattcc ggccgccggc 60
atcccggcat ttggcattcc tgcagcaggc 90

<210> SEQ ID NO 22
<211> LENGTH: 90
<212> TYPE: DNA
<213> ORGANISM: Artificial Sequence
<220> FEATURE:
<223> OTHER INFORMATION: EBPPI[G1A3F2]

<400> SEQUENCE: 22
attccggccg caggcattcc tgcatttggt attccggcgg caggcattcc tgccggtggc 60
atcccggcag cgggcattcc ggcctttggc 90

<210> SEQ ID NO 23
<211> LENGTH: 30
<212> TYPE: PRT
<213> ORGANISM: Artificial Sequence
<220> FEATURE:
<223> OTHER INFORMATION: EBPE[A1G4I1]

<400> SEQUENCE: 23

```
Val Pro Gly Gly Gly Val Pro Gly Ala Gly Val Pro Gly Gly Gly Val
1               5                   10                  15

Pro Gly Gly Gly Val Pro Gly Ile Gly Val Pro Gly Gly Gly
            20                  25                  30
```

<210> SEQ ID NO 24

<211> LENGTH: 30
<212> TYPE: PRT
<213> ORGANISM: Artificial Sequence
<220> FEATURE:
<223> OTHER INFORMATION: EBPP[A1G4I1]

<400> SEQUENCE: 24

Val Pro Ala Gly Gly Val Pro Ala Ala Gly Val Pro Ala Gly Gly Val
1 5 10 15

Pro Ala Gly Gly Val Pro Ala Ile Gly Val Pro Ala Gly Gly
20 25 30

<210> SEQ ID NO 25
<211> LENGTH: 30
<212> TYPE: PRT
<213> ORGANISM: Artificial Sequence
<220> FEATURE:
<223> OTHER INFORMATION: EBPE[K1G4I1]

<400> SEQUENCE: 25

Val Pro Gly Gly Gly Val Pro Gly Lys Gly Val Pro Gly Gly Gly Val
1 5 10 15

Pro Gly Gly Gly Val Pro Gly Ile Gly Val Pro Gly Gly Gly
20 25 30

<210> SEQ ID NO 26
<211> LENGTH: 30
<212> TYPE: PRT
<213> ORGANISM: Artificial Sequence
<220> FEATURE:
<223> OTHER INFORMATION: EBPP[K1G4I1]

<400> SEQUENCE: 26

Val Pro Ala Gly Gly Val Pro Ala Lys Gly Val Pro Ala Gly Gly Val
1 5 10 15

Pro Ala Gly Gly Val Pro Ala Ile Gly Val Pro Ala Gly Gly
20 25 30

<210> SEQ ID NO 27
<211> LENGTH: 30
<212> TYPE: PRT
<213> ORGANISM: Artificial Sequence
<220> FEATURE:
<223> OTHER INFORMATION: EBPE[D1G4I1]

<400> SEQUENCE: 27

Val Pro Gly Gly Gly Val Pro Gly Asp Gly Val Pro Gly Gly Gly Val
1 5 10 15

Pro Gly Gly Gly Val Pro Gly Ile Gly Val Pro Gly Gly Gly
20 25 30

<210> SEQ ID NO 28
<211> LENGTH: 30
<212> TYPE: PRT
<213> ORGANISM: Artificial Sequence
<220> FEATURE:
<223> OTHER INFORMATION: EBPP[D1G4I1]

<400> SEQUENCE: 28

Val Pro Ala Gly Gly Val Pro Ala Asp Gly Val Pro Ala Gly Gly Val
1 5 10 15

Pro Ala Gly Gly Val Pro Ala Ile Gly Val Pro Ala Gly Gly
20 25 30

<210> SEQ ID NO 29
<211> LENGTH: 30
<212> TYPE: PRT
<213> ORGANISM: Artificial Sequence
<220> FEATURE:
<223> OTHER INFORMATION: EBPE[E1G4I1]

<400> SEQUENCE: 29

```
Val Pro Gly Gly Gly Val Pro Gly Glu Gly Val Pro Gly Gly Gly Val
1               5                   10                  15

Pro Gly Gly Gly Val Pro Gly Ile Gly Val Pro Gly Gly Gly
            20                  25                  30
```

<210> SEQ ID NO 30
<211> LENGTH: 30
<212> TYPE: PRT
<213> ORGANISM: Artificial Sequence
<220> FEATURE:
<223> OTHER INFORMATION: EBPP[E1G4I1]

<400> SEQUENCE: 30

```
Val Pro Ala Gly Gly Val Pro Ala Glu Gly Val Pro Ala Gly Gly Val
1               5                   10                  15

Pro Ala Gly Gly Val Pro Ala Ile Gly Val Pro Ala Gly Gly
            20                  25                  30
```

<210> SEQ ID NO 31
<211> LENGTH: 30
<212> TYPE: PRT
<213> ORGANISM: Artificial Sequence
<220> FEATURE:
<223> OTHER INFORMATION: EBPE[G1A3F2]

<400> SEQUENCE: 31

```
Val Pro Gly Ala Gly Val Pro Gly Phe Gly Val Pro Gly Ala Gly Val
1               5                   10                  15

Pro Gly Gly Gly Val Pro Gly Ala Gly Val Pro Gly Phe Gly
            20                  25                  30
```

<210> SEQ ID NO 32
<211> LENGTH: 30
<212> TYPE: PRT
<213> ORGANISM: Artificial Sequence
<220> FEATURE:
<223> OTHER INFORMATION: EBPP[G1A3F2]

<400> SEQUENCE: 32

```
Val Pro Ala Ala Gly Val Pro Ala Phe Gly Val Pro Ala Ala Gly Val
1               5                   10                  15

Pro Ala Gly Gly Val Pro Ala Ala Gly Val Pro Ala Phe Gly
            20                  25                  30
```

<210> SEQ ID NO 33
<211> LENGTH: 30
<212> TYPE: PRT
<213> ORGANISM: Artificial Sequence
<220> FEATURE:
<223> OTHER INFORMATION: EBPP[K1A3F2]

<400> SEQUENCE: 33

```
Val Pro Ala Ala Gly Val Pro Ala Phe Gly Val Pro Ala Ala Gly Val
1               5                   10                  15

Pro Ala Gly Gly Val Pro Ala Ala Gly Val Pro Ala Phe Gly
            20                  25                  30
```

<210> SEQ ID NO 34
<211> LENGTH: 30
<212> TYPE: PRT
<213> ORGANISM: Artificial Sequence
<220> FEATURE:
<223> OTHER INFORMATION: EBPP[D1A3F2]

<400> SEQUENCE: 34

Val Pro Ala Ala Gly Val Pro Ala Phe Gly Val Pro Ala Ala Gly Val
1 5 10 15

Pro Ala Gly Gly Val Pro Ala Ala Gly Val Pro Ala Phe Gly
20 25 30

<210> SEQ ID NO 35
<211> LENGTH: 30
<212> TYPE: PRT
<213> ORGANISM: Artificial Sequence
<220> FEATURE:
<223> OTHER INFORMATION: EBPP[K3F3]

<400> SEQUENCE: 35

Val Pro Ala Phe Gly Val Pro Ala Lys Gly Val Pro Ala Phe Gly Val
1 5 10 15

Pro Ala Lys Gly Val Pro Ala Phe Gly Val Pro Ala Lys Gly
20 25 30

<210> SEQ ID NO 36
<211> LENGTH: 30
<212> TYPE: PRT
<213> ORGANISM: Artificial Sequence
<220> FEATURE:
<223> OTHER INFORMATION: EBPP[D3F3]

<400> SEQUENCE: 36

Val Pro Ala Phe Gly Val Pro Ala Asp Gly Val Pro Ala Phe Gly Val
1 5 10 15

Pro Ala Asp Gly Val Pro Ala Phe Gly Val Pro Ala Asp Gly
20 25 30

<210> SEQ ID NO 37
<211> LENGTH: 30
<212> TYPE: PRT
<213> ORGANISM: Artificial Sequence
<220> FEATURE:
<223> OTHER INFORMATION: EBPP[H3A3I1]

<400> SEQUENCE: 37

Val Pro Ala His Gly Val Pro Ala Ala Gly Val Pro Ala His Gly Val
1 5 10 15

Pro Ala Ile Gly Val Pro Ala His Gly Val Pro Ala Ala Gly
20 25 30

<210> SEQ ID NO 38
<211> LENGTH: 30
<212> TYPE: PRT
<213> ORGANISM: Artificial Sequence
<220> FEATURE:
<223> OTHER INFORMATION: EBPP[H5G1]

<400> SEQUENCE: 38

Val Pro Ala Gly Gly Val Pro Ala His Gly Val Pro Ala His Gly Val
1 5 10 15

Pro Ala His Gly Val Pro Ala His Gly Val Pro Ala His Gly
20 25 30

<210> SEQ ID NO 39
<211> LENGTH: 30
<212> TYPE: PRT
<213> ORGANISM: Artificial Sequence
<220> FEATURE:
<223> OTHER INFORMATION: EBPP[G1C3F2]

<400> SEQUENCE: 39

```
Val Pro Ala Cys Gly Val Pro Ala Phe Gly Val Pro Ala Cys Gly Val
1               5                   10                  15

Pro Ala Gly Gly Val Pro Ala Cys Gly Val Pro Ala Phe Gly
            20                  25                  30
```

<210> SEQ ID NO 40
<211> LENGTH: 30
<212> TYPE: PRT
<213> ORGANISM: Artificial Sequence
<220> FEATURE:
<223> OTHER INFORMATION: EBPPI[G1A4F1]

<400> SEQUENCE: 40

```
Ile Pro Ala Ala Gly Ile Pro Ala Gly Gly Ile Pro Ala Ala Gly Ile
1               5                   10                  15

Pro Ala Ala Gly Ile Pro Ala Phe Gly Ile Pro Ala Ala Gly
            20                  25                  30
```

<210> SEQ ID NO 41
<211> LENGTH: 30
<212> TYPE: PRT
<213> ORGANISM: Artificial Sequence
<220> FEATURE:
<223> OTHER INFORMATION: EBPPI[G1A3F2]

<400> SEQUENCE: 41

```
Ile Pro Ala Ala Gly Ile Pro Ala Phe Gly Ile Pro Ala Ala Gly Ile
1               5                   10                  15

Pro Ala Gly Gly Ile Pro Ala Ala Gly Ile Pro Ala Phe Gly
            20                  25                  30
```

<210> SEQ ID NO 42
<211> LENGTH: 228
<212> TYPE: DNA
<213> ORGANISM: Artificial Sequence
<220> FEATURE:
<223> OTHER INFORMATION: MFP[Mgfp5]

<400> SEQUENCE: 42

```
tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcg                 228
```

<210> SEQ ID NO 43
<211> LENGTH: 228
<212> TYPE: DNA
<213> ORGANISM: Artificial Sequence
<220> FEATURE:
<223> OTHER INFORMATION: MFP[Mcfp5]

<400> SEQUENCE: 43

```
gtgggtagcg gctatgacgg ctattcagat ggctactatc ctggtagtgc atataactac     60
```

ccgtcagggt cccatggcta ccatggtcat ggctataaag gcaaatacta tggcaaaggc 120
aaaaaatatt actataaata taaacgcacc ggcaagtata aatatctgaa aaaagcgcgc 180
aaatatcatc gcaagggcta taaaaaatac tatggtggcg gctccagt 228

<210> SEQ ID NO 44
<211> LENGTH: 76
<212> TYPE: PRT
<213> ORGANISM: Artificial Sequence
<220> FEATURE:
<223> OTHER INFORMATION: MFP[Mgfp5]

<400> SEQUENCE: 44

Ser Ser Glu Glu Tyr Lys Gly Gly Tyr Tyr Pro Gly Asn Thr Tyr His
1 5 10 15

Tyr His Ser Gly Gly Ser Tyr His Gly Ser Gly Tyr His Gly Gly Tyr
20 25 30

Lys Gly Lys Tyr Tyr Gly Lys Ala Lys Lys Tyr Tyr Tyr Lys Tyr Lys
35 40 45

Asn Ser Gly Lys Tyr Lys Tyr Leu Lys Lys Ala Arg Lys Tyr His Arg
50 55 60

Lys Gly Tyr Lys Lys Tyr Tyr Gly Gly Gly Ser Ser
65 70 75

<210> SEQ ID NO 45
<211> LENGTH: 76
<212> TYPE: PRT
<213> ORGANISM: Artificial Sequence
<220> FEATURE:
<223> OTHER INFORMATION: MFP[Mcfp5]

<400> SEQUENCE: 45

Val Gly Ser Gly Tyr Asp Gly Tyr Ser Asp Gly Tyr Tyr Pro Gly Ser
1 5 10 15

Ala Tyr Asn Tyr Pro Ser Gly Ser His Gly Tyr His Gly His His Tyr
20 25 30

Lys Gly Lys Tyr Tyr Gly Lys Gly Lys Lys Tyr Tyr Tyr Lys Tyr Lys
35 40 45

Arg Thr Gly Lys Tyr Lys Tyr Leu Lys Lys Ala Arg Lys Tyr His Arg
50 55 60

Lys Gly Tyr Lys Lys Tyr Tyr Gly Gly Gly Ser Ser
65 70 75

<210> SEQ ID NO 46
<211> LENGTH: 28
<212> TYPE: DNA
<213> ORGANISM: Artificial Sequence
<220> FEATURE:
<223> OTHER INFORMATION: pSA-tyr-5p primer

<400> SEQUENCE: 46
ggaggatccg accgtccgca agaaccag 28

<210> SEQ ID NO 47
<211> LENGTH: 30
<212> TYPE: DNA
<213> ORGANISM: Artificial Sequence
<220> FEATURE:
<223> OTHER INFORMATION: pSA-tyr-3' primer

<400> SEQUENCE: 47
ggaaagcttg acgtcgaagg tgtagtgccg 30

<210> SEQ ID NO 48
<211> LENGTH: 28
<212> TYPE: DNA
<213> ORGANISM: Artificial Sequence
<220> FEATURE:
<223> OTHER INFORMATION: pSA-438-5' primer

<400> SEQUENCE: 48
cacgatatcg ccggaactca cccgtcgt 28

<210> SEQ ID NO 49
<211> LENGTH: 30
<212> TYPE: DNA
<213> ORGANISM: Artificial Sequence
<220> FEATURE:
<223> OTHER INFORMATION: pSA-438-3' primer

<400> SEQUENCE: 49
caagttaccg ttggagggga aggggaggag 30

<210> SEQ ID NO 50
<211> LENGTH: 796
<212> TYPE: PRT
<213> ORGANISM: Artificial Sequence
<220> FEATURE:
<223> OTHER INFORMATION: MFP[Mgfp5]1-EBPP[G1A3F2]24

<400> SEQUENCE: 50

```
Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Val Pro Ala Ala
65                  70                  75                  80

Gly Val Pro Ala Phe Gly Val Pro Ala Ala Gly Val Pro Ala Gly Gly
                85                  90                  95

Val Pro Ala Ala Gly Val Pro Ala Phe Gly Val Pro Ala Ala Gly Val
            100                 105                 110

Pro Ala Phe Gly Val Pro Ala Ala Gly Val Pro Ala Gly Gly Val Pro
        115                 120                 125

Ala Ala Gly Val Pro Ala Phe Gly Val Pro Ala Ala Gly Val Pro Ala
    130                 135                 140

Phe Gly Val Pro Ala Ala Gly Val Pro Ala Gly Gly Val Pro Ala Ala
145                 150                 155                 160

Gly Val Pro Ala Phe Gly Val Pro Ala Ala Gly Val Pro Ala Phe Gly
                165                 170                 175

Val Pro Ala Ala Gly Val Pro Ala Gly Gly Val Pro Ala Ala Gly Val
            180                 185                 190

Pro Ala Phe Gly Val Pro Ala Ala Gly Val Pro Ala Phe Gly Val Pro
        195                 200                 205

Ala Ala Gly Val Pro Ala Gly Gly Val Pro Ala Ala Gly Val Pro Ala
    210                 215                 220

Phe Gly Val Pro Ala Ala Gly Val Pro Ala Phe Gly Val Pro Ala Ala
225                 230                 235                 240
```

```
Gly Val Pro Ala Gly Gly Val Pro Ala Ala Gly Val Pro Ala Phe Gly
                245                 250                 255

Val Pro Ala Ala Gly Val Pro Ala Phe Gly Val Pro Ala Ala Gly Val
            260                 265                 270

Pro Ala Gly Gly Val Pro Ala Ala Gly Val Pro Ala Phe Gly Val Pro
        275                 280                 285

Ala Ala Gly Val Pro Ala Phe Gly Val Pro Ala Ala Gly Val Pro Ala
    290                 295                 300

Gly Gly Val Pro Ala Ala Gly Val Pro Ala Phe Gly Val Pro Ala Ala
305                 310                 315                 320

Gly Val Pro Ala Phe Gly Val Pro Ala Ala Gly Val Pro Ala Gly Gly
                325                 330                 335

Val Pro Ala Ala Gly Val Pro Ala Phe Gly Val Pro Ala Ala Gly Val
            340                 345                 350

Pro Ala Phe Gly Val Pro Ala Ala Gly Val Pro Ala Gly Gly Val Pro
        355                 360                 365

Ala Ala Gly Val Pro Ala Phe Gly Val Pro Ala Ala Gly Val Pro Ala
    370                 375                 380

Phe Gly Val Pro Ala Ala Gly Val Pro Ala Gly Gly Val Pro Ala Ala
385                 390                 395                 400

Gly Val Pro Ala Phe Gly Val Pro Ala Ala Gly Val Pro Ala Phe Gly
                405                 410                 415

Val Pro Ala Ala Gly Val Pro Ala Gly Gly Val Pro Ala Ala Gly Val
            420                 425                 430

Pro Ala Phe Gly Val Pro Ala Ala Gly Val Pro Ala Phe Gly Val Pro
        435                 440                 445

Ala Ala Gly Val Pro Ala Gly Gly Val Pro Ala Ala Gly Val Pro Ala
    450                 455                 460

Phe Gly Val Pro Ala Ala Gly Val Pro Ala Phe Gly Val Pro Ala Ala
465                 470                 475                 480

Gly Val Pro Ala Gly Gly Val Pro Ala Ala Gly Val Pro Ala Phe Gly
                485                 490                 495

Val Pro Ala Ala Gly Val Pro Ala Phe Gly Val Pro Ala Ala Gly Val
            500                 505                 510

Pro Ala Gly Gly Val Pro Ala Ala Gly Val Pro Ala Phe Gly Val Pro
        515                 520                 525

Ala Ala Gly Val Pro Ala Phe Gly Val Pro Ala Ala Gly Val Pro Ala
    530                 535                 540

Gly Gly Val Pro Ala Ala Gly Val Pro Ala Phe Gly Val Pro Ala Ala
545                 550                 555                 560

Gly Val Pro Ala Phe Gly Val Pro Ala Ala Gly Val Pro Ala Gly Gly
                565                 570                 575

Val Pro Ala Ala Gly Val Pro Ala Phe Gly Val Pro Ala Ala Gly Val
            580                 585                 590

Pro Ala Phe Gly Val Pro Ala Ala Gly Val Pro Ala Gly Gly Val Pro
        595                 600                 605

Ala Ala Gly Val Pro Ala Phe Gly Val Pro Ala Ala Gly Val Pro Ala
    610                 615                 620

Phe Gly Val Pro Ala Ala Gly Val Pro Ala Gly Gly Val Pro Ala Ala
625                 630                 635                 640

Gly Val Pro Ala Phe Gly Val Pro Ala Ala Gly Val Pro Ala Phe Gly
                645                 650                 655
```

```
Val Pro Ala Ala Gly Val Pro Ala Gly Gly Val Pro Ala Ala Gly Val
            660                 665                 670

Pro Ala Phe Gly Val Pro Ala Ala Gly Val Pro Ala Phe Gly Val Pro
        675                 680                 685

Ala Ala Gly Val Pro Ala Gly Gly Val Pro Ala Ala Gly Val Pro Ala
    690                 695                 700

Phe Gly Val Pro Ala Ala Gly Val Pro Ala Phe Gly Val Pro Ala Ala
705                 710                 715                 720

Gly Val Pro Ala Gly Gly Val Pro Ala Ala Gly Val Pro Ala Phe Gly
                725                 730                 735

Val Pro Ala Ala Gly Val Pro Ala Phe Gly Val Pro Ala Ala Gly Val
            740                 745                 750

Pro Ala Gly Gly Val Pro Ala Ala Gly Val Pro Ala Phe Gly Val Pro
        755                 760                 765

Ala Ala Gly Val Pro Ala Phe Gly Val Pro Ala Ala Gly Val Pro Ala
    770                 775                 780

Gly Gly Val Pro Ala Ala Gly Val Pro Ala Phe Gly
785                 790                 795


<210> SEQ ID NO 51
<211> LENGTH: 872
<212> TYPE: PRT
<213> ORGANISM: Artificial Sequence
<220> FEATURE:
<223> OTHER INFORMATION: MFP[Mgfp5]2-EBPP[G1A3F2]24

<400> SEQUENCE: 51

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Val Pro Ala Ala Gly Val Pro Ala
145                 150                 155                 160

Phe Gly Val Pro Ala Ala Gly Val Pro Ala Gly Gly Val Pro Ala Ala
                165                 170                 175

Gly Val Pro Ala Phe Gly Val Pro Ala Ala Gly Val Pro Ala Phe Gly
            180                 185                 190

Val Pro Ala Ala Gly Val Pro Ala Gly Gly Val Pro Ala Ala Gly Val
        195                 200                 205

Pro Ala Phe Gly Val Pro Ala Ala Gly Val Pro Ala Phe Gly Val Pro
    210                 215                 220
```

```
Ala Ala Gly Val Pro Ala Gly Gly Val Pro Ala Ala Gly Val Pro Ala
225                 230                 235                 240

Phe Gly Val Pro Ala Ala Gly Val Pro Ala Phe Gly Val Pro Ala Ala
                245                 250                 255

Gly Val Pro Ala Gly Gly Val Pro Ala Ala Gly Val Pro Ala Phe Gly
            260                 265                 270

Val Pro Ala Ala Gly Val Pro Ala Phe Gly Val Pro Ala Ala Gly Val
        275                 280                 285

Pro Ala Gly Gly Val Pro Ala Ala Gly Val Pro Ala Phe Gly Val Pro
    290                 295                 300

Ala Ala Gly Val Pro Ala Phe Gly Val Pro Ala Ala Gly Val Pro Ala
305                 310                 315                 320

Gly Gly Val Pro Ala Ala Gly Val Pro Ala Phe Gly Val Pro Ala Ala
                325                 330                 335

Gly Val Pro Ala Phe Gly Val Pro Ala Ala Gly Val Pro Ala Gly Gly
            340                 345                 350

Val Pro Ala Ala Gly Val Pro Ala Phe Gly Val Pro Ala Ala Gly Val
        355                 360                 365

Pro Ala Phe Gly Val Pro Ala Ala Gly Val Pro Ala Gly Gly Val Pro
    370                 375                 380

Ala Ala Gly Val Pro Ala Phe Gly Val Pro Ala Ala Gly Val Pro Ala
385                 390                 395                 400

Phe Gly Val Pro Ala Ala Gly Val Pro Ala Gly Gly Val Pro Ala Ala
                405                 410                 415

Gly Val Pro Ala Phe Gly Val Pro Ala Ala Gly Val Pro Ala Phe Gly
            420                 425                 430

Val Pro Ala Ala Gly Val Pro Ala Gly Gly Val Pro Ala Ala Gly Val
        435                 440                 445

Pro Ala Phe Gly Val Pro Ala Ala Gly Val Pro Ala Phe Gly Val Pro
    450                 455                 460

Ala Ala Gly Val Pro Ala Gly Gly Val Pro Ala Ala Gly Val Pro Ala
465                 470                 475                 480

Phe Gly Val Pro Ala Ala Gly Val Pro Ala Phe Gly Val Pro Ala Ala
                485                 490                 495

Gly Val Pro Ala Gly Gly Val Pro Ala Ala Gly Val Pro Ala Phe Gly
            500                 505                 510

Val Pro Ala Ala Gly Val Pro Ala Phe Gly Val Pro Ala Ala Gly Val
        515                 520                 525

Pro Ala Gly Gly Val Pro Ala Ala Gly Val Pro Ala Phe Gly Val Pro
    530                 535                 540

Ala Ala Gly Val Pro Ala Phe Gly Val Pro Ala Ala Gly Val Pro Ala
545                 550                 555                 560

Gly Gly Val Pro Ala Ala Gly Val Pro Ala Phe Gly Val Pro Ala Ala
                565                 570                 575

Gly Val Pro Ala Phe Gly Val Pro Ala Ala Gly Val Pro Ala Gly Gly
            580                 585                 590

Val Pro Ala Ala Gly Val Pro Ala Phe Gly Val Pro Ala Ala Gly Val
        595                 600                 605

Pro Ala Phe Gly Val Pro Ala Ala Gly Val Pro Ala Gly Gly Val Pro
    610                 615                 620

Ala Ala Gly Val Pro Ala Phe Gly Val Pro Ala Ala Gly Val Pro Ala
625                 630                 635                 640

Phe Gly Val Pro Ala Ala Gly Val Pro Ala Gly Gly Val Pro Ala Ala
```

```
                645                 650                 655

Gly Val Pro Ala Phe Gly Val Pro Ala Ala Gly Val Pro Ala Phe Gly
            660                 665                 670

Val Pro Ala Ala Gly Val Pro Ala Gly Gly Val Pro Ala Ala Gly Val
        675                 680                 685

Pro Ala Phe Gly Val Pro Ala Ala Gly Val Pro Ala Phe Gly Val Pro
    690                 695                 700

Ala Ala Gly Val Pro Ala Gly Gly Val Pro Ala Ala Gly Val Pro Ala
705                 710                 715                 720

Phe Gly Val Pro Ala Ala Gly Val Pro Ala Phe Gly Val Pro Ala Ala
                725                 730                 735

Gly Val Pro Ala Gly Gly Val Pro Ala Ala Gly Val Pro Ala Phe Gly
            740                 745                 750

Val Pro Ala Ala Gly Val Pro Ala Phe Gly Val Pro Ala Ala Gly Val
        755                 760                 765

Pro Ala Gly Gly Val Pro Ala Ala Gly Val Pro Ala Phe Gly Val Pro
    770                 775                 780

Ala Ala Gly Val Pro Ala Phe Gly Val Pro Ala Ala Gly Val Pro Ala
785                 790                 795                 800

Gly Gly Val Pro Ala Ala Gly Val Pro Ala Phe Gly Val Pro Ala Ala
                805                 810                 815

Gly Val Pro Ala Phe Gly Val Pro Ala Ala Gly Val Pro Ala Gly Gly
            820                 825                 830

Val Pro Ala Ala Gly Val Pro Ala Phe Gly Val Pro Ala Ala Gly Val
        835                 840                 845

Pro Ala Phe Gly Val Pro Ala Ala Gly Val Pro Ala Gly Gly Val Pro
    850                 855                 860

Ala Ala Gly Val Pro Ala Phe Gly
865                 870


<210> SEQ ID NO 52
<211> LENGTH: 1024
<212> TYPE: PRT
<213> ORGANISM: Artificial Sequence
<220> FEATURE:
<223> OTHER INFORMATION: MFP[Mgfp5]4-EBPP[G1A3F2]24

<400> SEQUENCE: 52

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
```

```
    130                 135                 140

Lys Tyr Tyr Gly Gly Gly Ser Ser Ser Ser Glu Glu Tyr Lys Gly Gly
145                 150                 155                 160

Tyr Tyr Pro Gly Asn Thr Tyr His Tyr His Ser Gly Gly Ser Tyr His
                165                 170                 175

Gly Ser Gly Tyr His Gly Gly Tyr Lys Gly Lys Tyr Tyr Gly Lys Ala
            180                 185                 190

Lys Lys Tyr Tyr Tyr Lys Tyr Lys Asn Ser Gly Lys Tyr Lys Tyr Leu
        195                 200                 205

Lys Lys Ala Arg Lys Tyr His Arg Lys Gly Tyr Lys Lys Tyr Tyr Gly
    210                 215                 220

Gly Gly Ser Ser Ser Ser Glu Glu Tyr Lys Gly Gly Tyr Tyr Pro Gly
225                 230                 235                 240

Asn Thr Tyr His Tyr His Ser Gly Gly Ser Tyr His Gly Ser Gly Tyr
                245                 250                 255

His Gly Gly Tyr Lys Gly Lys Tyr Tyr Gly Lys Ala Lys Lys Tyr Tyr
            260                 265                 270

Tyr Lys Tyr Lys Asn Ser Gly Lys Tyr Lys Tyr Leu Lys Lys Ala Arg
        275                 280                 285

Lys Tyr His Arg Lys Gly Tyr Lys Lys Tyr Tyr Gly Gly Gly Ser Ser
    290                 295                 300

Val Pro Ala Ala Gly Val Pro Ala Phe Gly Val Pro Ala Ala Gly Val
305                 310                 315                 320

Pro Ala Gly Gly Val Pro Ala Ala Gly Val Pro Ala Phe Gly Val Pro
                325                 330                 335

Ala Ala Gly Val Pro Ala Phe Gly Val Pro Ala Ala Gly Val Pro Ala
            340                 345                 350

Gly Gly Val Pro Ala Ala Gly Val Pro Ala Phe Gly Val Pro Ala Ala
        355                 360                 365

Gly Val Pro Ala Phe Gly Val Pro Ala Ala Gly Val Pro Ala Gly Gly
    370                 375                 380

Val Pro Ala Ala Gly Val Pro Ala Phe Gly Val Pro Ala Ala Gly Val
385                 390                 395                 400

Pro Ala Phe Gly Val Pro Ala Ala Gly Val Pro Ala Gly Gly Val Pro
                405                 410                 415

Ala Ala Gly Val Pro Ala Phe Gly Val Pro Ala Ala Gly Val Pro Ala
            420                 425                 430

Phe Gly Val Pro Ala Ala Gly Val Pro Ala Gly Gly Val Pro Ala Ala
        435                 440                 445

Gly Val Pro Ala Phe Gly Val Pro Ala Ala Gly Val Pro Ala Phe Gly
    450                 455                 460

Val Pro Ala Ala Gly Val Pro Ala Gly Gly Val Pro Ala Ala Gly Val
465                 470                 475                 480

Pro Ala Phe Gly Val Pro Ala Ala Gly Val Pro Ala Phe Gly Val Pro
                485                 490                 495

Ala Ala Gly Val Pro Ala Gly Gly Val Pro Ala Ala Gly Val Pro Ala
            500                 505                 510

Phe Gly Val Pro Ala Ala Gly Val Pro Ala Phe Gly Val Pro Ala Ala
        515                 520                 525

Gly Val Pro Ala Gly Gly Val Pro Ala Ala Gly Val Pro Ala Phe Gly
    530                 535                 540

Val Pro Ala Ala Gly Val Pro Ala Phe Gly Val Pro Ala Ala Gly Val
545                 550                 555                 560
```

Pro Ala Gly Gly Val Pro Ala Ala Gly Val Pro Ala Phe Gly Val Pro
565 570 575

Ala Ala Gly Val Pro Ala Phe Gly Val Pro Ala Ala Gly Val Pro Ala
580 585 590

Gly Gly Val Pro Ala Ala Gly Val Pro Ala Phe Gly Val Pro Ala Ala
595 600 605

Gly Val Pro Ala Phe Gly Val Pro Ala Ala Gly Val Pro Ala Gly Gly
610 615 620

Val Pro Ala Ala Gly Val Pro Ala Phe Gly Val Pro Ala Ala Gly Val
625 630 635 640

Pro Ala Phe Gly Val Pro Ala Ala Gly Val Pro Ala Gly Gly Val Pro
645 650 655

Ala Ala Gly Val Pro Ala Phe Gly Val Pro Ala Ala Gly Val Pro Ala
660 665 670

Phe Gly Val Pro Ala Ala Gly Val Pro Ala Gly Gly Val Pro Ala Ala
675 680 685

Gly Val Pro Ala Phe Gly Val Pro Ala Ala Gly Val Pro Ala Phe Gly
690 695 700

Val Pro Ala Ala Gly Val Pro Ala Gly Gly Val Pro Ala Ala Gly Val
705 710 715 720

Pro Ala Phe Gly Val Pro Ala Ala Gly Val Pro Ala Phe Gly Val Pro
725 730 735

Ala Ala Gly Val Pro Ala Gly Gly Val Pro Ala Ala Gly Val Pro Ala
740 745 750

Phe Gly Val Pro Ala Ala Gly Val Pro Ala Phe Gly Val Pro Ala Ala
755 760 765

Gly Val Pro Ala Gly Gly Val Pro Ala Ala Gly Val Pro Ala Phe Gly
770 775 780

Val Pro Ala Ala Gly Val Pro Ala Phe Gly Val Pro Ala Ala Gly Val
785 790 795 800

Pro Ala Gly Gly Val Pro Ala Ala Gly Val Pro Ala Phe Gly Val Pro
805 810 815

Ala Ala Gly Val Pro Ala Phe Gly Val Pro Ala Ala Gly Val Pro Ala
820 825 830

Gly Gly Val Pro Ala Ala Gly Val Pro Ala Phe Gly Val Pro Ala Ala
835 840 845

Gly Val Pro Ala Phe Gly Val Pro Ala Ala Gly Val Pro Ala Gly Gly
850 855 860

Val Pro Ala Ala Gly Val Pro Ala Phe Gly Val Pro Ala Ala Gly Val
865 870 875 880

Pro Ala Phe Gly Val Pro Ala Ala Gly Val Pro Ala Gly Gly Val Pro
885 890 895

Ala Ala Gly Val Pro Ala Phe Gly Val Pro Ala Ala Gly Val Pro Ala
900 905 910

Phe Gly Val Pro Ala Ala Gly Val Pro Ala Gly Gly Val Pro Ala Ala
915 920 925

Gly Val Pro Ala Phe Gly Val Pro Ala Ala Gly Val Pro Ala Phe Gly
930 935 940

Val Pro Ala Ala Gly Val Pro Ala Gly Gly Val Pro Ala Ala Gly Val
945 950 955 960

Pro Ala Phe Gly Val Pro Ala Ala Gly Val Pro Ala Phe Gly Val Pro
965 970 975

```
Ala Ala Gly Val Pro Ala Gly Gly Val Pro Ala Ala Gly Val Pro Ala
            980                 985                 990

Phe Gly Val Pro Ala Ala Gly Val Pro Ala Phe Gly Val Pro Ala Ala
        995                 1000                1005

Gly Val Pro Ala Gly Gly Val Pro Ala Ala Gly Val Pro Ala Phe Gly
    1010                1015                1020


<210> SEQ ID NO 53
<211> LENGTH: 256
<212> TYPE: PRT
<213> ORGANISM: Artificial Sequence
<220> FEATURE:
<223> OTHER INFORMATION: MFP[Mgfp5]1-EBPPI[G1A3F2]6

<400> SEQUENCE: 53

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ile Pro Ala Ala
65                  70                  75                  80

Gly Ile Pro Ala Phe Gly Ile Pro Ala Ala Gly Ile Pro Ala Gly Gly
                85                  90                  95

Ile Pro Ala Ala Gly Ile Pro Ala Phe Gly Ile Pro Ala Ala Gly Ile
            100                 105                 110

Pro Ala Phe Gly Ile Pro Ala Ala Gly Ile Pro Ala Gly Gly Ile Pro
        115                 120                 125

Ala Ala Gly Ile Pro Ala Phe Gly Ile Pro Ala Ala Gly Ile Pro Ala
    130                 135                 140

Phe Gly Ile Pro Ala Ala Gly Ile Pro Ala Gly Gly Ile Pro Ala Ala
145                 150                 155                 160

Gly Ile Pro Ala Phe Gly Ile Pro Ala Ala Gly Ile Pro Ala Phe Gly
                165                 170                 175

Ile Pro Ala Ala Gly Ile Pro Ala Gly Gly Ile Pro Ala Ala Gly Ile
            180                 185                 190

Pro Ala Phe Gly Ile Pro Ala Ala Gly Ile Pro Ala Phe Gly Ile Pro
        195                 200                 205

Ala Ala Gly Ile Pro Ala Gly Gly Ile Pro Ala Ala Gly Ile Pro Ala
    210                 215                 220

Phe Gly Ile Pro Ala Ala Gly Ile Pro Ala Phe Gly Ile Pro Ala Ala
225                 230                 235                 240

Gly Ile Pro Ala Gly Gly Ile Pro Ala Ala Gly Ile Pro Ala Phe Gly
                245                 250                 255


<210> SEQ ID NO 54
<211> LENGTH: 332
<212> TYPE: PRT
<213> ORGANISM: Artificial Sequence
<220> FEATURE:
<223> OTHER INFORMATION: MFP[Mgfp5]2-EBPPI[G1A3F2]6

<400> SEQUENCE: 54

Ser Ser Glu Glu Tyr Lys Gly Gly Tyr Tyr Pro Gly Asn Thr Tyr His
1               5                   10                  15
```

```
Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ile Pro Ala Ala Gly Ile Pro Ala
145                 150                 155                 160

Phe Gly Ile Pro Ala Ala Gly Ile Pro Ala Gly Gly Ile Pro Ala Ala
                165                 170                 175

Gly Ile Pro Ala Phe Gly Ile Pro Ala Ala Gly Ile Pro Ala Phe Gly
            180                 185                 190

Ile Pro Ala Ala Gly Ile Pro Ala Gly Gly Ile Pro Ala Ala Gly Ile
        195                 200                 205

Pro Ala Phe Gly Ile Pro Ala Ala Gly Ile Pro Ala Phe Gly Ile Pro
    210                 215                 220

Ala Ala Gly Ile Pro Ala Gly Gly Ile Pro Ala Ala Gly Ile Pro Ala
225                 230                 235                 240

Phe Gly Ile Pro Ala Ala Gly Ile Pro Ala Phe Gly Ile Pro Ala Ala
                245                 250                 255

Gly Ile Pro Ala Gly Gly Ile Pro Ala Ala Gly Ile Pro Ala Phe Gly
            260                 265                 270

Ile Pro Ala Ala Gly Ile Pro Ala Phe Gly Ile Pro Ala Ala Gly Ile
        275                 280                 285

Pro Ala Gly Gly Ile Pro Ala Ala Gly Ile Pro Ala Phe Gly Ile Pro
    290                 295                 300

Ala Ala Gly Ile Pro Ala Phe Gly Ile Pro Ala Ala Gly Ile Pro Ala
305                 310                 315                 320

Gly Gly Ile Pro Ala Ala Gly Ile Pro Ala Phe Gly
                325                 330
```

<210> SEQ ID NO 55
<211> LENGTH: 484
<212> TYPE: PRT
<213> ORGANISM: Artificial Sequence
<220> FEATURE:
<223> OTHER INFORMATION: MFP[Mgfp5]4-EBPPI[G1A3F2]6

<400> SEQUENCE: 55

```
Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45
```

```
Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ser Ser Glu Glu Tyr Lys Gly Gly
145                 150                 155                 160

Tyr Tyr Pro Gly Asn Thr Tyr His Tyr His Ser Gly Gly Ser Tyr His
                165                 170                 175

Gly Ser Gly Tyr His Gly Gly Tyr Lys Gly Lys Tyr Tyr Gly Lys Ala
            180                 185                 190

Lys Lys Tyr Tyr Tyr Lys Tyr Lys Asn Ser Gly Lys Tyr Lys Tyr Leu
        195                 200                 205

Lys Lys Ala Arg Lys Tyr His Arg Lys Gly Tyr Lys Lys Tyr Tyr Gly
    210                 215                 220

Gly Gly Ser Ser Ser Ser Glu Glu Tyr Lys Gly Gly Tyr Tyr Pro Gly
225                 230                 235                 240

Asn Thr Tyr His Tyr His Ser Gly Gly Ser Tyr His Gly Ser Gly Tyr
                245                 250                 255

His Gly Gly Tyr Lys Gly Lys Tyr Tyr Gly Lys Ala Lys Lys Tyr Tyr
            260                 265                 270

Tyr Lys Tyr Lys Asn Ser Gly Lys Tyr Lys Tyr Leu Lys Lys Ala Arg
        275                 280                 285

Lys Tyr His Arg Lys Gly Tyr Lys Lys Tyr Tyr Gly Gly Gly Ser Ser
    290                 295                 300

Ile Pro Ala Ala Gly Ile Pro Ala Phe Gly Ile Pro Ala Ala Gly Ile
305                 310                 315                 320

Pro Ala Gly Gly Ile Pro Ala Ala Gly Ile Pro Ala Phe Gly Ile Pro
                325                 330                 335

Ala Ala Gly Ile Pro Ala Phe Gly Ile Pro Ala Ala Gly Ile Pro Ala
            340                 345                 350

Gly Gly Ile Pro Ala Ala Gly Ile Pro Ala Phe Gly Ile Pro Ala Ala
        355                 360                 365

Gly Ile Pro Ala Phe Gly Ile Pro Ala Ala Gly Ile Pro Ala Gly Gly
    370                 375                 380

Ile Pro Ala Ala Gly Ile Pro Ala Phe Gly Ile Pro Ala Ala Gly Ile
385                 390                 395                 400

Pro Ala Phe Gly Ile Pro Ala Ala Gly Ile Pro Ala Gly Gly Ile Pro
                405                 410                 415

Ala Ala Gly Ile Pro Ala Phe Gly Ile Pro Ala Ala Gly Ile Pro Ala
            420                 425                 430

Phe Gly Ile Pro Ala Ala Gly Ile Pro Ala Gly Gly Ile Pro Ala Ala
        435                 440                 445

Gly Ile Pro Ala Phe Gly Ile Pro Ala Ala Gly Ile Pro Ala Phe Gly
    450                 455                 460
```

```
Ile Pro Ala Ala Gly Ile Pro Ala Gly Gly Ile Pro Ala Ala Gly Ile
465                 470                 475                 480

Pro Ala Phe Gly


<210> SEQ ID NO 56
<211> LENGTH: 256
<212> TYPE: PRT
<213> ORGANISM: Artificial Sequence
<220> FEATURE:
<223> OTHER INFORMATION: MFP[Mgfp5]1-EBPPI[G1A4F1]6

<400> SEQUENCE: 56

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ile Pro Ala Ala
65                  70                  75                  80

Gly Ile Pro Ala Gly Gly Ile Pro Ala Ala Gly Ile Pro Ala Ala Gly
                85                  90                  95

Ile Pro Ala Phe Gly Ile Pro Ala Ala Gly Ile Pro Ala Ala Gly Ile
            100                 105                 110

Pro Ala Gly Gly Ile Pro Ala Ala Gly Ile Pro Ala Ala Gly Ile Pro
        115                 120                 125

Ala Phe Gly Ile Pro Ala Ala Gly Ile Pro Ala Ala Gly Ile Pro Ala
    130                 135                 140

Gly Gly Ile Pro Ala Ala Gly Ile Pro Ala Ala Gly Ile Pro Ala Phe
145                 150                 155                 160

Gly Ile Pro Ala Ala Gly Ile Pro Ala Ala Gly Ile Pro Ala Gly Gly
                165                 170                 175

Ile Pro Ala Ala Gly Ile Pro Ala Ala Gly Ile Pro Ala Phe Gly Ile
            180                 185                 190

Pro Ala Ala Gly Ile Pro Ala Ala Gly Ile Pro Ala Gly Gly Ile Pro
        195                 200                 205

Ala Ala Gly Ile Pro Ala Ala Gly Ile Pro Ala Phe Gly Ile Pro Ala
    210                 215                 220

Ala Gly Ile Pro Ala Ala Gly Ile Pro Ala Gly Gly Ile Pro Ala Ala
225                 230                 235                 240

Gly Ile Pro Ala Ala Gly Ile Pro Ala Phe Gly Ile Pro Ala Ala Gly
                245                 250                 255


<210> SEQ ID NO 57
<211> LENGTH: 332
<212> TYPE: PRT
<213> ORGANISM: Artificial Sequence
<220> FEATURE:
<223> OTHER INFORMATION: MFP[Mgfp5]2-EBPPI[G1A4F1]6

<400> SEQUENCE: 57

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30
```

```
Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ile Pro Ala Ala Gly Ile Pro Ala
145                 150                 155                 160

Gly Gly Ile Pro Ala Ala Gly Ile Pro Ala Ala Gly Ile Pro Ala Phe
                165                 170                 175

Gly Ile Pro Ala Ala Gly Ile Pro Ala Ala Gly Ile Pro Ala Gly Gly
            180                 185                 190

Ile Pro Ala Ala Gly Ile Pro Ala Ala Gly Ile Pro Ala Phe Gly Ile
        195                 200                 205

Pro Ala Ala Gly Ile Pro Ala Ala Gly Ile Pro Ala Gly Gly Ile Pro
    210                 215                 220

Ala Ala Gly Ile Pro Ala Ala Gly Ile Pro Ala Phe Gly Ile Pro Ala
225                 230                 235                 240

Ala Gly Ile Pro Ala Ala Gly Ile Pro Ala Gly Gly Ile Pro Ala Ala
                245                 250                 255

Gly Ile Pro Ala Ala Gly Ile Pro Ala Phe Gly Ile Pro Ala Ala Gly
            260                 265                 270

Ile Pro Ala Ala Gly Ile Pro Ala Gly Gly Ile Pro Ala Ala Gly Ile
        275                 280                 285

Pro Ala Ala Gly Ile Pro Ala Phe Gly Ile Pro Ala Ala Gly Ile Pro
    290                 295                 300

Ala Ala Gly Ile Pro Ala Gly Gly Ile Pro Ala Ala Gly Ile Pro Ala
305                 310                 315                 320

Ala Gly Ile Pro Ala Phe Gly Ile Pro Ala Ala Gly
                325                 330


<210> SEQ ID NO 58
<211> LENGTH: 484
<212> TYPE: PRT
<213> ORGANISM: Artificial Sequence
<220> FEATURE:
<223> OTHER INFORMATION: MFP[Mgfp5]4-EBPPI[G1A4F1]6

<400> SEQUENCE: 58

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60
```

```
Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ser Ser Glu Glu Tyr Lys Gly Gly
145                 150                 155                 160

Tyr Tyr Pro Gly Asn Thr Tyr His Tyr His Ser Gly Gly Ser Tyr His
                165                 170                 175

Gly Ser Gly Tyr His Gly Gly Tyr Lys Gly Lys Tyr Tyr Gly Lys Ala
            180                 185                 190

Lys Lys Tyr Tyr Tyr Lys Tyr Lys Asn Ser Gly Lys Tyr Lys Tyr Leu
        195                 200                 205

Lys Lys Ala Arg Lys Tyr His Arg Lys Gly Tyr Lys Lys Tyr Tyr Gly
    210                 215                 220

Gly Gly Ser Ser Ser Ser Glu Glu Tyr Lys Gly Gly Tyr Tyr Pro Gly
225                 230                 235                 240

Asn Thr Tyr His Tyr His Ser Gly Gly Ser Tyr His Gly Ser Gly Tyr
                245                 250                 255

His Gly Gly Tyr Lys Gly Lys Tyr Tyr Gly Lys Ala Lys Lys Tyr Tyr
            260                 265                 270

Tyr Lys Tyr Lys Asn Ser Gly Lys Tyr Lys Tyr Leu Lys Lys Ala Arg
        275                 280                 285

Lys Tyr His Arg Lys Gly Tyr Lys Lys Tyr Tyr Gly Gly Gly Ser Ser
    290                 295                 300

Ile Pro Ala Ala Gly Ile Pro Ala Gly Gly Ile Pro Ala Ala Gly Ile
305                 310                 315                 320

Pro Ala Ala Gly Ile Pro Ala Phe Gly Ile Pro Ala Ala Gly Ile Pro
                325                 330                 335

Ala Ala Gly Ile Pro Ala Gly Gly Ile Pro Ala Ala Gly Ile Pro Ala
            340                 345                 350

Ala Gly Ile Pro Ala Phe Gly Ile Pro Ala Ala Gly Ile Pro Ala Ala
        355                 360                 365

Gly Ile Pro Ala Gly Gly Ile Pro Ala Ala Gly Ile Pro Ala Ala Gly
    370                 375                 380

Ile Pro Ala Phe Gly Ile Pro Ala Ala Gly Ile Pro Ala Ala Gly Ile
385                 390                 395                 400

Pro Ala Gly Gly Ile Pro Ala Ala Gly Ile Pro Ala Ala Gly Ile Pro
                405                 410                 415

Ala Phe Gly Ile Pro Ala Ala Gly Ile Pro Ala Ala Gly Ile Pro Ala
            420                 425                 430

Gly Gly Ile Pro Ala Ala Gly Ile Pro Ala Ala Gly Ile Pro Ala Phe
        435                 440                 445

Gly Ile Pro Ala Ala Gly Ile Pro Ala Ala Gly Ile Pro Ala Gly Gly
    450                 455                 460

Ile Pro Ala Ala Gly Ile Pro Ala Ala Gly Ile Pro Ala Phe Gly Ile
465                 470                 475                 480

Pro Ala Ala Gly
```

<210> SEQ ID NO 59
<211> LENGTH: 436
<212> TYPE: PRT
<213> ORGANISM: Artificial Sequence
<220> FEATURE:
<223> OTHER INFORMATION: EBPPI[G1A3F2]6-MFP[Mgfp5]1-EBPPI[G1A3F2]6

<400> SEQUENCE: 59

Ile Pro Ala Ala Gly Ile Pro Ala Phe Gly Ile Pro Ala Ala Gly Ile
1               5                   10                  15

Pro Ala Gly Gly Ile Pro Ala Ala Gly Ile Pro Ala Phe Gly Ile Pro
            20                  25                  30

Ala Ala Gly Ile Pro Ala Phe Gly Ile Pro Ala Ala Gly Ile Pro Ala
        35                  40                  45

Gly Gly Ile Pro Ala Ala Gly Ile Pro Ala Phe Gly Ile Pro Ala Ala
    50                  55                  60

Gly Ile Pro Ala Phe Gly Ile Pro Ala Ala Gly Ile Pro Ala Gly Gly
65                  70                  75                  80

Ile Pro Ala Ala Gly Ile Pro Ala Phe Gly Ile Pro Ala Ala Gly Ile
                85                  90                  95

Pro Ala Phe Gly Ile Pro Ala Ala Gly Ile Pro Ala Gly Gly Ile Pro
            100                 105                 110

Ala Ala Gly Ile Pro Ala Phe Gly Ile Pro Ala Ala Gly Ile Pro Ala
        115                 120                 125

Phe Gly Ile Pro Ala Ala Gly Ile Pro Ala Gly Gly Ile Pro Ala Ala
    130                 135                 140

Gly Ile Pro Ala Phe Gly Ile Pro Ala Ala Gly Ile Pro Ala Phe Gly
145                 150                 155                 160

Ile Pro Ala Ala Gly Ile Pro Ala Gly Gly Ile Pro Ala Ala Gly Ile
                165                 170                 175

Pro Ala Phe Gly Ser Ser Glu Glu Tyr Lys Gly Gly Tyr Tyr Pro Gly
            180                 185                 190

Asn Thr Tyr His Tyr His Ser Gly Gly Ser Tyr His Gly Ser Gly Tyr
        195                 200                 205

His Gly Gly Tyr Lys Gly Lys Tyr Tyr Gly Lys Ala Lys Lys Tyr Tyr
    210                 215                 220

Tyr Lys Tyr Lys Asn Ser Gly Lys Tyr Lys Tyr Leu Lys Lys Ala Arg
225                 230                 235                 240

Lys Tyr His Arg Lys Gly Tyr Lys Lys Tyr Tyr Gly Gly Gly Ser Ser
                245                 250                 255

Ile Pro Ala Ala Gly Ile Pro Ala Phe Gly Ile Pro Ala Ala Gly Ile
            260                 265                 270

Pro Ala Gly Gly Ile Pro Ala Ala Gly Ile Pro Ala Phe Gly Ile Pro
        275                 280                 285

Ala Ala Gly Ile Pro Ala Phe Gly Ile Pro Ala Ala Gly Ile Pro Ala
    290                 295                 300

Gly Gly Ile Pro Ala Ala Gly Ile Pro Ala Phe Gly Ile Pro Ala Ala
305                 310                 315                 320

Gly Ile Pro Ala Phe Gly Ile Pro Ala Ala Gly Ile Pro Ala Gly Gly
                325                 330                 335

Ile Pro Ala Ala Gly Ile Pro Ala Phe Gly Ile Pro Ala Ala Gly Ile
            340                 345                 350

Pro Ala Phe Gly Ile Pro Ala Ala Gly Ile Pro Ala Gly Gly Ile Pro
        355                 360                 365

```
Ala Ala Gly Ile Pro Ala Phe Gly Ile Pro Ala Ala Gly Ile Pro Ala
    370                 375                 380

Phe Gly Ile Pro Ala Ala Gly Ile Pro Ala Gly Gly Ile Pro Ala Ala
385                 390                 395                 400

Gly Ile Pro Ala Phe Gly Ile Pro Ala Ala Gly Ile Pro Ala Phe Gly
                405                 410                 415

Ile Pro Ala Ala Gly Ile Pro Ala Gly Gly Ile Pro Ala Ala Gly Ile
            420                 425                 430

Pro Ala Phe Gly
        435


<210> SEQ ID NO 60
<211> LENGTH: 512
<212> TYPE: PRT
<213> ORGANISM: Artificial Sequence
<220> FEATURE:
<223> OTHER INFORMATION: EBPPI[G1A3F2]6-MFP[Mgfp5]2-EBPPI[G1A3F2]6

<400> SEQUENCE: 60

Ile Pro Ala Ala Gly Ile Pro Ala Phe Gly Ile Pro Ala Ala Gly Ile
1               5                   10                  15

Pro Ala Gly Gly Ile Pro Ala Ala Gly Ile Pro Ala Phe Gly Ile Pro
            20                  25                  30

Ala Ala Gly Ile Pro Ala Phe Gly Ile Pro Ala Ala Gly Ile Pro Ala
        35                  40                  45

Gly Gly Ile Pro Ala Ala Gly Ile Pro Ala Phe Gly Ile Pro Ala Ala
    50                  55                  60

Gly Ile Pro Ala Phe Gly Ile Pro Ala Ala Gly Ile Pro Ala Gly Gly
65                  70                  75                  80

Ile Pro Ala Ala Gly Ile Pro Ala Phe Gly Ile Pro Ala Ala Gly Ile
                85                  90                  95

Pro Ala Phe Gly Ile Pro Ala Ala Gly Ile Pro Ala Gly Gly Ile Pro
            100                 105                 110

Ala Ala Gly Ile Pro Ala Phe Gly Ile Pro Ala Ala Gly Ile Pro Ala
        115                 120                 125

Phe Gly Ile Pro Ala Ala Gly Ile Pro Ala Gly Gly Ile Pro Ala Ala
    130                 135                 140

Gly Ile Pro Ala Phe Gly Ile Pro Ala Ala Gly Ile Pro Ala Phe Gly
145                 150                 155                 160

Ile Pro Ala Ala Gly Ile Pro Ala Gly Gly Ile Pro Ala Ala Gly Ile
                165                 170                 175

Pro Ala Phe Gly Ser Ser Glu Glu Tyr Lys Gly Gly Tyr Tyr Pro Gly
            180                 185                 190

Asn Thr Tyr His Tyr His Ser Gly Gly Ser Tyr His Gly Ser Gly Tyr
        195                 200                 205

His Gly Gly Tyr Lys Gly Lys Tyr Tyr Gly Lys Ala Lys Lys Tyr Tyr
    210                 215                 220

Tyr Lys Tyr Lys Asn Ser Gly Lys Tyr Lys Tyr Leu Lys Lys Ala Arg
225                 230                 235                 240

Lys Tyr His Arg Lys Gly Tyr Lys Lys Tyr Tyr Gly Gly Gly Ser Ser
                245                 250                 255

Ser Ser Glu Glu Tyr Lys Gly Gly Tyr Tyr Pro Gly Asn Thr Tyr His
            260                 265                 270

Tyr His Ser Gly Gly Ser Tyr His Gly Ser Gly Tyr His Gly Gly Tyr
        275                 280                 285
```

```
Lys Gly Lys Tyr Tyr Gly Lys Ala Lys Lys Tyr Tyr Tyr Lys Tyr Lys
    290                 295                 300

Asn Ser Gly Lys Tyr Lys Tyr Leu Lys Lys Ala Arg Lys Tyr His Arg
305                 310                 315                 320

Lys Gly Tyr Lys Lys Tyr Tyr Gly Gly Gly Ser Ser Ile Pro Ala Ala
                325                 330                 335

Gly Ile Pro Ala Phe Gly Ile Pro Ala Ala Gly Ile Pro Ala Gly Gly
            340                 345                 350

Ile Pro Ala Ala Gly Ile Pro Ala Phe Gly Ile Pro Ala Ala Gly Ile
        355                 360                 365

Pro Ala Phe Gly Ile Pro Ala Ala Gly Ile Pro Ala Gly Gly Ile Pro
    370                 375                 380

Ala Ala Gly Ile Pro Ala Phe Gly Ile Pro Ala Ala Gly Ile Pro Ala
385                 390                 395                 400

Phe Gly Ile Pro Ala Ala Gly Ile Pro Ala Gly Gly Ile Pro Ala Ala
                405                 410                 415

Gly Ile Pro Ala Phe Gly Ile Pro Ala Ala Gly Ile Pro Ala Phe Gly
            420                 425                 430

Ile Pro Ala Ala Gly Ile Pro Ala Gly Gly Ile Pro Ala Ala Gly Ile
        435                 440                 445

Pro Ala Phe Gly Ile Pro Ala Ala Gly Ile Pro Ala Phe Gly Ile Pro
    450                 455                 460

Ala Ala Gly Ile Pro Ala Gly Gly Ile Pro Ala Ala Gly Ile Pro Ala
465                 470                 475                 480

Phe Gly Ile Pro Ala Ala Gly Ile Pro Ala Phe Gly Ile Pro Ala Ala
                485                 490                 495

Gly Ile Pro Ala Gly Gly Ile Pro Ala Ala Gly Ile Pro Ala Phe Gly
            500                 505                 510


<210> SEQ ID NO 61
<211> LENGTH: 664
<212> TYPE: PRT
<213> ORGANISM: Artificial Sequence
<220> FEATURE:
<223> OTHER INFORMATION: EBPPI[G1A3F2]6-MFP[Mgfp5]4-EBPPI[G1A3F2]6

<400> SEQUENCE: 61

Ile Pro Ala Ala Gly Ile Pro Ala Phe Gly Ile Pro Ala Ala Gly Ile
1               5                   10                  15

Pro Ala Gly Gly Ile Pro Ala Ala Gly Ile Pro Ala Phe Gly Ile Pro
            20                  25                  30

Ala Ala Gly Ile Pro Ala Phe Gly Ile Pro Ala Ala Gly Ile Pro Ala
        35                  40                  45

Gly Gly Ile Pro Ala Ala Gly Ile Pro Ala Phe Gly Ile Pro Ala Ala
    50                  55                  60

Gly Ile Pro Ala Phe Gly Ile Pro Ala Ala Gly Ile Pro Ala Gly Gly
65                  70                  75                  80

Ile Pro Ala Ala Gly Ile Pro Ala Phe Gly Ile Pro Ala Ala Gly Ile
                85                  90                  95

Pro Ala Phe Gly Ile Pro Ala Ala Gly Ile Pro Ala Gly Gly Ile Pro
            100                 105                 110

Ala Ala Gly Ile Pro Ala Phe Gly Ile Pro Ala Ala Gly Ile Pro Ala
        115                 120                 125

Phe Gly Ile Pro Ala Ala Gly Ile Pro Ala Gly Gly Ile Pro Ala Ala
    130                 135                 140
```

```
Gly Ile Pro Ala Phe Gly Ile Pro Ala Ala Gly Ile Pro Ala Phe Gly
145                 150                 155                 160

Ile Pro Ala Ala Gly Ile Pro Ala Gly Gly Ile Pro Ala Ala Gly Ile
                165                 170                 175

Pro Ala Phe Gly Ser Ser Glu Glu Tyr Lys Gly Gly Tyr Tyr Pro Gly
            180                 185                 190

Asn Thr Tyr His Tyr His Ser Gly Gly Ser Tyr His Gly Ser Gly Tyr
        195                 200                 205

His Gly Gly Tyr Lys Gly Lys Tyr Tyr Gly Lys Ala Lys Lys Tyr Tyr
    210                 215                 220

Tyr Lys Tyr Lys Asn Ser Gly Lys Tyr Lys Tyr Leu Lys Lys Ala Arg
225                 230                 235                 240

Lys Tyr His Arg Lys Gly Tyr Lys Lys Tyr Tyr Gly Gly Gly Ser Ser
                245                 250                 255

Ser Ser Glu Glu Tyr Lys Gly Gly Tyr Tyr Pro Gly Asn Thr Tyr His
            260                 265                 270

Tyr His Ser Gly Gly Ser Tyr His Gly Ser Gly Tyr His Gly Gly Tyr
        275                 280                 285

Lys Gly Lys Tyr Tyr Gly Lys Ala Lys Lys Tyr Tyr Tyr Lys Tyr Lys
    290                 295                 300

Asn Ser Gly Lys Tyr Lys Tyr Leu Lys Lys Ala Arg Lys Tyr His Arg
305                 310                 315                 320

Lys Gly Tyr Lys Lys Tyr Tyr Gly Gly Gly Ser Ser Ser Ser Glu Glu
                325                 330                 335

Tyr Lys Gly Gly Tyr Tyr Pro Gly Asn Thr Tyr His Tyr His Ser Gly
            340                 345                 350

Gly Ser Tyr His Gly Ser Gly Tyr His Gly Gly Tyr Lys Gly Lys Tyr
        355                 360                 365

Tyr Gly Lys Ala Lys Lys Tyr Tyr Tyr Lys Tyr Lys Asn Ser Gly Lys
    370                 375                 380

Tyr Lys Tyr Leu Lys Lys Ala Arg Lys Tyr His Arg Lys Gly Tyr Lys
385                 390                 395                 400

Lys Tyr Tyr Gly Gly Gly Ser Ser Ser Ser Glu Glu Tyr Lys Gly Gly
                405                 410                 415

Tyr Tyr Pro Gly Asn Thr Tyr His Tyr His Ser Gly Gly Ser Tyr His
            420                 425                 430

Gly Ser Gly Tyr His Gly Gly Tyr Lys Gly Lys Tyr Tyr Gly Lys Ala
        435                 440                 445

Lys Lys Tyr Tyr Tyr Lys Tyr Lys Asn Ser Gly Lys Tyr Lys Tyr Leu
    450                 455                 460

Lys Lys Ala Arg Lys Tyr His Arg Lys Gly Tyr Lys Lys Tyr Tyr Gly
465                 470                 475                 480

Gly Gly Ser Ser Ile Pro Ala Ala Gly Ile Pro Ala Phe Gly Ile Pro
                485                 490                 495

Ala Ala Gly Ile Pro Ala Gly Gly Ile Pro Ala Ala Gly Ile Pro Ala
            500                 505                 510

Phe Gly Ile Pro Ala Ala Gly Ile Pro Ala Phe Gly Ile Pro Ala Ala
        515                 520                 525

Gly Ile Pro Ala Gly Gly Ile Pro Ala Ala Gly Ile Pro Ala Phe Gly
    530                 535                 540

Ile Pro Ala Ala Gly Ile Pro Ala Phe Gly Ile Pro Ala Ala Gly Ile
545                 550                 555                 560
```

```
Pro Ala Gly Gly Ile Pro Ala Ala Gly Ile Pro Ala Phe Gly Ile Pro
                565                 570                 575

Ala Ala Gly Ile Pro Ala Phe Gly Ile Pro Ala Ala Gly Ile Pro Ala
            580                 585                 590

Gly Gly Ile Pro Ala Ala Gly Ile Pro Ala Phe Gly Ile Pro Ala Ala
        595                 600                 605

Gly Ile Pro Ala Phe Gly Ile Pro Ala Ala Gly Ile Pro Ala Gly Gly
    610                 615                 620

Ile Pro Ala Ala Gly Ile Pro Ala Phe Gly Ile Pro Ala Ala Gly Ile
625                 630                 635                 640

Pro Ala Phe Gly Ile Pro Ala Ala Gly Ile Pro Ala Gly Gly Ile Pro
                645                 650                 655

Ala Ala Gly Ile Pro Ala Phe Gly
            660


<210> SEQ ID NO 62
<211> LENGTH: 436
<212> TYPE: PRT
<213> ORGANISM: Artificial Sequence
<220> FEATURE:
<223> OTHER INFORMATION: EBPPI[G1A4F1]6-MFP[Mgfp5]1-EBPPI[G1A4F1]6

<400> SEQUENCE: 62

Ile Pro Ala Ala Gly Ile Pro Ala Gly Gly Ile Pro Ala Ala Gly Ile
1               5                   10                  15

Pro Ala Ala Gly Ile Pro Ala Phe Gly Ile Pro Ala Ala Gly Ile Pro
            20                  25                  30

Ala Ala Gly Ile Pro Ala Gly Gly Ile Pro Ala Ala Gly Ile Pro Ala
        35                  40                  45

Ala Gly Ile Pro Ala Phe Gly Ile Pro Ala Ala Gly Ile Pro Ala Ala
    50                  55                  60

Gly Ile Pro Ala Gly Gly Ile Pro Ala Ala Gly Ile Pro Ala Ala Gly
65                  70                  75                  80

Ile Pro Ala Phe Gly Ile Pro Ala Ala Gly Ile Pro Ala Ala Gly Ile
                85                  90                  95

Pro Ala Gly Gly Ile Pro Ala Ala Gly Ile Pro Ala Ala Gly Ile Pro
            100                 105                 110

Ala Phe Gly Ile Pro Ala Ala Gly Ile Pro Ala Ala Gly Ile Pro Ala
        115                 120                 125

Gly Gly Ile Pro Ala Ala Gly Ile Pro Ala Ala Gly Ile Pro Ala Phe
    130                 135                 140

Gly Ile Pro Ala Ala Gly Ile Pro Ala Ala Gly Ile Pro Ala Gly Gly
145                 150                 155                 160

Ile Pro Ala Ala Gly Ile Pro Ala Ala Gly Ile Pro Ala Phe Gly Ile
                165                 170                 175

Pro Ala Ala Gly Ser Ser Glu Glu Tyr Lys Gly Gly Tyr Tyr Pro Gly
            180                 185                 190

Asn Thr Tyr His Tyr His Ser Gly Gly Ser Tyr His Gly Ser Gly Tyr
        195                 200                 205

His Gly Gly Tyr Lys Gly Lys Tyr Tyr Gly Lys Ala Lys Lys Tyr Tyr
    210                 215                 220

Tyr Lys Tyr Lys Asn Ser Gly Lys Tyr Lys Tyr Leu Lys Lys Ala Arg
225                 230                 235                 240

Lys Tyr His Arg Lys Gly Tyr Lys Lys Tyr Tyr Gly Gly Gly Ser Ser
                245                 250                 255
```

```
Ile Pro Ala Ala Gly Ile Pro Ala Gly Gly Ile Pro Ala Ala Gly Ile
            260                 265                 270

Pro Ala Ala Gly Ile Pro Ala Phe Gly Ile Pro Ala Ala Gly Ile Pro
        275                 280                 285

Ala Ala Gly Ile Pro Ala Gly Gly Ile Pro Ala Ala Gly Ile Pro Ala
    290                 295                 300

Ala Gly Ile Pro Ala Phe Gly Ile Pro Ala Ala Gly Ile Pro Ala Ala
305                 310                 315                 320

Gly Ile Pro Ala Gly Gly Ile Pro Ala Ala Gly Ile Pro Ala Ala Gly
                325                 330                 335

Ile Pro Ala Phe Gly Ile Pro Ala Ala Gly Ile Pro Ala Ala Gly Ile
            340                 345                 350

Pro Ala Gly Gly Ile Pro Ala Ala Gly Ile Pro Ala Ala Gly Ile Pro
        355                 360                 365

Ala Phe Gly Ile Pro Ala Ala Gly Ile Pro Ala Ala Gly Ile Pro Ala
    370                 375                 380

Gly Gly Ile Pro Ala Ala Gly Ile Pro Ala Ala Gly Ile Pro Ala Phe
385                 390                 395                 400

Gly Ile Pro Ala Ala Gly Ile Pro Ala Ala Gly Ile Pro Ala Gly Gly
                405                 410                 415

Ile Pro Ala Ala Gly Ile Pro Ala Ala Gly Ile Pro Ala Phe Gly Ile
            420                 425                 430

Pro Ala Ala Gly
        435


<210> SEQ ID NO 63
<211> LENGTH: 512
<212> TYPE: PRT
<213> ORGANISM: Artificial Sequence
<220> FEATURE:
<223> OTHER INFORMATION: EBPPI[G1A4F1]6-MFP[Mgfp5]2-EBPPI[G1A4F1]6

<400> SEQUENCE: 63

Ile Pro Ala Ala Gly Ile Pro Ala Gly Gly Ile Pro Ala Ala Gly Ile
1               5                   10                  15

Pro Ala Ala Gly Ile Pro Ala Phe Gly Ile Pro Ala Ala Gly Ile Pro
            20                  25                  30

Ala Ala Gly Ile Pro Ala Gly Gly Ile Pro Ala Ala Gly Ile Pro Ala
        35                  40                  45

Ala Gly Ile Pro Ala Phe Gly Ile Pro Ala Ala Gly Ile Pro Ala Ala
    50                  55                  60

Gly Ile Pro Ala Gly Gly Ile Pro Ala Ala Gly Ile Pro Ala Ala Gly
65                  70                  75                  80

Ile Pro Ala Phe Gly Ile Pro Ala Ala Gly Ile Pro Ala Ala Gly Ile
                85                  90                  95

Pro Ala Gly Gly Ile Pro Ala Ala Gly Ile Pro Ala Ala Gly Ile Pro
            100                 105                 110

Ala Phe Gly Ile Pro Ala Ala Gly Ile Pro Ala Ala Gly Ile Pro Ala
        115                 120                 125

Gly Gly Ile Pro Ala Ala Gly Ile Pro Ala Ala Gly Ile Pro Ala Phe
    130                 135                 140

Gly Ile Pro Ala Ala Gly Ile Pro Ala Ala Gly Ile Pro Ala Gly Gly
145                 150                 155                 160

Ile Pro Ala Ala Gly Ile Pro Ala Ala Gly Ile Pro Ala Phe Gly Ile
                165                 170                 175
```

```
Pro Ala Ala Gly Ser Ser Glu Glu Tyr Lys Gly Gly Tyr Tyr Pro Gly
            180                 185                 190

Asn Thr Tyr His Tyr His Ser Gly Gly Ser Tyr His Gly Ser Gly Tyr
        195                 200                 205

His Gly Gly Tyr Lys Gly Lys Tyr Tyr Gly Lys Ala Lys Lys Tyr Tyr
    210                 215                 220

Tyr Lys Tyr Lys Asn Ser Gly Lys Tyr Lys Tyr Leu Lys Lys Ala Arg
225                 230                 235                 240

Lys Tyr His Arg Lys Gly Tyr Lys Lys Tyr Tyr Gly Gly Gly Ser Ser
                245                 250                 255

Ser Ser Glu Glu Tyr Lys Gly Gly Tyr Tyr Pro Gly Asn Thr Tyr His
            260                 265                 270

Tyr His Ser Gly Gly Ser Tyr His Gly Ser Gly Tyr His Gly Gly Tyr
        275                 280                 285

Lys Gly Lys Tyr Tyr Gly Lys Ala Lys Lys Tyr Tyr Tyr Lys Tyr Lys
    290                 295                 300

Asn Ser Gly Lys Tyr Lys Tyr Leu Lys Lys Ala Arg Lys Tyr His Arg
305                 310                 315                 320

Lys Gly Tyr Lys Lys Tyr Tyr Gly Gly Gly Ser Ser Ile Pro Ala Ala
                325                 330                 335

Gly Ile Pro Ala Gly Gly Ile Pro Ala Ala Gly Ile Pro Ala Ala Gly
            340                 345                 350

Ile Pro Ala Phe Gly Ile Pro Ala Ala Gly Ile Pro Ala Ala Gly Ile
        355                 360                 365

Pro Ala Gly Gly Ile Pro Ala Ala Gly Ile Pro Ala Ala Gly Ile Pro
    370                 375                 380

Ala Phe Gly Ile Pro Ala Ala Gly Ile Pro Ala Ala Gly Ile Pro Ala
385                 390                 395                 400

Gly Gly Ile Pro Ala Ala Gly Ile Pro Ala Ala Gly Ile Pro Ala Phe
                405                 410                 415

Gly Ile Pro Ala Ala Gly Ile Pro Ala Ala Gly Ile Pro Ala Gly Gly
            420                 425                 430

Ile Pro Ala Ala Gly Ile Pro Ala Ala Gly Ile Pro Ala Phe Gly Ile
        435                 440                 445

Pro Ala Ala Gly Ile Pro Ala Ala Gly Ile Pro Ala Gly Gly Ile Pro
    450                 455                 460

Ala Ala Gly Ile Pro Ala Ala Gly Ile Pro Ala Phe Gly Ile Pro Ala
465                 470                 475                 480

Ala Gly Ile Pro Ala Ala Gly Ile Pro Ala Gly Gly Ile Pro Ala Ala
                485                 490                 495

Gly Ile Pro Ala Ala Gly Ile Pro Ala Phe Gly Ile Pro Ala Ala Gly
            500                 505                 510
```

<210> SEQ ID NO 64
<211> LENGTH: 664
<212> TYPE: PRT
<213> ORGANISM: Artificial Sequence
<220> FEATURE:
<223> OTHER INFORMATION: EBPPI[G1A4F1]6-MFP[Mgfp5]4-EBPPI[G1A4F1]6

<400> SEQUENCE: 64

```
Ile Pro Ala Ala Gly Ile Pro Ala Gly Gly Ile Pro Ala Ala Gly Ile
1               5                   10                  15

Pro Ala Ala Gly Ile Pro Ala Phe Gly Ile Pro Ala Ala Gly Ile Pro
            20                  25                  30
```

```
Ala Ala Gly Ile Pro Ala Gly Gly Ile Pro Ala Ala Gly Ile Pro Ala
        35                  40                  45

Ala Gly Ile Pro Ala Phe Gly Ile Pro Ala Ala Gly Ile Pro Ala Ala
    50                  55                  60

Gly Ile Pro Ala Gly Gly Ile Pro Ala Ala Gly Ile Pro Ala Ala Gly
65                  70                  75                  80

Ile Pro Ala Phe Gly Ile Pro Ala Ala Gly Ile Pro Ala Ala Gly Ile
                85                  90                  95

Pro Ala Gly Gly Ile Pro Ala Ala Gly Ile Pro Ala Ala Gly Ile Pro
            100                 105                 110

Ala Phe Gly Ile Pro Ala Ala Gly Ile Pro Ala Ala Gly Ile Pro Ala
        115                 120                 125

Gly Gly Ile Pro Ala Ala Gly Ile Pro Ala Ala Gly Ile Pro Ala Phe
    130                 135                 140

Gly Ile Pro Ala Ala Gly Ile Pro Ala Ala Gly Ile Pro Ala Gly Gly
145                 150                 155                 160

Ile Pro Ala Ala Gly Ile Pro Ala Ala Gly Ile Pro Ala Phe Gly Ile
                165                 170                 175

Pro Ala Ala Gly Ser Ser Glu Glu Tyr Lys Gly Gly Tyr Tyr Pro Gly
            180                 185                 190

Asn Thr Tyr His Tyr His Ser Gly Gly Ser Tyr His Gly Ser Gly Tyr
        195                 200                 205

His Gly Gly Tyr Lys Gly Lys Tyr Tyr Gly Lys Ala Lys Lys Tyr Tyr
    210                 215                 220

Tyr Lys Tyr Lys Asn Ser Gly Lys Tyr Lys Tyr Leu Lys Lys Ala Arg
225                 230                 235                 240

Lys Tyr His Arg Lys Gly Tyr Lys Lys Tyr Tyr Gly Gly Gly Ser Ser
                245                 250                 255

Ser Ser Glu Glu Tyr Lys Gly Gly Tyr Tyr Pro Gly Asn Thr Tyr His
            260                 265                 270

Tyr His Ser Gly Gly Ser Tyr His Gly Ser Gly Tyr His Gly Gly Tyr
        275                 280                 285

Lys Gly Lys Tyr Tyr Gly Lys Ala Lys Lys Tyr Tyr Tyr Lys Tyr Lys
    290                 295                 300

Asn Ser Gly Lys Tyr Lys Tyr Leu Lys Lys Ala Arg Lys Tyr His Arg
305                 310                 315                 320

Lys Gly Tyr Lys Lys Tyr Tyr Gly Gly Gly Ser Ser Ser Ser Glu Glu
                325                 330                 335

Tyr Lys Gly Gly Tyr Tyr Pro Gly Asn Thr Tyr His Tyr His Ser Gly
            340                 345                 350

Gly Ser Tyr His Gly Ser Gly Tyr His Gly Gly Tyr Lys Gly Lys Tyr
        355                 360                 365

Tyr Gly Lys Ala Lys Lys Tyr Tyr Tyr Lys Tyr Lys Asn Ser Gly Lys
    370                 375                 380

Tyr Lys Tyr Leu Lys Lys Ala Arg Lys Tyr His Arg Lys Gly Tyr Lys
385                 390                 395                 400

Lys Tyr Tyr Gly Gly Gly Ser Ser Ser Ser Glu Glu Tyr Lys Gly Gly
                405                 410                 415

Tyr Tyr Pro Gly Asn Thr Tyr His Tyr His Ser Gly Gly Ser Tyr His
            420                 425                 430

Gly Ser Gly Tyr His Gly Gly Tyr Lys Gly Lys Tyr Tyr Gly Lys Ala
        435                 440                 445

Lys Lys Tyr Tyr Tyr Lys Tyr Lys Asn Ser Gly Lys Tyr Lys Tyr Leu
```

```
    450                 455                 460

Lys Lys Ala Arg Lys Tyr His Arg Lys Gly Tyr Lys Lys Tyr Tyr Gly
465                 470                 475                 480

Gly Gly Ser Ser Ile Pro Ala Ala Gly Ile Pro Ala Gly Gly Ile Pro
                485                 490                 495

Ala Ala Gly Ile Pro Ala Ala Gly Ile Pro Ala Phe Gly Ile Pro Ala
            500                 505                 510

Ala Gly Ile Pro Ala Ala Gly Ile Pro Ala Gly Gly Ile Pro Ala Ala
        515                 520                 525

Gly Ile Pro Ala Ala Gly Ile Pro Ala Phe Gly Ile Pro Ala Ala Gly
    530                 535                 540

Ile Pro Ala Ala Gly Ile Pro Ala Gly Gly Ile Pro Ala Ala Gly Ile
545                 550                 555                 560

Pro Ala Ala Gly Ile Pro Ala Phe Gly Ile Pro Ala Ala Gly Ile Pro
                565                 570                 575

Ala Ala Gly Ile Pro Ala Gly Gly Ile Pro Ala Ala Gly Ile Pro Ala
            580                 585                 590

Ala Gly Ile Pro Ala Phe Gly Ile Pro Ala Ala Gly Ile Pro Ala Ala
        595                 600                 605

Gly Ile Pro Ala Gly Gly Ile Pro Ala Ala Gly Ile Pro Ala Ala Gly
    610                 615                 620

Ile Pro Ala Phe Gly Ile Pro Ala Ala Gly Ile Pro Ala Ala Gly Ile
625                 630                 635                 640

Pro Ala Gly Gly Ile Pro Ala Ala Gly Ile Pro Ala Ala Gly Ile Pro
                645                 650                 655

Ala Phe Gly Ile Pro Ala Ala Gly
            660


<210> SEQ ID NO 65
<211> LENGTH: 332
<212> TYPE: PRT
<213> ORGANISM: Artificial Sequence
<220> FEATURE:
<223> OTHER INFORMATION: MFP[Mgfp5]1-EBPPI[G1A3F2]6-MFP[Mgfp5]1

<400> SEQUENCE: 65

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ile Pro Ala Ala
65                  70                  75                  80

Gly Ile Pro Ala Phe Gly Ile Pro Ala Ala Gly Ile Pro Ala Gly Gly
                85                  90                  95

Ile Pro Ala Ala Gly Ile Pro Ala Phe Gly Ile Pro Ala Ala Gly Ile
            100                 105                 110

Pro Ala Phe Gly Ile Pro Ala Ala Gly Ile Pro Ala Gly Gly Ile Pro
        115                 120                 125

Ala Ala Gly Ile Pro Ala Phe Gly Ile Pro Ala Ala Gly Ile Pro Ala
    130                 135                 140

Phe Gly Ile Pro Ala Ala Gly Ile Pro Ala Gly Gly Ile Pro Ala Ala
```

```
145                 150                 155                 160

Gly Ile Pro Ala Phe Gly Ile Pro Ala Ala Gly Ile Pro Ala Phe Gly
                165                 170                 175

Ile Pro Ala Ala Gly Ile Pro Ala Gly Gly Ile Pro Ala Ala Gly Ile
            180                 185                 190

Pro Ala Phe Gly Ile Pro Ala Ala Gly Ile Pro Ala Phe Gly Ile Pro
        195                 200                 205

Ala Ala Gly Ile Pro Ala Gly Gly Ile Pro Ala Ala Gly Ile Pro Ala
    210                 215                 220

Phe Gly Ile Pro Ala Ala Gly Ile Pro Ala Phe Gly Ile Pro Ala Ala
225                 230                 235                 240

Gly Ile Pro Ala Gly Gly Ile Pro Ala Ala Gly Ile Pro Ala Phe Gly
                245                 250                 255

Ser Ser Glu Glu Tyr Lys Gly Gly Tyr Tyr Pro Gly Asn Thr Tyr His
            260                 265                 270

Tyr His Ser Gly Gly Ser Tyr His Gly Ser Gly Tyr His Gly Gly Tyr
        275                 280                 285

Lys Gly Lys Tyr Tyr Gly Lys Ala Lys Lys Tyr Tyr Tyr Lys Tyr Lys
    290                 295                 300

Asn Ser Gly Lys Tyr Lys Tyr Leu Lys Lys Ala Arg Lys Tyr His Arg
305                 310                 315                 320

Lys Gly Tyr Lys Lys Tyr Tyr Gly Gly Gly Ser Ser
                325                 330


<210> SEQ ID NO 66
<211> LENGTH: 484
<212> TYPE: PRT
<213> ORGANISM: Artificial Sequence
<220> FEATURE:
<223> OTHER INFORMATION: MFP[Mgfp5]2-EBPPI[G1A3F2]6-MFP[Mgfp5]2

<400> SEQUENCE: 66

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ile Pro Ala Ala Gly Ile Pro Ala
145                 150                 155                 160

Phe Gly Ile Pro Ala Ala Gly Ile Pro Ala Gly Gly Ile Pro Ala Ala
                165                 170                 175

Gly Ile Pro Ala Phe Gly Ile Pro Ala Ala Gly Ile Pro Ala Phe Gly
```

```
            180                 185                 190

Ile Pro Ala Ala Gly Ile Pro Ala Gly Gly Ile Pro Ala Ala Gly Ile
        195                 200                 205

Pro Ala Phe Gly Ile Pro Ala Ala Gly Ile Pro Ala Phe Gly Ile Pro
    210                 215                 220

Ala Ala Gly Ile Pro Ala Gly Gly Ile Pro Ala Ala Gly Ile Pro Ala
225                 230                 235                 240

Phe Gly Ile Pro Ala Ala Gly Ile Pro Ala Phe Gly Ile Pro Ala Ala
                245                 250                 255

Gly Ile Pro Ala Gly Gly Ile Pro Ala Ala Gly Ile Pro Ala Phe Gly
            260                 265                 270

Ile Pro Ala Ala Gly Ile Pro Ala Phe Gly Ile Pro Ala Ala Gly Ile
        275                 280                 285

Pro Ala Gly Gly Ile Pro Ala Ala Gly Ile Pro Ala Phe Gly Ile Pro
    290                 295                 300

Ala Ala Gly Ile Pro Ala Phe Gly Ile Pro Ala Ala Gly Ile Pro Ala
305                 310                 315                 320

Gly Gly Ile Pro Ala Ala Gly Ile Pro Ala Phe Gly Ser Ser Glu Glu
                325                 330                 335

Tyr Lys Gly Gly Tyr Tyr Pro Gly Asn Thr Tyr His Tyr His Ser Gly
            340                 345                 350

Gly Ser Tyr His Gly Ser Gly Tyr His Gly Gly Tyr Lys Gly Lys Tyr
        355                 360                 365

Tyr Gly Lys Ala Lys Lys Tyr Tyr Tyr Lys Tyr Lys Asn Ser Gly Lys
    370                 375                 380

Tyr Lys Tyr Leu Lys Lys Ala Arg Lys Tyr His Arg Lys Gly Tyr Lys
385                 390                 395                 400

Lys Tyr Tyr Gly Gly Gly Ser Ser Ser Ser Glu Glu Tyr Lys Gly Gly
                405                 410                 415

Tyr Tyr Pro Gly Asn Thr Tyr His Tyr His Ser Gly Gly Ser Tyr His
            420                 425                 430

Gly Ser Gly Tyr His Gly Gly Tyr Lys Gly Lys Tyr Tyr Gly Lys Ala
        435                 440                 445

Lys Lys Tyr Tyr Tyr Lys Tyr Lys Asn Ser Gly Lys Tyr Lys Tyr Leu
    450                 455                 460

Lys Lys Ala Arg Lys Tyr His Arg Lys Gly Tyr Lys Lys Tyr Tyr Gly
465                 470                 475                 480

Gly Gly Ser Ser
```

<210> SEQ ID NO 67
<211> LENGTH: 788
<212> TYPE: PRT
<213> ORGANISM: Artificial Sequence
<220> FEATURE:
<223> OTHER INFORMATION: MFP[Mgfp5]4-EBPPI[G1A3F2]6-MFP[Mgfp5]4

<400> SEQUENCE: 67

```
Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60
```

```
Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ser Ser Glu Glu Tyr Lys Gly Gly
145                 150                 155                 160

Tyr Tyr Pro Gly Asn Thr Tyr His Tyr His Ser Gly Gly Ser Tyr His
                165                 170                 175

Gly Ser Gly Tyr His Gly Gly Tyr Lys Gly Lys Tyr Tyr Gly Lys Ala
            180                 185                 190

Lys Lys Tyr Tyr Tyr Lys Tyr Lys Asn Ser Gly Lys Tyr Lys Tyr Leu
        195                 200                 205

Lys Lys Ala Arg Lys Tyr His Arg Lys Gly Tyr Lys Lys Tyr Tyr Gly
    210                 215                 220

Gly Gly Ser Ser Ser Ser Glu Glu Tyr Lys Gly Gly Tyr Tyr Pro Gly
225                 230                 235                 240

Asn Thr Tyr His Tyr His Ser Gly Gly Ser Tyr His Gly Ser Gly Tyr
                245                 250                 255

His Gly Gly Tyr Lys Gly Lys Tyr Tyr Gly Lys Ala Lys Lys Tyr Tyr
            260                 265                 270

Tyr Lys Tyr Lys Asn Ser Gly Lys Tyr Lys Tyr Leu Lys Lys Ala Arg
        275                 280                 285

Lys Tyr His Arg Lys Gly Tyr Lys Lys Tyr Tyr Gly Gly Gly Ser Ser
    290                 295                 300

Ile Pro Ala Ala Gly Ile Pro Ala Phe Gly Ile Pro Ala Ala Gly Ile
305                 310                 315                 320

Pro Ala Gly Gly Ile Pro Ala Ala Gly Ile Pro Ala Phe Gly Ile Pro
                325                 330                 335

Ala Ala Gly Ile Pro Ala Phe Gly Ile Pro Ala Ala Gly Ile Pro Ala
            340                 345                 350

Gly Gly Ile Pro Ala Ala Gly Ile Pro Ala Phe Gly Ile Pro Ala Ala
        355                 360                 365

Gly Ile Pro Ala Phe Gly Ile Pro Ala Ala Gly Ile Pro Ala Gly Gly
    370                 375                 380

Ile Pro Ala Ala Gly Ile Pro Ala Phe Gly Ile Pro Ala Ala Gly Ile
385                 390                 395                 400

Pro Ala Phe Gly Ile Pro Ala Ala Gly Ile Pro Ala Gly Gly Ile Pro
                405                 410                 415

Ala Ala Gly Ile Pro Ala Phe Gly Ile Pro Ala Ala Gly Ile Pro Ala
            420                 425                 430

Phe Gly Ile Pro Ala Ala Gly Ile Pro Ala Gly Gly Ile Pro Ala Ala
        435                 440                 445

Gly Ile Pro Ala Phe Gly Ile Pro Ala Ala Gly Ile Pro Ala Phe Gly
    450                 455                 460

Ile Pro Ala Ala Gly Ile Pro Ala Gly Gly Ile Pro Ala Ala Gly Ile
465                 470                 475                 480
```

```
Pro Ala Phe Gly Ser Ser Glu Glu Tyr Lys Gly Gly Tyr Tyr Pro Gly
                485                 490                 495

Asn Thr Tyr His Tyr His Ser Gly Gly Ser Tyr His Gly Ser Gly Tyr
            500                 505                 510

His Gly Gly Tyr Lys Gly Lys Tyr Tyr Gly Lys Ala Lys Lys Tyr Tyr
        515                 520                 525

Tyr Lys Tyr Lys Asn Ser Gly Lys Tyr Lys Tyr Leu Lys Lys Ala Arg
    530                 535                 540

Lys Tyr His Arg Lys Gly Tyr Lys Lys Tyr Tyr Gly Gly Gly Ser Ser
545                 550                 555                 560

Ser Ser Glu Glu Tyr Lys Gly Gly Tyr Tyr Pro Gly Asn Thr Tyr His
                565                 570                 575

Tyr His Ser Gly Gly Ser Tyr His Gly Ser Gly Tyr His Gly Gly Tyr
            580                 585                 590

Lys Gly Lys Tyr Tyr Gly Lys Ala Lys Lys Tyr Tyr Tyr Lys Tyr Lys
        595                 600                 605

Asn Ser Gly Lys Tyr Lys Tyr Leu Lys Lys Ala Arg Lys Tyr His Arg
    610                 615                 620

Lys Gly Tyr Lys Lys Tyr Tyr Gly Gly Gly Ser Ser Ser Ser Glu Glu
625                 630                 635                 640

Tyr Lys Gly Gly Tyr Tyr Pro Gly Asn Thr Tyr His Tyr His Ser Gly
                645                 650                 655

Gly Ser Tyr His Gly Ser Gly Tyr His Gly Gly Tyr Lys Gly Lys Tyr
            660                 665                 670

Tyr Gly Lys Ala Lys Lys Tyr Tyr Tyr Lys Tyr Lys Asn Ser Gly Lys
        675                 680                 685

Tyr Lys Tyr Leu Lys Lys Ala Arg Lys Tyr His Arg Lys Gly Tyr Lys
    690                 695                 700

Lys Tyr Tyr Gly Gly Gly Ser Ser Ser Ser Glu Glu Tyr Lys Gly Gly
705                 710                 715                 720

Tyr Tyr Pro Gly Asn Thr Tyr His Tyr His Ser Gly Gly Ser Tyr His
                725                 730                 735

Gly Ser Gly Tyr His Gly Gly Tyr Lys Gly Lys Tyr Tyr Gly Lys Ala
            740                 745                 750

Lys Lys Tyr Tyr Tyr Lys Tyr Lys Asn Ser Gly Lys Tyr Lys Tyr Leu
        755                 760                 765

Lys Lys Ala Arg Lys Tyr His Arg Lys Gly Tyr Lys Lys Tyr Tyr Gly
    770                 775                 780

Gly Gly Ser Ser
785
```

<210> SEQ ID NO 68
<211> LENGTH: 332
<212> TYPE: PRT
<213> ORGANISM: Artificial Sequence
<220> FEATURE:
<223> OTHER INFORMATION: MFP[Mgfp5]1-EBPPI[G1A4F1]6-MFP[Mgfp5]1

<400> SEQUENCE: 68

```
Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45
```

```
Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ile Pro Ala Ala
65                  70                  75                  80

Gly Ile Pro Ala Gly Gly Ile Pro Ala Ala Gly Ile Pro Ala Ala Gly
                85                  90                  95

Ile Pro Ala Phe Gly Ile Pro Ala Ala Gly Ile Pro Ala Ala Gly Ile
            100                 105                 110

Pro Ala Gly Gly Ile Pro Ala Ala Gly Ile Pro Ala Ala Gly Ile Pro
        115                 120                 125

Ala Phe Gly Ile Pro Ala Ala Gly Ile Pro Ala Ala Gly Ile Pro Ala
    130                 135                 140

Gly Gly Ile Pro Ala Ala Gly Ile Pro Ala Ala Gly Ile Pro Ala Phe
145                 150                 155                 160

Gly Ile Pro Ala Ala Gly Ile Pro Ala Ala Gly Ile Pro Ala Gly Gly
                165                 170                 175

Ile Pro Ala Ala Gly Ile Pro Ala Ala Gly Ile Pro Ala Phe Gly Ile
            180                 185                 190

Pro Ala Ala Gly Ile Pro Ala Ala Gly Ile Pro Ala Gly Gly Ile Pro
        195                 200                 205

Ala Ala Gly Ile Pro Ala Ala Gly Ile Pro Ala Phe Gly Ile Pro Ala
    210                 215                 220

Ala Gly Ile Pro Ala Ala Gly Ile Pro Ala Gly Gly Ile Pro Ala Ala
225                 230                 235                 240

Gly Ile Pro Ala Ala Gly Ile Pro Ala Phe Gly Ile Pro Ala Ala Gly
                245                 250                 255

Ser Ser Glu Glu Tyr Lys Gly Gly Tyr Tyr Pro Gly Asn Thr Tyr His
            260                 265                 270

Tyr His Ser Gly Gly Ser Tyr His Gly Ser Gly Tyr His Gly Gly Tyr
        275                 280                 285

Lys Gly Lys Tyr Tyr Gly Lys Ala Lys Lys Tyr Tyr Tyr Lys Tyr Lys
    290                 295                 300

Asn Ser Gly Lys Tyr Lys Tyr Leu Lys Lys Ala Arg Lys Tyr His Arg
305                 310                 315                 320

Lys Gly Tyr Lys Lys Tyr Tyr Gly Gly Gly Ser Ser
                325                 330


<210> SEQ ID NO 69
<211> LENGTH: 484
<212> TYPE: PRT
<213> ORGANISM: Artificial Sequence
<220> FEATURE:
<223> OTHER INFORMATION: MFP[Mgfp5]2-EBPPI[G1A4F1]6MFP[Mgfp5]2

<400> SEQUENCE: 69

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80
```

```
Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ile Pro Ala Ala Gly Ile Pro Ala
145                 150                 155                 160

Gly Gly Ile Pro Ala Ala Gly Ile Pro Ala Ala Gly Ile Pro Ala Phe
                165                 170                 175

Gly Ile Pro Ala Ala Gly Ile Pro Ala Ala Gly Ile Pro Ala Gly Gly
            180                 185                 190

Ile Pro Ala Ala Gly Ile Pro Ala Ala Gly Ile Pro Ala Phe Gly Ile
        195                 200                 205

Pro Ala Ala Gly Ile Pro Ala Ala Gly Ile Pro Ala Gly Gly Ile Pro
    210                 215                 220

Ala Ala Gly Ile Pro Ala Ala Gly Ile Pro Ala Phe Gly Ile Pro Ala
225                 230                 235                 240

Ala Gly Ile Pro Ala Ala Gly Ile Pro Ala Gly Gly Ile Pro Ala Ala
                245                 250                 255

Gly Ile Pro Ala Ala Gly Ile Pro Ala Phe Gly Ile Pro Ala Ala Gly
            260                 265                 270

Ile Pro Ala Ala Gly Ile Pro Ala Gly Gly Ile Pro Ala Ala Gly Ile
        275                 280                 285

Pro Ala Ala Gly Ile Pro Ala Phe Gly Ile Pro Ala Ala Gly Ile Pro
    290                 295                 300

Ala Ala Gly Ile Pro Ala Gly Gly Ile Pro Ala Ala Gly Ile Pro Ala
305                 310                 315                 320

Ala Gly Ile Pro Ala Phe Gly Ile Pro Ala Ala Gly Ser Ser Glu Glu
                325                 330                 335

Tyr Lys Gly Gly Tyr Tyr Pro Gly Asn Thr Tyr His Tyr His Ser Gly
            340                 345                 350

Gly Ser Tyr His Gly Ser Gly Tyr His Gly Gly Tyr Lys Gly Lys Tyr
        355                 360                 365

Tyr Gly Lys Ala Lys Lys Tyr Tyr Tyr Lys Tyr Lys Asn Ser Gly Lys
    370                 375                 380

Tyr Lys Tyr Leu Lys Lys Ala Arg Lys Tyr His Arg Lys Gly Tyr Lys
385                 390                 395                 400

Lys Tyr Tyr Gly Gly Gly Ser Ser Ser Ser Glu Glu Tyr Lys Gly Gly
                405                 410                 415

Tyr Tyr Pro Gly Asn Thr Tyr His Tyr His Ser Gly Gly Ser Tyr His
            420                 425                 430

Gly Ser Gly Tyr His Gly Gly Tyr Lys Gly Lys Tyr Tyr Gly Lys Ala
        435                 440                 445

Lys Lys Tyr Tyr Tyr Lys Tyr Lys Asn Ser Gly Lys Tyr Lys Tyr Leu
    450                 455                 460

Lys Lys Ala Arg Lys Tyr His Arg Lys Gly Tyr Lys Lys Tyr Tyr Gly
465                 470                 475                 480

Gly Gly Ser Ser
```

<210> SEQ ID NO 70

```
<211> LENGTH: 788
<212> TYPE: PRT
<213> ORGANISM: Artificial Sequence
<220> FEATURE:
<223> OTHER INFORMATION: MFP[Mgfp5]4-EBPPI[G1A4F1]6-MFP[Mgfp5]4

<400> SEQUENCE: 70

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser Ser Ser Glu Glu
65                  70                  75                  80

Tyr Lys Gly Gly Tyr Tyr Pro Gly Asn Thr Tyr His Tyr His Ser Gly
                85                  90                  95

Gly Ser Tyr His Gly Ser Gly Tyr His Gly Gly Tyr Lys Gly Lys Tyr
            100                 105                 110

Tyr Gly Lys Ala Lys Lys Tyr Tyr Tyr Lys Tyr Lys Asn Ser Gly Lys
        115                 120                 125

Tyr Lys Tyr Leu Lys Lys Ala Arg Lys Tyr His Arg Lys Gly Tyr Lys
    130                 135                 140

Lys Tyr Tyr Gly Gly Gly Ser Ser Ser Ser Glu Glu Tyr Lys Gly Gly
145                 150                 155                 160

Tyr Tyr Pro Gly Asn Thr Tyr His Tyr His Ser Gly Gly Ser Tyr His
                165                 170                 175

Gly Ser Gly Tyr His Gly Gly Tyr Lys Gly Lys Tyr Tyr Gly Lys Ala
            180                 185                 190

Lys Lys Tyr Tyr Tyr Lys Tyr Lys Asn Ser Gly Lys Tyr Lys Tyr Leu
        195                 200                 205

Lys Lys Ala Arg Lys Tyr His Arg Lys Gly Tyr Lys Lys Tyr Tyr Gly
    210                 215                 220

Gly Gly Ser Ser Ser Ser Glu Glu Tyr Lys Gly Gly Tyr Tyr Pro Gly
225                 230                 235                 240

Asn Thr Tyr His Tyr His Ser Gly Gly Ser Tyr His Gly Ser Gly Tyr
                245                 250                 255

His Gly Gly Tyr Lys Gly Lys Tyr Tyr Gly Lys Ala Lys Lys Tyr Tyr
            260                 265                 270

Tyr Lys Tyr Lys Asn Ser Gly Lys Tyr Lys Tyr Leu Lys Lys Ala Arg
        275                 280                 285

Lys Tyr His Arg Lys Gly Tyr Lys Lys Tyr Tyr Gly Gly Gly Ser Ser
    290                 295                 300

Ile Pro Ala Ala Gly Ile Pro Ala Gly Gly Ile Pro Ala Ala Gly Ile
305                 310                 315                 320

Pro Ala Ala Gly Ile Pro Ala Phe Gly Ile Pro Ala Ala Gly Ile Pro
                325                 330                 335

Ala Ala Gly Ile Pro Ala Gly Gly Ile Pro Ala Ala Gly Ile Pro Ala
            340                 345                 350

Ala Gly Ile Pro Ala Phe Gly Ile Pro Ala Ala Gly Ile Pro Ala Ala
        355                 360                 365

Gly Ile Pro Ala Gly Gly Ile Pro Ala Ala Gly Ile Pro Ala Ala Gly
    370                 375                 380
```

```
Ile Pro Ala Phe Gly Ile Pro Ala Ala Gly Ile Pro Ala Ala Gly Ile
385                 390                 395                 400

Pro Ala Gly Gly Ile Pro Ala Ala Gly Ile Pro Ala Ala Gly Ile Pro
                405                 410                 415

Ala Phe Gly Ile Pro Ala Ala Gly Ile Pro Ala Ala Gly Ile Pro Ala
            420                 425                 430

Gly Gly Ile Pro Ala Ala Gly Ile Pro Ala Ala Gly Ile Pro Ala Phe
        435                 440                 445

Gly Ile Pro Ala Ala Gly Ile Pro Ala Ala Gly Ile Pro Ala Gly Gly
    450                 455                 460

Ile Pro Ala Ala Gly Ile Pro Ala Ala Gly Ile Pro Ala Phe Gly Ile
465                 470                 475                 480

Pro Ala Ala Gly Ser Ser Glu Glu Tyr Lys Gly Gly Tyr Tyr Pro Gly
                485                 490                 495

Asn Thr Tyr His Tyr His Ser Gly Gly Ser Tyr His Gly Ser Gly Tyr
            500                 505                 510

His Gly Gly Tyr Lys Gly Lys Tyr Tyr Gly Lys Ala Lys Lys Tyr Tyr
        515                 520                 525

Tyr Lys Tyr Lys Asn Ser Gly Lys Tyr Lys Tyr Leu Lys Lys Ala Arg
    530                 535                 540

Lys Tyr His Arg Lys Gly Tyr Lys Lys Tyr Tyr Gly Gly Gly Ser Ser
545                 550                 555                 560

Ser Ser Glu Glu Tyr Lys Gly Gly Tyr Tyr Pro Gly Asn Thr Tyr His
                565                 570                 575

Tyr His Ser Gly Gly Ser Tyr His Gly Ser Gly Tyr His Gly Gly Tyr
            580                 585                 590

Lys Gly Lys Tyr Tyr Gly Lys Ala Lys Lys Tyr Tyr Tyr Lys Tyr Lys
        595                 600                 605

Asn Ser Gly Lys Tyr Lys Tyr Leu Lys Lys Ala Arg Lys Tyr His Arg
    610                 615                 620

Lys Gly Tyr Lys Lys Tyr Tyr Gly Gly Gly Ser Ser Ser Ser Glu Glu
625                 630                 635                 640

Tyr Lys Gly Gly Tyr Tyr Pro Gly Asn Thr Tyr His Tyr His Ser Gly
                645                 650                 655

Gly Ser Tyr His Gly Ser Gly Tyr His Gly Gly Tyr Lys Gly Lys Tyr
            660                 665                 670

Tyr Gly Lys Ala Lys Lys Tyr Tyr Tyr Lys Tyr Lys Asn Ser Gly Lys
        675                 680                 685

Tyr Lys Tyr Leu Lys Lys Ala Arg Lys Tyr His Arg Lys Gly Tyr Lys
    690                 695                 700

Lys Tyr Tyr Gly Gly Gly Ser Ser Ser Ser Glu Glu Tyr Lys Gly Gly
705                 710                 715                 720

Tyr Tyr Pro Gly Asn Thr Tyr His Tyr His Ser Gly Gly Ser Tyr His
                725                 730                 735

Gly Ser Gly Tyr His Gly Gly Tyr Lys Gly Lys Tyr Tyr Gly Lys Ala
            740                 745                 750

Lys Lys Tyr Tyr Tyr Lys Tyr Lys Asn Ser Gly Lys Tyr Lys Tyr Leu
        755                 760                 765

Lys Lys Ala Arg Lys Tyr His Arg Lys Gly Tyr Lys Lys Tyr Tyr Gly
    770                 775                 780

Gly Gly Ser Ser
785
```

<210> SEQ ID NO 71
<211> LENGTH: 2388
<212> TYPE: DNA
<213> ORGANISM: Artificial Sequence
<220> FEATURE:
<223> OTHER INFORMATION: MFP[Mgfp5]1-EBPP[G1A3F2]24

<400> SEQUENCE: 71
tctagtgaag aatataaagg tggttattac cccggcaaca cctatcatta tcatagtggg 60
ggcagttatc acggcagcgg ctaccatggc ggctataaag gtaaatacta cggtaaagcg 120
aaaaaatact attataaata caaaaacagc ggcaaatata agtacctgaa aaaagctcgt 180
aaataccatc gtaaaggcta taaaaaatat tacggcggcg gcagttcggt gccggcggcg 240
ggcgttccag cctttggtgt gccagcggcg ggagttccgg ccggtggcgt gccggcagcg 300
ggcgtgccgg cttttggcgt gccggcggcg ggcgttccag cctttggtgt gccagcggcg 360
ggagttccgg ccggtggcgt gccggcagcg ggcgtgccgg cttttggcgt gccggcggcg 420
ggcgttccag cctttggtgt gccagcggcg ggagttccgg ccggtggcgt gccggcagcg 480
ggcgtgccgg cttttggcgt gccggcggcg ggcgttccag cctttggtgt gccagcggcg 540
ggagttccgg ccggtggcgt gccggcagcg ggcgtgccgg cttttggcgt gccggcggcg 600
ggcgttccag cctttggtgt gccagcggcg ggagttccgg ccggtggcgt gccggcagcg 660
ggcgtgccgg cttttggcgt gccggcggcg ggcgttccag cctttggtgt gccagcggcg 720
ggagttccgg ccggtggcgt gccggcagcg ggcgtgccgg cttttggcgt gccggcggcg 780
ggcgttccag cctttggtgt gccagcggcg ggagttccgg ccggtggcgt gccggcagcg 840
ggcgtgccgg cttttggcgt gccggcggcg ggcgttccag cctttggtgt gccagcggcg 900
ggagttccgg ccggtggcgt gccggcagcg ggcgtgccgg cttttggcgt gccggcggcg 960
ggcgttccag cctttggtgt gccagcggcg ggagttccgg ccggtggcgt gccggcagcg 1020
ggcgtgccgg cttttggcgt gccggcggcg ggcgttccag cctttggtgt gccagcggcg 1080
ggagttccgg ccggtggcgt gccggcagcg ggcgtgccgg cttttggcgt gccggcggcg 1140
ggcgttccag cctttggtgt gccagcggcg ggagttccgg ccggtggcgt gccggcagcg 1200
ggcgtgccgg cttttggcgt gccggcggcg ggcgttccag cctttggtgt gccagcggcg 1260
ggagttccgg ccggtggcgt gccggcagcg ggcgtgccgg cttttggcgt gccggcggcg 1320
ggcgttccag cctttggtgt gccagcggcg ggagttccgg ccggtggcgt gccggcagcg 1380
ggcgtgccgg cttttggcgt gccggcggcg ggcgttccag cctttggtgt gccagcggcg 1440
ggagttccgg ccggtggcgt gccggcagcg ggcgtgccgg cttttggcgt gccggcggcg 1500
ggcgttccag cctttggtgt gccagcggcg ggagttccgg ccggtggcgt gccggcagcg 1560
ggcgtgccgg cttttggcgt gccggcggcg ggcgttccag cctttggtgt gccagcggcg 1620
ggagttccgg ccggtggcgt gccggcagcg ggcgtgccgg cttttggcgt gccggcggcg 1680
ggcgttccag cctttggtgt gccagcggcg ggagttccgg ccggtggcgt gccggcagcg 1740
ggcgtgccgg cttttggcgt gccggcggcg ggcgttccag cctttggtgt gccagcggcg 1800
ggagttccgg ccggtggcgt gccggcagcg ggcgtgccgg cttttggcgt gccggcggcg 1860
ggcgttccag cctttggtgt gccagcggcg ggagttccgg ccggtggcgt gccggcagcg 1920
ggcgtgccgg cttttggcgt gccggcggcg ggcgttccag cctttggtgt gccagcggcg 1980
ggagttccgg ccggtggcgt gccggcagcg ggcgtgccgg cttttggcgt gccggcggcg 2040
ggcgttccag cctttggtgt gccagcggcg ggagttccgg ccggtggcgt gccggcagcg 2100

```
ggcgtgccgg cttttggcgt gccggcggcg ggcgttccag cctttggtgt gccagcggcg   2160

ggagttccgg ccggtggcgt gccggcagcg ggcgtgccgg cttttggcgt gccggcggcg   2220

ggcgttccag cctttggtgt gccagcggcg ggagttccgg ccggtggcgt gccggcagcg   2280

ggcgtgccgg cttttggcgt gccggcggcg ggcgttccag cctttggtgt gccagcggcg   2340

ggagttccgg ccggtggcgt gccggcagcg ggcgtgccgg cttttggc                2388
```

<210> SEQ ID NO 72
<211> LENGTH: 2616
<212> TYPE: DNA
<213> ORGANISM: Artificial Sequence
<220> FEATURE:
<223> OTHER INFORMATION: MFP[Mgfp5]2-EBPP[G1A3F2]24

<400> SEQUENCE: 72

```
tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgtc tagtgaagaa    240

tataaaggtg gttattaccc cggcaacacc tatcattatc atagtggggg cagttatcac    300

ggcagcggct accatggcgg ctataaaggt aaatactacg gtaaagcgaa aaaatactat    360

tataaataca aaaacagcgg caaatataag tacctgaaaa aagctcgtaa ataccatcgt    420

aaaggctata aaaaatatta cggcggcggc agttcggtgc cggcggcggg cgttccagcc    480

tttggtgtgc cagcggcggg agttccggcc ggtggcgtgc cggcagcggg cgtgccggct    540

tttggcgtgc cggcggcggg cgttccagcc tttggtgtgc cagcggcggg agttccggcc    600

ggtggcgtgc cggcagcggg cgtgccggct tttggcgtgc cggcggcggg cgttccagcc    660

tttggtgtgc cagcggcggg agttccggcc ggtggcgtgc cggcagcggg cgtgccggct    720

tttggcgtgc cggcggcggg cgttccagcc tttggtgtgc cagcggcggg agttccggcc    780

ggtggcgtgc cggcagcggg cgtgccggct tttggcgtgc cggcggcggg cgttccagcc    840

tttggtgtgc cagcggcggg agttccggcc ggtggcgtgc cggcagcggg cgtgccggct    900

tttggcgtgc cggcggcggg cgttccagcc tttggtgtgc cagcggcggg agttccggcc    960

ggtggcgtgc cggcagcggg cgtgccggct tttggcgtgc cggcggcggg cgttccagcc   1020

tttggtgtgc cagcggcggg agttccggcc ggtggcgtgc cggcagcggg cgtgccggct   1080

tttggcgtgc cggcggcggg cgttccagcc tttggtgtgc cagcggcggg agttccggcc   1140

ggtggcgtgc cggcagcggg cgtgccggct tttggcgtgc cggcggcggg cgttccagcc   1200

tttggtgtgc cagcggcggg agttccggcc ggtggcgtgc cggcagcggg cgtgccggct   1260

tttggcgtgc cggcggcggg cgttccagcc tttggtgtgc cagcggcggg agttccggcc   1320

ggtggcgtgc cggcagcggg cgtgccggct tttggcgtgc cggcggcggg cgttccagcc   1380

tttggtgtgc cagcggcggg agttccggcc ggtggcgtgc cggcagcggg cgtgccggct   1440

tttggcgtgc cggcggcggg cgttccagcc tttggtgtgc cagcggcggg agttccggcc   1500

ggtggcgtgc cggcagcggg cgtgccggct tttggcgtgc cggcggcggg cgttccagcc   1560

tttggtgtgc cagcggcggg agttccggcc ggtggcgtgc cggcagcggg cgtgccggct   1620

tttggcgtgc cggcggcggg cgttccagcc tttggtgtgc cagcggcggg agttccggcc   1680

ggtggcgtgc cggcagcggg cgtgccggct tttggcgtgc cggcggcggg cgttccagcc   1740
```

```
tttggtgtgc cagcggcggg agttccggcc ggtggcgtgc cggcagcggg cgtgccggct   1800

tttggcgtgc cggcggcggg cgttccagcc tttggtgtgc cagcggcggg agttccggcc   1860

ggtggcgtgc cggcagcggg cgtgccggct tttggcgtgc cggcggcggg cgttccagcc   1920

tttggtgtgc cagcggcggg agttccggcc ggtggcgtgc cggcagcggg cgtgccggct   1980

tttggcgtgc cggcggcggg cgttccagcc tttggtgtgc cagcggcggg agttccggcc   2040

ggtggcgtgc cggcagcggg cgtgccggct tttggcgtgc cggcggcggg cgttccagcc   2100

tttggtgtgc cagcggcggg agttccggcc ggtggcgtgc cggcagcggg cgtgccggct   2160

tttggcgtgc cggcggcggg cgttccagcc tttggtgtgc cagcggcggg agttccggcc   2220

ggtggcgtgc cggcagcggg cgtgccggct tttggcgtgc cggcggcggg cgttccagcc   2280

tttggtgtgc cagcggcggg agttccggcc ggtggcgtgc cggcagcggg cgtgccggct   2340

tttggcgtgc cggcggcggg cgttccagcc tttggtgtgc cagcggcggg agttccggcc   2400

ggtggcgtgc cggcagcggg cgtgccggct tttggcgtgc cggcggcggg cgttccagcc   2460

tttggtgtgc cagcggcggg agttccggcc ggtggcgtgc cggcagcggg cgtgccggct   2520

tttggcgtgc cggcggcggg cgttccagcc tttggtgtgc cagcggcggg agttccggcc   2580

ggtggcgtgc cggcagcggg cgtgccggct tttggc                             2616
```

<210> SEQ ID NO 73
<211> LENGTH: 3072
<212> TYPE: DNA
<213> ORGANISM: Artificial Sequence
<220> FEATURE:
<223> OTHER INFORMATION: MFP[Mgfp5]4-EBPP[G1A3F2]24

<400> SEQUENCE: 73

```
tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgtc tagtgaagaa    240

tataaaggtg gttattaccc cggcaacacc tatcattatc atagtggggg cagttatcac    300

ggcagcggct accatggcgg ctataaaggt aaatactacg gtaaagcgaa aaaatactat    360

tataaataca aaaacagcgg caaatataag tacctgaaaa aagctcgtaa ataccatcgt    420

aaaggctata aaaaatatta cggcggcggc agttcgtcta gtgaagaata taaaggtggt    480

tattaccccg gcaacaccta tcattatcat agtgggggca gttatcacgg cagcggctac    540

catggcggct ataaaggtaa atactacggt aaagcgaaaa aatactatta taaatacaaa    600

aacagcggca aatataagta cctgaaaaaa gctcgtaaat accatcgtaa aggctataaa    660

aaatattacg gcggcggcag ttcgtctagt gaagaatata aaggtggtta ttaccccggc    720

aacacctatc attatcatag tgggggcagt tatcacggca gcggctacca tggcggctat    780

aaaggtaaat actacggtaa agcgaaaaaa tactattata aatacaaaaa cagcggcaaa    840

tataagtacc tgaaaaaagc tcgtaaatac catcgtaaag gctataaaaa atattacggc    900

ggcggcagtt cggtgccggc ggcgggcgtt ccagcctttg gtgtgccagc ggcgggagtt    960

ccggccggtg gcgtgccggc agcgggcgtg ccggcttttg gcgtgccggc ggcgggcgtt   1020

ccagcctttg gtgtgccagc ggcgggagtt ccggccggtg gcgtgccggc agcgggcgtg   1080

ccggcttttg gcgtgccggc ggcgggcgtt ccagcctttg gtgtgccagc ggcgggagtt   1140

ccggccggtg gcgtgccggc agcgggcgtg ccggcttttg gcgtgccggc ggcgggcgtt   1200
```

```
ccagcctttg gtgtgccagc ggcgggagtt ccggccggtg gcgtgccggc agcgggcgtg   1260

ccggcttttg gcgtgccggc ggcgggcgtt ccagcctttg gtgtgccagc ggcgggagtt   1320

ccggccggtg gcgtgccggc agcgggcgtg ccggcttttg gcgtgccggc ggcgggcgtt   1380

ccagcctttg gtgtgccagc ggcgggagtt ccggccggtg gcgtgccggc agcgggcgtg   1440

ccggcttttg gcgtgccggc ggcgggcgtt ccagcctttg gtgtgccagc ggcgggagtt   1500

ccggccggtg gcgtgccggc agcgggcgtg ccggcttttg gcgtgccggc ggcgggcgtt   1560

ccagcctttg gtgtgccagc ggcgggagtt ccggccggtg gcgtgccggc agcgggcgtg   1620

ccggcttttg gcgtgccggc ggcgggcgtt ccagcctttg gtgtgccagc ggcgggagtt   1680

ccggccggtg gcgtgccggc agcgggcgtg ccggcttttg gcgtgccggc ggcgggcgtt   1740

ccagcctttg gtgtgccagc ggcgggagtt ccggccggtg gcgtgccggc agcgggcgtg   1800

ccggcttttg gcgtgccggc ggcgggcgtt ccagcctttg gtgtgccagc ggcgggagtt   1860

ccggccggtg gcgtgccggc agcgggcgtg ccggcttttg gcgtgccggc ggcgggcgtt   1920

ccagcctttg gtgtgccagc ggcgggagtt ccggccggtg gcgtgccggc agcgggcgtg   1980

ccggcttttg gcgtgccggc ggcgggcgtt ccagcctttg gtgtgccagc ggcgggagtt   2040

ccggccggtg gcgtgccggc agcgggcgtg ccggcttttg gcgtgccggc ggcgggcgtt   2100

ccagcctttg gtgtgccagc ggcgggagtt ccggccggtg gcgtgccggc agcgggcgtg   2160

ccggcttttg gcgtgccggc ggcgggcgtt ccagcctttg gtgtgccagc ggcgggagtt   2220

ccggccggtg gcgtgccggc agcgggcgtg ccggcttttg gcgtgccggc ggcgggcgtt   2280

ccagcctttg gtgtgccagc ggcgggagtt ccggccggtg gcgtgccggc agcgggcgtg   2340

ccggcttttg gcgtgccggc ggcgggcgtt ccagcctttg gtgtgccagc ggcgggagtt   2400

ccggccggtg gcgtgccggc agcgggcgtg ccggcttttg gcgtgccggc ggcgggcgtt   2460

ccagcctttg gtgtgccagc ggcgggagtt ccggccggtg gcgtgccggc agcgggcgtg   2520

ccggcttttg gcgtgccggc ggcgggcgtt ccagcctttg gtgtgccagc ggcgggagtt   2580

ccggccggtg gcgtgccggc agcgggcgtg ccggcttttg gcgtgccggc ggcgggcgtt   2640

ccagcctttg gtgtgccagc ggcgggagtt ccggccggtg gcgtgccggc agcgggcgtg   2700

ccggcttttg gcgtgccggc ggcgggcgtt ccagcctttg gtgtgccagc ggcgggagtt   2760

ccggccggtg gcgtgccggc agcgggcgtg ccggcttttg gcgtgccggc ggcgggcgtt   2820

ccagcctttg gtgtgccagc ggcgggagtt ccggccggtg gcgtgccggc agcgggcgtg   2880

ccggcttttg gcgtgccggc ggcgggcgtt ccagcctttg gtgtgccagc ggcgggagtt   2940

ccggccggtg gcgtgccggc agcgggcgtg ccggcttttg gcgtgccggc ggcgggcgtt   3000

ccagcctttg gtgtgccagc ggcgggagtt ccggccggtg gcgtgccggc agcgggcgtg   3060

ccggcttttg gc                                                       3072
```

<210> SEQ ID NO 74
<211> LENGTH: 768
<212> TYPE: DNA
<213> ORGANISM: Artificial Sequence
<220> FEATURE:
<223> OTHER INFORMATION: MFP[Mgfp5]1-EBPPI[G1A3F2]6

<400> SEQUENCE: 74

```
tctagtgaag aatataaagg tggttattac cccggcaaca cctatcatta tcatagtggg     60

ggcagttatc acggcagcgg ctaccatggc ggctataaag gtaaatacta cggtaaagcg    120
```

```
aaaaaatact attataaata caaaaacagc ggcaaatata agtacctgaa aaaagctcgt    180

aaataccatc gtaaaggcta taaaaaatat tacggcggcg gcagttcgat tccggccgca    240

ggcattcctg catttggtat tccggcggca ggcattcctg ccggtggcat cccggcagcg    300

ggcattccgg cctttggcat tccggccgca ggcattcctg catttggtat tccggcggca    360

ggcattcctg ccggtggcat cccggcagcg ggcattccgg cctttggcat tccggccgca    420

ggcattcctg catttggtat tccggcggca ggcattcctg ccggtggcat cccggcagcg    480

ggcattccgg cctttggcat tccggccgca ggcattcctg catttggtat tccggcggca    540

ggcattcctg ccggtggcat cccggcagcg ggcattccgg cctttggcat tccggccgca    600

ggcattcctg catttggtat tccggcggca ggcattcctg ccggtggcat cccggcagcg    660

ggcattccgg cctttggcat tccggccgca ggcattcctg catttggtat tccggcggca    720

ggcattcctg ccggtggcat cccggcagcg ggcattccgg cctttggc                 768


<210> SEQ ID NO 75
<211> LENGTH: 996
<212> TYPE: DNA
<213> ORGANISM: Artificial Sequence
<220> FEATURE:
<223> OTHER INFORMATION: MFP[Mgfp5]2-EBPPI[G1A3F2]6

<400> SEQUENCE: 75

tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgtc tagtgaagaa    240

tataaaggtg gttattaccc cggcaacacc tatcattatc atagtggggg cagttatcac    300

ggcagcggct accatggcgg ctataaaggt aaatactacg gtaaagcgaa aaaatactat    360

tataaataca aaaacagcgg caaatataag tacctgaaaa aagctcgtaa ataccatcgt    420

aaaggctata aaaaatatta cggcggcggc agttcgattc cggccgcagg cattcctgca    480

tttggtattc cggcggcagg cattcctgcc ggtggcatcc cggcagcggg cattccggcc    540

tttggcattc cggccgcagg cattcctgca tttggtattc cggcggcagg cattcctgcc    600

ggtggcatcc cggcagcggg cattccggcc tttggcattc cggccgcagg cattcctgca    660

tttggtattc cggcggcagg cattcctgcc ggtggcatcc cggcagcggg cattccggcc    720

tttggcattc cggccgcagg cattcctgca tttggtattc cggcggcagg cattcctgcc    780

ggtggcatcc cggcagcggg cattccggcc tttggcattc cggccgcagg cattcctgca    840

tttggtattc cggcggcagg cattcctgcc ggtggcatcc cggcagcggg cattccggcc    900

tttggcattc cggccgcagg cattcctgca tttggtattc cggcggcagg cattcctgcc    960

ggtggcatcc cggcagcggg cattccggcc tttggc                              996


<210> SEQ ID NO 76
<211> LENGTH: 1452
<212> TYPE: DNA
<213> ORGANISM: Artificial Sequence
<220> FEATURE:
<223> OTHER INFORMATION: MFP[Mgfp5]4-EBPPI[G1A3F2]6

<400> SEQUENCE: 76

tctagtgaag aatataaagg tggttattac cccggcaaca cctatcatta tcatagtggg     60

ggcagttatc acggcagcgg ctaccatggc ggctataaag gtaaatacta cggtaaagcg    120
```

```
aaaaaatact attataaata caaaaacagc ggcaaatata agtacctgaa aaaagctcgt    180

aaataccatc gtaaaggcta taaaaaatat tacggcggcg gcagttcgtc tagtgaagaa    240

tataaaggtg gttattaccc cggcaacacc tatcattatc atagtggggg cagttatcac    300

ggcagcggct accatggcgg ctataaaggt aaatactacg gtaaagcgaa aaaatactat    360

tataaataca aaaacagcgg caaatataag tacctgaaaa aagctcgtaa ataccatcgt    420

aaaggctata aaaaatatta cggcggcggc agttcgtcta gtgaagaata taaaggtggt    480

tattaccccg gcaacaccta tcattatcat agtgggggca gttatcacgg cagcggctac    540

catggcggct ataaaggtaa atactacggt aaagcgaaaa aatactatta taaatacaaa    600

aacagcggca aatataagta cctgaaaaaa gctcgtaaat accatcgtaa aggctataaa    660

aaatattacg gcggcggcag ttcgtctagt gaagaatata aaggtggtta ttaccccggc    720

aacacctatc attatcatag tgggggcagt tatcacggca gcggctacca tggcggctat    780

aaaggtaaat actacggtaa agcgaaaaaa tactattata aatacaaaaa cagcggcaaa    840

tataagtacc tgaaaaaagc tcgtaaatac catcgtaaag gctataaaaa atattacggc    900

ggcggcagtt cgattccggc cgcaggcatt cctgcatttg gtattccggc ggcaggcatt    960

cctgccggtg gcatcccggc agcgggcatt ccggcctttg gcattccggc cgcaggcatt   1020

cctgcatttg gtattccggc ggcaggcatt cctgccggtg gcatcccggc agcgggcatt   1080

ccggcctttg gcattccggc cgcaggcatt cctgcatttg gtattccggc ggcaggcatt   1140

cctgccggtg gcatcccggc agcgggcatt ccggcctttg gcattccggc cgcaggcatt   1200

cctgcatttg gtattccggc ggcaggcatt cctgccggtg gcatcccggc agcgggcatt   1260

ccggcctttg gcattccggc cgcaggcatt cctgcatttg gtattccggc ggcaggcatt   1320

cctgccggtg gcatcccggc agcgggcatt ccggcctttg gcattccggc cgcaggcatt   1380

cctgcatttg gtattccggc ggcaggcatt cctgccggtg gcatcccggc agcgggcatt   1440

ccggcctttg gc                                                       1452
```

<210> SEQ ID NO 77
<211> LENGTH: 768
<212> TYPE: DNA
<213> ORGANISM: Artificial Sequence
<220> FEATURE:
<223> OTHER INFORMATION: MFP[Mgfp5]1-EBPPI[G1A4F1]6

<400> SEQUENCE: 77

```
tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgat tcctgcagcc    240

ggtatcccgg ccggtggcat tccggcagcc ggcattccgg ccgccggcat cccggcattt    300

ggcattcctg cagcaggcat tcctgcagcc ggtatcccgg ccggtggcat tccggcagcc    360

ggcattccgg ccgccggcat cccggcattt ggcattcctg cagcaggcat tcctgcagcc    420

ggtatcccgg ccggtggcat tccggcagcc ggcattccgg ccgccggcat cccggcattt    480

ggcattcctg cagcaggcat tcctgcagcc ggtatcccgg ccggtggcat tccggcagcc    540

ggcattccgg ccgccggcat cccggcattt ggcattcctg cagcaggcat tcctgcagcc    600

ggtatcccgg ccggtggcat tccggcagcc ggcattccgg ccgccggcat cccggcattt    660
```

```
ggcattcctg cagcaggcat tcctgcagcc ggtatcccgg ccggtggcat tccggcagcc    720

ggcattccgg ccgccggcat cccggcattt ggcattcctg cagcaggc                 768


<210> SEQ ID NO 78
<211> LENGTH: 996
<212> TYPE: DNA
<213> ORGANISM: Artificial Sequence
<220> FEATURE:
<223> OTHER INFORMATION: MFP[Mgfp5]2-EBPPI[G1A4F1]6

<400> SEQUENCE: 78

tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgtc tagtgaagaa    240

tataaaggtg gttattaccc cggcaacacc tatcattatc atagtggggg cagttatcac    300

ggcagcggct accatggcgg ctataaaggt aaatactacg gtaaagcgaa aaaatactat    360

tataaataca aaaacagcgg caaatataag tacctgaaaa aagctcgtaa ataccatcgt    420

aaaggctata aaaaatatta cggcggcggc agttcgattc ctgcagccgg tatcccggcc    480

ggtggcattc cggcagccgg cattccggcc gccggcatcc cggcatttgg cattcctgca    540

gcaggcattc ctgcagccgg tatcccggcc ggtggcattc cggcagccgg cattccggcc    600

gccggcatcc cggcatttgg cattcctgca gcaggcattc ctgcagccgg tatcccggcc    660

ggtggcattc cggcagccgg cattccggcc gccggcatcc cggcatttgg cattcctgca    720

gcaggcattc ctgcagccgg tatcccggcc ggtggcattc cggcagccgg cattccggcc    780

gccggcatcc cggcatttgg cattcctgca gcaggcattc ctgcagccgg tatcccggcc    840

ggtggcattc cggcagccgg cattccggcc gccggcatcc cggcatttgg cattcctgca    900

gcaggcattc ctgcagccgg tatcccggcc ggtggcattc cggcagccgg cattccggcc    960

gccggcatcc cggcatttgg cattcctgca gcaggc                              996


<210> SEQ ID NO 79
<211> LENGTH: 1452
<212> TYPE: DNA
<213> ORGANISM: Artificial Sequence
<220> FEATURE:
<223> OTHER INFORMATION: MFP[Mgfp5]4-EBPPI[G1A4F1]6

<400> SEQUENCE: 79

tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgtc tagtgaagaa    240

tataaaggtg gttattaccc cggcaacacc tatcattatc atagtggggg cagttatcac    300

ggcagcggct accatggcgg ctataaaggt aaatactacg gtaaagcgaa aaaatactat    360

tataaataca aaaacagcgg caaatataag tacctgaaaa aagctcgtaa ataccatcgt    420

aaaggctata aaaaatatta cggcggcggc agttcgtcta gtgaagaata taaaggtggt    480

tattaccccg gcaacaccta tcattatcat agtgggggca gttatcacgg cagcggctac    540

catggcggct ataaaggtaa atactacggt aaagcgaaaa aatactatta taaatacaaa    600

aacagcggca aatataagta cctgaaaaaa gctcgtaaat accatcgtaa aggctataaa    660
```

```
aaatattacg gcggcggcag ttcgtctagt gaagaatata aaggtggtta ttaccccggc    720
aacacctatc attatcatag tgggggcagt tatcacggca gcggctacca tggcggctat    780
aaaggtaaat actacggtaa agcgaaaaaa tactattata aatacaaaaa cagcggcaaa    840
tataagtacc tgaaaaaagc tcgtaaatac catcgtaaag gctataaaaa atattacggc    900
ggcggcagtt cgattcctgc agccggtatc ccggccggtg gcattccggc agccggcatt    960
ccggccgccg gcatcccggc atttggcatt cctgcagcag gcattcctgc agccggtatc   1020
ccggccggtg gcattccggc agccggcatt ccggccgccg gcatcccggc atttggcatt   1080
cctgcagcag gcattcctgc agccggtatc ccggccggtg gcattccggc agccggcatt   1140
ccggccgccg gcatcccggc atttggcatt cctgcagcag gcattcctgc agccggtatc   1200
ccggccggtg gcattccggc agccggcatt ccggccgccg gcatcccggc atttggcatt   1260
cctgcagcag gcattcctgc agccggtatc ccggccggtg gcattccggc agccggcatt   1320
ccggccgccg gcatcccggc atttggcatt cctgcagcag gcattcctgc agccggtatc   1380
ccggccggtg gcattccggc agccggcatt ccggccgccg gcatcccggc atttggcatt   1440
cctgcagcag gc                                                       1452
```

<210> SEQ ID NO 80
<211> LENGTH: 1308
<212> TYPE: DNA
<213> ORGANISM: Artificial Sequence
<220> FEATURE:
<223> OTHER INFORMATION: EBPPI[G1A3F2]6-MFP[Mgfp5]1-EBPPI[G1A3F2]6

<400> SEQUENCE: 80

```
attccggccg caggcattcc tgcatttggt attccggcgg caggcattcc tgccggtggc     60
atcccggcag cgggcattcc ggcctttggc attccggccg caggcattcc tgcatttggt    120
attccggcgg caggcattcc tgccggtggc atcccggcag cgggcattcc ggcctttggc    180
attccggccg caggcattcc tgcatttggt attccggcgg caggcattcc tgccggtggc    240
atcccggcag cgggcattcc ggcctttggc attccggccg caggcattcc tgcatttggt    300
attccggcgg caggcattcc tgccggtggc atcccggcag cgggcattcc ggcctttggc    360
attccggccg caggcattcc tgcatttggt attccggcgg caggcattcc tgccggtggc    420
atcccggcag cgggcattcc ggcctttggc attccggccg caggcattcc tgcatttggt    480
attccggcgg caggcattcc tgccggtggc atcccggcag cgggcattcc ggcctttggc    540
tctagtgaag aatataaagg tggttattac cccggcaaca cctatcatta tcatagtggg    600
ggcagttatc acggcagcgg ctaccatggc ggctataaag gtaaatacta cggtaaagcg    660
aaaaaatact attataaata caaaaacagc ggcaaatata agtacctgaa aaaagctcgt    720
aaataccatc gtaaaggcta taaaaaatat tacggcggcg gcagttcgat tccggccgca    780
ggcattcctg catttggtat tccggcggca ggcattcctg ccggtggcat cccggcagcg    840
ggcattccgg cctttggcat tccggccgca ggcattcctg catttggtat tccggcggca    900
ggcattcctg ccggtggcat cccggcagcg ggcattccgg cctttggcat tccggccgca    960
ggcattcctg catttggtat tccggcggca ggcattcctg ccggtggcat cccggcagcg   1020
ggcattccgg cctttggcat tccggccgca ggcattcctg catttggtat tccggcggca   1080
ggcattcctg ccggtggcat cccggcagcg ggcattccgg cctttggcat tccggccgca   1140
ggcattcctg catttggtat tccggcggca ggcattcctg ccggtggcat cccggcagcg   1200
```

```
ggcattccgg cctttggcat tccggccgca ggcattcctg catttggtat tccggcggca   1260

ggcattcctg ccggtggcat cccggcagcg ggcattccgg cctttggc                1308


<210> SEQ ID NO 81
<211> LENGTH: 1536
<212> TYPE: DNA
<213> ORGANISM: Artificial Sequence
<220> FEATURE:
<223> OTHER INFORMATION: EBPPI[G1A3F2]6-MFP[Mgfp5]2-EBPPI[G1A3F2]6

<400> SEQUENCE: 81

attccggccg caggcattcc tgcatttggt attccggcgg caggcattcc tgccggtggc     60

atcccggcag cgggcattcc ggcctttggc attccggccg caggcattcc tgcatttggt    120

attccggcgg caggcattcc tgccggtggc atcccggcag cgggcattcc ggcctttggc    180

attccggccg caggcattcc tgcatttggt attccggcgg caggcattcc tgccggtggc    240

atcccggcag cgggcattcc ggcctttggc attccggccg caggcattcc tgcatttggt    300

attccggcgg caggcattcc tgccggtggc atcccggcag cgggcattcc ggcctttggc    360

attccggccg caggcattcc tgcatttggt attccggcgg caggcattcc tgccggtggc    420

atcccggcag cgggcattcc ggcctttggc attccggccg caggcattcc tgcatttggt    480

attccggcgg caggcattcc tgccggtggc atcccggcag cgggcattcc ggcctttggc    540

tctagtgaag aatataaagg tggttattac cccggcaaca cctatcatta tcatagtggg    600

ggcagttatc acggcagcgg ctaccatggc ggctataaag gtaaatacta cggtaaagcg    660

aaaaaatact attataaata caaaaacagc ggcaaatata agtacctgaa aaaagctcgt    720

aaataccatc gtaaaggcta taaaaaatat tacggcggcg gcagttcgtc tagtgaagaa    780

tataaaggtg gttattaccc cggcaacacc tatcattatc atagtggggg cagttatcac    840

ggcagcggct accatggcgg ctataaaggt aaatactacg gtaaagcgaa aaaatactat    900

tataaataca aaaacagcgg caaatataag tacctgaaaa aagctcgtaa ataccatcgt    960

aaaggctata aaaaatatta cggcggcggc agttcgattc cggccgcagg cattcctgca   1020

tttggtattc cggcggcagg cattcctgcc ggtggcatcc cggcagcggg cattccggcc   1080

tttggcattc cggccgcagg cattcctgca tttggtattc cggcggcagg cattcctgcc   1140

ggtggcatcc cggcagcggg cattccggcc tttggcattc cggccgcagg cattcctgca   1200

tttggtattc cggcggcagg cattcctgcc ggtggcatcc cggcagcggg cattccggcc   1260

tttggcattc cggccgcagg cattcctgca tttggtattc cggcggcagg cattcctgcc   1320

ggtggcatcc cggcagcggg cattccggcc tttggcattc cggccgcagg cattcctgca   1380

tttggtattc cggcggcagg cattcctgcc ggtggcatcc cggcagcggg cattccggcc   1440

tttggcattc cggccgcagg cattcctgca tttggtattc cggcggcagg cattcctgcc   1500

ggtggcatcc cggcagcggg cattccggcc tttggc                             1536


<210> SEQ ID NO 82
<211> LENGTH: 1992
<212> TYPE: DNA
<213> ORGANISM: Artificial Sequence
<220> FEATURE:
<223> OTHER INFORMATION: EBPPI[G1A3F2]6-MFP[Mgfp5]4-EBPPI[G1A3F2]6

<400> SEQUENCE: 82

attccggccg caggcattcc tgcatttggt attccggcgg caggcattcc tgccggtggc     60

atcccggcag cgggcattcc ggcctttggc attccggccg caggcattcc tgcatttggt    120
```

```
attccggcgg caggcattcc tgccggtggc atcccggcag cgggcattcc ggcctttggc    180
attccggccg caggcattcc tgcatttggt attccggcgg caggcattcc tgccggtggc    240
atcccggcag cgggcattcc ggcctttggc attccggccg caggcattcc tgcatttggt    300
attccggcgg caggcattcc tgccggtggc atcccggcag cgggcattcc ggcctttggc    360
attccggccg caggcattcc tgcatttggt attccggcgg caggcattcc tgccggtggc    420
atcccggcag cgggcattcc ggcctttggc attccggccg caggcattcc tgcatttggt    480
attccggcgg caggcattcc tgccggtggc atcccggcag cgggcattcc ggcctttggc    540
tctagtgaag aatataaagg tggttattac cccggcaaca cctatcatta tcatagtggg    600
ggcagttatc acggcagcgg ctaccatggc ggctataaag gtaaatacta cggtaaagcg    660
aaaaaatact attataaata caaaaacagc ggcaaatata agtacctgaa aaaagctcgt    720
aaataccatc gtaaaggcta taaaaaatat tacggcggcg gcagttcgtc tagtgaagaa    780
tataaaggtg gttattaccc cggcaacacc tatcattatc atagtggggg cagttatcac    840
ggcagcggct accatggcgg ctataaaggt aaatactacg gtaaagcgaa aaaatactat    900
tataaataca aaaacagcgg caaatataag tacctgaaaa aagctcgtaa ataccatcgt    960
aaaggctata aaaaatatta cggcggcggc agttcgtcta gtgaagaata taaaggtggt   1020
tattaccccg gcaacaccta tcattatcat agtgggggca gttatcacgg cagcggctac   1080
catggcggct ataaaggtaa atactacggt aaagcgaaaa aatactatta taaatacaaa   1140
aacagcggca aatataagta cctgaaaaaa gctcgtaaat accatcgtaa aggctataaa   1200
aaatattacg gcggcggcag ttcgtctagt gaagaatata aaggtggtta ttaccccggc   1260
aacacctatc attatcatag tgggggcagt tatcacggca gcggctacca tggcggctat   1320
aaaggtaaat actacggtaa agcgaaaaaa tactattata aatacaaaaa cagcggcaaa   1380
tataagtacc tgaaaaaagc tcgtaaatac catcgtaaag gctataaaaa atattacggc   1440
ggcggcagtt cgattccggc cgcaggcatt cctgcatttg gtattccggc ggcaggcatt   1500
cctgccggtg gcatcccggc agcgggcatt ccggcctttg gcattccggc cgcaggcatt   1560
cctgcatttg gtattccggc ggcaggcatt cctgccggtg gcatcccggc agcgggcatt   1620
ccggcctttg gcattccggc cgcaggcatt cctgcatttg gtattccggc ggcaggcatt   1680
cctgccggtg gcatcccggc agcgggcatt ccggcctttg gcattccggc cgcaggcatt   1740
cctgcatttg gtattccggc ggcaggcatt cctgccggtg gcatcccggc agcgggcatt   1800
ccggcctttg gcattccggc cgcaggcatt cctgcatttg gtattccggc ggcaggcatt   1860
cctgccggtg gcatcccggc agcgggcatt ccggcctttg gcattccggc cgcaggcatt   1920
cctgcatttg gtattccggc ggcaggcatt cctgccggtg gcatcccggc agcgggcatt   1980
ccggcctttg gc                                                       1992
```

<210> SEQ ID NO 83
<211> LENGTH: 1308
<212> TYPE: DNA
<213> ORGANISM: Artificial Sequence
<220> FEATURE:
<223> OTHER INFORMATION: EBPPI[G1A4F1]6-MFP[Mgfp5]1-EBPPI[G1A4F1]6

<400> SEQUENCE: 83

```
attcctgcag ccggtatccc ggccggtggc attccggcag ccggcattcc ggccgccggc     60
atcccggcat ttggcattcc tgcagcaggc attcctgcag ccggtatccc ggccggtggc    120
```

```
attccggcag ccggcattcc ggccgccggc atcccggcat ttggcattcc tgcagcaggc    180

attcctgcag ccggtatccc ggccggtggc attccggcag ccggcattcc ggccgccggc    240

atcccggcat ttggcattcc tgcagcaggc attcctgcag ccggtatccc ggccggtggc    300

attccggcag ccggcattcc ggccgccggc atcccggcat ttggcattcc tgcagcaggc    360

attcctgcag ccggtatccc ggccggtggc attccggcag ccggcattcc ggccgccggc    420

atcccggcat ttggcattcc tgcagcaggc attcctgcag ccggtatccc ggccggtggc    480

attccggcag ccggcattcc ggccgccggc atcccggcat ttggcattcc tgcagcaggc    540

tctagtgaag aatataaagg tggttattac cccggcaaca cctatcatta tcatagtggg    600

ggcagttatc acggcagcgg ctaccatggc ggctataaag gtaaatacta cggtaaagcg    660

aaaaaatact attataaata caaaaacagc ggcaaatata agtacctgaa aaaagctcgt    720

aaataccatc gtaaaggcta taaaaaatat tacggcggcg gcagttcgat tcctgcagcc    780

ggtatcccgg ccggtggcat tccggcagcc ggcattccgg ccgccggcat cccggcattt    840

ggcattcctg cagcaggcat tcctgcagcc ggtatcccgg ccggtggcat tccggcagcc    900

ggcattccgg ccgccggcat cccggcattt ggcattcctg cagcaggcat tcctgcagcc    960

ggtatcccgg ccggtggcat tccggcagcc ggcattccgg ccgccggcat cccggcattt   1020

ggcattcctg cagcaggcat tcctgcagcc ggtatcccgg ccggtggcat tccggcagcc   1080

ggcattccgg ccgccggcat cccggcattt ggcattcctg cagcaggcat tcctgcagcc   1140

ggtatcccgg ccggtggcat tccggcagcc ggcattccgg ccgccggcat cccggcattt   1200

ggcattcctg cagcaggcat tcctgcagcc ggtatcccgg ccggtggcat tccggcagcc   1260

ggcattccgg ccgccggcat cccggcattt ggcattcctg cagcaggc                1308
```

<210> SEQ ID NO 84
<211> LENGTH: 1536
<212> TYPE: DNA
<213> ORGANISM: Artificial Sequence
<220> FEATURE:
<223> OTHER INFORMATION: EBPPI[G1A4F1]6-MFP[Mgfp5]2-EBPPI[G1A4F1]6

<400> SEQUENCE: 84

```
attcctgcag ccggtatccc ggccggtggc attccggcag ccggcattcc ggccgccggc     60

atcccggcat ttggcattcc tgcagcaggc attcctgcag ccggtatccc ggccggtggc    120

attccggcag ccggcattcc ggccgccggc atcccggcat ttggcattcc tgcagcaggc    180

attcctgcag ccggtatccc ggccggtggc attccggcag ccggcattcc ggccgccggc    240

atcccggcat ttggcattcc tgcagcaggc attcctgcag ccggtatccc ggccggtggc    300

attccggcag ccggcattcc ggccgccggc atcccggcat ttggcattcc tgcagcaggc    360

attcctgcag ccggtatccc ggccggtggc attccggcag ccggcattcc ggccgccggc    420

atcccggcat ttggcattcc tgcagcaggc attcctgcag ccggtatccc ggccggtggc    480

attccggcag ccggcattcc ggccgccggc atcccggcat ttggcattcc tgcagcaggc    540

tctagtgaag aatataaagg tggttattac cccggcaaca cctatcatta tcatagtggg    600

ggcagttatc acggcagcgg ctaccatggc ggctataaag gtaaatacta cggtaaagcg    660

aaaaaatact attataaata caaaaacagc ggcaaatata agtacctgaa aaaagctcgt    720

aaataccatc gtaaaggcta taaaaaatat tacggcggcg gcagttcgtc tagtgaagaa    780

tataaaggtg gttattaccc cggcaacacc tatcattatc atagtggggg cagttatcac    840

ggcagcggct accatggcgg ctataaaggt aaatactacg gtaaagcgaa aaaatactat    900
```

```
tataaataca aaaacagcgg caaatataag tacctgaaaa aagctcgtaa ataccatcgt    960
aaaggctata aaaaatatta cggcggcggc agttcgattc ctgcagccgg tatcccggcc   1020
ggtggcattc cggcagccgg cattccggcc gccggcatcc cggcatttgg cattcctgca   1080
gcaggcattc ctgcagccgg tatcccggcc ggtggcattc cggcagccgg cattccggcc   1140
gccggcatcc cggcatttgg cattcctgca gcaggcattc ctgcagccgg tatcccggcc   1200
ggtggcattc cggcagccgg cattccggcc gccggcatcc cggcatttgg cattcctgca   1260
gcaggcattc ctgcagccgg tatcccggcc ggtggcattc cggcagccgg cattccggcc   1320
gccggcatcc cggcatttgg cattcctgca gcaggcattc ctgcagccgg tatcccggcc   1380
ggtggcattc cggcagccgg cattccggcc gccggcatcc cggcatttgg cattcctgca   1440
gcaggcattc ctgcagccgg tatcccggcc ggtggcattc cggcagccgg cattccggcc   1500
gccggcatcc cggcatttgg cattcctgca gcaggc                             1536
```

```
<210> SEQ ID NO 85
<211> LENGTH: 1992
<212> TYPE: DNA
<213> ORGANISM: Artificial Sequence
<220> FEATURE:
<223> OTHER INFORMATION: EBPPI[G1A4F1]6-MFP[Mgfp5]4-EBPPI[G1A4F1]6

<400> SEQUENCE: 85

attcctgcag ccggtatccc ggccggtggc attccggcag ccggcattcc ggccgccggc     60
atcccggcat ttggcattcc tgcagcaggc attcctgcag ccggtatccc ggccggtggc    120
attccggcag ccggcattcc ggccgccggc atcccggcat ttggcattcc tgcagcaggc    180
attcctgcag ccggtatccc ggccggtggc attccggcag ccggcattcc ggccgccggc    240
atcccggcat ttggcattcc tgcagcaggc attcctgcag ccggtatccc ggccggtggc    300
attccggcag ccggcattcc ggccgccggc atcccggcat ttggcattcc tgcagcaggc    360
attcctgcag ccggtatccc ggccggtggc attccggcag ccggcattcc ggccgccggc    420
atcccggcat ttggcattcc tgcagcaggc attcctgcag ccggtatccc ggccggtggc    480
attccggcag ccggcattcc ggccgccggc atcccggcat ttggcattcc tgcagcaggc    540
tctagtgaag aatataaagg tggttattac cccggcaaca cctatcatta tcatagtggg    600
ggcagttatc acggcagcgg ctaccatggc ggctataaag gtaaatacta cggtaaagcg    660
aaaaaatact attataaata caaaaacagc ggcaaatata agtacctgaa aaaagctcgt    720
aaataccatc gtaaaggcta taaaaaatat tacggcggcg gcagttcgtc tagtgaagaa    780
tataaaggtg gttattaccc cggcaacacc tatcattatc atagtggggg cagttatcac    840
ggcagcggct accatggcgg ctataaaggt aaatactacg gtaaagcgaa aaaatactat    900
tataaataca aaaacagcgg caaatataag tacctgaaaa aagctcgtaa ataccatcgt    960
aaaggctata aaaaatatta cggcggcggc agttcgtcta gtgaagaata taaaggtggt   1020
tattaccccg gcaacaccta tcattatcat agtgggggca gttatcacgg cagcggctac   1080
catggcggct ataaaggtaa atactacggt aaagcgaaaa aatactatta taaatacaaa   1140
aacagcggca aatataagta cctgaaaaaa gctcgtaaat accatcgtaa aggctataaa   1200
aaatattacg gcggcggcag ttcgtctagt gaagaatata aaggtggtta ttaccccggc   1260
aacacctatc attatcatag tgggggcagt tatcacggca gcggctacca tggcggctat   1320
aaaggtaaat actacggtaa agcgaaaaaa tactattata aatacaaaaa cagcggcaaa   1380
```

```
tataagtacc tgaaaaaagc tcgtaaatac catcgtaaag gctataaaaa atattacggc   1440

ggcggcagtt cgattcctgc agccggtatc ccggccggtg gcattccggc agccggcatt   1500

ccggccgccg gcatcccggc atttggcatt cctgcagcag gcattcctgc agccggtatc   1560

ccggccggtg gcattccggc agccggcatt ccggccgccg gcatcccggc atttggcatt   1620

cctgcagcag gcattcctgc agccggtatc ccggccggtg gcattccggc agccggcatt   1680

ccggccgccg gcatcccggc atttggcatt cctgcagcag gcattcctgc agccggtatc   1740

ccggccggtg gcattccggc agccggcatt ccggccgccg gcatcccggc atttggcatt   1800

cctgcagcag gcattcctgc agccggtatc ccggccggtg gcattccggc agccggcatt   1860

ccggccgccg gcatcccggc atttggcatt cctgcagcag gcattcctgc agccggtatc   1920

ccggccggtg gcattccggc agccggcatt ccggccgccg gcatcccggc atttggcatt   1980

cctgcagcag gc                                                       1992
```

<210> SEQ ID NO 86
<211> LENGTH: 996
<212> TYPE: DNA
<213> ORGANISM: Artificial Sequence
<220> FEATURE:
<223> OTHER INFORMATION: MFP[Mgfp5]1-EBPPI[G1A3F2]6-MFP[Mgfp5]1

<400> SEQUENCE: 86

```
tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaagctcgt    180

aaataccatc gtaaaggcta taaaaaatat tacggcggcg gcagttcgat tccggccgca    240

ggcattcctg catttggtat tccggcggca ggcattcctg ccggtggcat cccggcagcg    300

ggcattccgg cctttggcat tccggccgca ggcattcctg catttggtat tccggcggca    360

ggcattcctg ccggtggcat cccggcagcg ggcattccgg cctttggcat tccggccgca    420

ggcattcctg catttggtat tccggcggca ggcattcctg ccggtggcat cccggcagcg    480

ggcattccgg cctttggcat tccggccgca ggcattcctg catttggtat tccggcggca    540

ggcattcctg ccggtggcat cccggcagcg ggcattccgg cctttggcat tccggccgca    600

ggcattcctg catttggtat tccggcggca ggcattcctg ccggtggcat cccggcagcg    660

ggcattccgg cctttggcat tccggccgca ggcattcctg catttggtat tccggcggca    720

ggcattcctg ccggtggcat cccggcagcg ggcattccgg cctttggctc tagtgaagaa    780

tataaaggtg gttattaccc cggcaacacc tatcattatc atagtggggg cagttatcac    840

ggcagcggct accatggcgg ctataaaggt aaatactacg gtaaagcgaa aaaatactat    900

tataaataca aaaacagcgg caaatataag tacctgaaaa aagctcgtaa ataccatcgt    960

aaaggctata aaaaatatta cggcggcggc agttcg                              996
```

<210> SEQ ID NO 87
<211> LENGTH: 1452
<212> TYPE: DNA
<213> ORGANISM: Artificial Sequence
<220> FEATURE:
<223> OTHER INFORMATION: MFP[Mgfp5]2-EBPPI[G1A3F2]6-MFP[Mgfp5]2

<400> SEQUENCE: 87

```
tctagtgaag aatataaagg tggttattac cccggcaaca cctatcatta tcatagtggg     60

ggcagttatc acggcagcgg ctaccatggc ggctataaag gtaaatacta cggtaaagcg    120
```

```
aaaaaatact attataaata caaaaacagc ggcaaatata agtacctgaa aaaagctcgt    180
aaataccatc gtaaaggcta taaaaaatat tacggcggcg gcagttcgtc tagtgaagaa    240
tataaaggtg gttattaccc cggcaacacc tatcattatc atagtggggg cagttatcac    300
ggcagcggct accatggcgg ctataaaggt aaatactacg gtaaagcgaa aaaatactat    360
tataaataca aaaacagcgg caaatataag tacctgaaaa aagctcgtaa ataccatcgt    420
aaaggctata aaaaatatta cggcggcggc agttcgattc cggccgcagg cattcctgca    480
tttggtattc cggcggcagg cattcctgcc ggtggcatcc cggcagcggg cattccggcc    540
tttggcattc cggccgcagg cattcctgca tttggtattc cggcggcagg cattcctgcc    600
ggtggcatcc cggcagcggg cattccggcc tttggcattc cggccgcagg cattcctgca    660
tttggtattc cggcggcagg cattcctgcc ggtggcatcc cggcagcggg cattccggcc    720
tttggcattc cggccgcagg cattcctgca tttggtattc cggcggcagg cattcctgcc    780
ggtggcatcc cggcagcggg cattccggcc tttggcattc cggccgcagg cattcctgca    840
tttggtattc cggcggcagg cattcctgcc ggtggcatcc cggcagcggg cattccggcc    900
tttggcattc cggccgcagg cattcctgca tttggtattc cggcggcagg cattcctgcc    960
ggtggcatcc cggcagcggg cattccggcc tttggctcta gtgaagaata taaaggtggt   1020
tattaccccg gcaacaccta tcattatcat agtgggggca gttatcacgg cagcggctac   1080
catggcggct ataaaggtaa atactacggt aaagcgaaaa aatactatta taaatacaaa   1140
aacagcggca aatataagta cctgaaaaaa gctcgtaaat accatcgtaa aggctataaa   1200
aaatattacg gcggcggcag ttcgtctagt gaagaatata aaggtggtta ttaccccggc   1260
aacacctatc attatcatag tgggggcagt tatcacggca gcggctacca tggcggctat   1320
aaaggtaaat actacggtaa agcgaaaaaa tactattata aatacaaaaa cagcggcaaa   1380
tataagtacc tgaaaaaagc tcgtaaatac catcgtaaag gctataaaaa atattacggc   1440
ggcggcagtt cg                                                       1452
```

<210> SEQ ID NO 88
<211> LENGTH: 2364
<212> TYPE: DNA
<213> ORGANISM: Artificial Sequence
<220> FEATURE:
<223> OTHER INFORMATION: MFP[Mgfp5]4-EBPPI[G1A3F2]6-MFP[Mgfp5]4

<400> SEQUENCE: 88

```
tctagtgaag aatataaagg tggttattac cccggcaaca cctatcatta tcatagtggg     60
ggcagttatc acggcagcgg ctaccatggc ggctataaag gtaaatacta cggtaaagcg    120
aaaaaatact attataaata caaaaacagc ggcaaatata agtacctgaa aaaagctcgt    180
aaataccatc gtaaaggcta taaaaaatat tacggcggcg gcagttcgtc tagtgaagaa    240
tataaaggtg gttattaccc cggcaacacc tatcattatc atagtggggg cagttatcac    300
ggcagcggct accatggcgg ctataaaggt aaatactacg gtaaagcgaa aaaatactat    360
tataaataca aaaacagcgg caaatataag tacctgaaaa aagctcgtaa ataccatcgt    420
aaaggctata aaaaatatta cggcggcggc agttcgtcta gtgaagaata taaaggtggt    480
tattaccccg gcaacaccta tcattatcat agtgggggca gttatcacgg cagcggctac    540
catggcggct ataaaggtaa atactacggt aaagcgaaaa aatactatta taaatacaaa    600
aacagcggca aatataagta cctgaaaaaa gctcgtaaat accatcgtaa aggctataaa    660
```

```
aaatattacg gcggcggcag ttcgtctagt gaagaatata aaggtggtta ttaccccggc    720

aacacctatc attatcatag tgggggcagt tatcacggca gcggctacca tggcggctat    780

aaaggtaaat actacggtaa agcgaaaaaa tactattata aatacaaaaa cagcggcaaa    840

tataagtacc tgaaaaaagc tcgtaaatac catcgtaaag gctataaaaa atattacggc    900

ggcggcagtt cgattccggc cgcaggcatt cctgcatttg gtattccggc ggcaggcatt    960

cctgccggtg gcatcccggc agcgggcatt ccggcctttg gcattccggc cgcaggcatt   1020

cctgcatttg gtattccggc ggcaggcatt cctgccggtg gcatcccggc agcgggcatt   1080

ccggcctttg gcattccggc cgcaggcatt cctgcatttg gtattccggc ggcaggcatt   1140

cctgccggtg gcatcccggc agcgggcatt ccggcctttg gcattccggc cgcaggcatt   1200

cctgcatttg gtattccggc ggcaggcatt cctgccggtg gcatcccggc agcgggcatt   1260

ccggcctttg gcattccggc cgcaggcatt cctgcatttg gtattccggc ggcaggcatt   1320

cctgccggtg gcatcccggc agcgggcatt ccggcctttg gcattccggc cgcaggcatt   1380

cctgcatttg gtattccggc ggcaggcatt cctgccggtg gcatcccggc agcgggcatt   1440

ccggcctttg gctctagtga agaatataaa ggtggttatt accccggcaa cacctatcat   1500

tatcatagtg ggggcagtta tcacggcagc ggctaccatg gcggctataa aggtaaatac   1560

tacggtaaag cgaaaaaata ctattataaa tacaaaaaca gcggcaaata taagtacctg   1620

aaaaaagctc gtaaatacca tcgtaaaggc tataaaaaat attacggcgg cggcagttcg   1680

tctagtgaag aatataaagg tggttattac cccggcaaca cctatcatta tcatagtggg   1740

ggcagttatc acggcagcgg ctaccatggc ggctataaag gtaaatacta cggtaaagcg   1800

aaaaaatact attataaata caaaaacagc ggcaaatata agtacctgaa aaaagctcgt   1860

aaataccatc gtaaaggcta taaaaaatat tacggcggcg gcagttcgtc tagtgaagaa   1920

tataaaggtg gttattaccc cggcaacacc tatcattatc atagtggggg cagttatcac   1980

ggcagcggct accatggcgg ctataaaggt aaatactacg gtaaagcgaa aaaatactat   2040

tataaataca aaaacagcgg caaatataag tacctgaaaa aagctcgtaa ataccatcgt   2100

aaaggctata aaaaatatta cggcggcggc agttcgtcta gtgaagaata taaaggtggt   2160

tattaccccg gcaacaccta tcattatcat agtgggggca gttatcacgg cagcggctac   2220

catggcggct ataaaggtaa atactacggt aaagcgaaaa aatactatta taaatacaaa   2280

aacagcggca aatataagta cctgaaaaaa gctcgtaaat accatcgtaa aggctataaa   2340

aaatattacg gcggcggcag ttcg                                           2364
```

```
<210> SEQ ID NO 89
<211> LENGTH: 996
<212> TYPE: DNA
<213> ORGANISM: Artificial Sequence
<220> FEATURE:
<223> OTHER INFORMATION: MFP[Mgfp5]1-EBPPI[G1A4F1]6-MFP[Mgfp5]1

<400> SEQUENCE: 89

tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgat tcctgcagcc    240

ggtatcccgg ccggtggcat tccggcagcc ggcattccgg ccgccggcat cccggcattt    300

ggcattcctg cagcaggcat tcctgcagcc ggtatcccgg ccggtggcat tccggcagcc    360
```

```
ggcattccgg ccgccggcat cccggcattt ggcattcctg cagcaggcat tcctgcagcc    420
ggtatcccgg ccggtggcat tccggcagcc ggcattccgg ccgccggcat cccggcattt    480
ggcattcctg cagcaggcat tcctgcagcc ggtatcccgg ccggtggcat tccggcagcc    540
ggcattccgg ccgccggcat cccggcattt ggcattcctg cagcaggcat tcctgcagcc    600
ggtatcccgg ccggtggcat tccggcagcc ggcattccgg ccgccggcat cccggcattt    660
ggcattcctg cagcaggcat tcctgcagcc ggtatcccgg ccggtggcat tccggcagcc    720
ggcattccgg ccgccggcat cccggcattt ggcattcctg cagcaggctc tagtgaagaa    780
tataaaggtg gttattaccc cggcaacacc tatcattatc atagtggggg cagttatcac    840
ggcagcggct accatggcgg ctataaaggt aaatactacg gtaaagcgaa aaaatactat    900
tataaataca aaaacagcgg caaatataag tacctgaaaa aagctcgtaa ataccatcgt    960
aaaggctata aaaaatatta cggcggcggc agttcg                              996
```

<210> SEQ ID NO 90
<211> LENGTH: 1452
<212> TYPE: DNA
<213> ORGANISM: Artificial Sequence
<220> FEATURE:
<223> OTHER INFORMATION: MFP[Mgfp5]2-EBPPI[G1A4F1]6MFP[Mgfp5]2

<400> SEQUENCE: 90

```
tctagtgaag aatataaagg tggttattac cccggcaaca cctatcatta tcatagtggg     60
ggcagttatc acggcagcgg ctaccatggc ggctataaag gtaaatacta cggtaaagcg    120
aaaaaatact attataaata caaaaacagc ggcaaatata agtacctgaa aaaagctcgt    180
aaataccatc gtaaaggcta taaaaaatat tacggcggcg gcagttcgtc tagtgaagaa    240
tataaaggtg gttattaccc cggcaacacc tatcattatc atagtggggg cagttatcac    300
ggcagcggct accatggcgg ctataaaggt aaatactacg gtaaagcgaa aaaatactat    360
tataaataca aaaacagcgg caaatataag tacctgaaaa aagctcgtaa ataccatcgt    420
aaaggctata aaaaatatta cggcggcggc agttcgattc ctgcagccgg tatcccggcc    480
ggtggcattc cggcagccgg cattccggcc gccggcatcc cggcatttgg cattcctgca    540
gcaggcattc ctgcagccgg tatcccggcc ggtggcattc cggcagccgg cattccggcc    600
gccggcatcc cggcatttgg cattcctgca gcaggcattc ctgcagccgg tatcccggcc    660
ggtggcattc cggcagccgg cattccggcc gccggcatcc cggcatttgg cattcctgca    720
gcaggcattc ctgcagccgg tatcccggcc ggtggcattc cggcagccgg cattccggcc    780
gccggcatcc cggcatttgg cattcctgca gcaggcattc ctgcagccgg tatcccggcc    840
ggtggcattc cggcagccgg cattccggcc gccggcatcc cggcatttgg cattcctgca    900
gcaggcattc ctgcagccgg tatcccggcc ggtggcattc cggcagccgg cattccggcc    960
gccggcatcc cggcatttgg cattcctgca gcaggctcta gtgaagaata taaaggtggt   1020
tattaccccg gcaacaccta tcattatcat agtgggggca gttatcacgg cagcggctac   1080
catggcggct ataaaggtaa atactacggt aaagcgaaaa aatactatta taaatacaaa   1140
aacagcggca aatataagta cctgaaaaaa gctcgtaaat accatcgtaa aggctataaa   1200
aaatattacg gcggcggcag ttcgtctagt gaagaatata aaggtggtta ttaccccggc   1260
aacacctatc attatcatag tgggggcagt tatcacggca gcggctacca tggcggctat   1320
aaaggtaaat actacggtaa agcgaaaaaa tactattata aatacaaaaa cagcggcaaa   1380
```

```
tataagtacc tgaaaaaagc tcgtaaatac catcgtaaag gctataaaaa atattacggc   1440

ggcggcagtt cg                                                       1452


<210> SEQ ID NO 91
<211> LENGTH: 2364
<212> TYPE: DNA
<213> ORGANISM: Artificial Sequence
<220> FEATURE:
<223> OTHER INFORMATION: MFP[Mgfp5]4-EBPPI[G1A4F1]6-MFP[Mgfp5]4

<400> SEQUENCE: 91

tctagtgaag aatataaagg tggttattac cccggcaaca cctatcatta tcatagtggg     60

ggcagttatc acggcagcgg ctaccatggc ggctataaag gtaaatacta cggtaaagcg    120

aaaaaatact attataaata caaaaacagc ggcaaatata agtacctgaa aaaagctcgt    180

aaataccatc gtaaaggcta taaaaaatat tacggcggcg gcagttcgtc tagtgaagaa    240

tataaaggtg gttattaccc cggcaacacc tatcattatc atagtggggg cagttatcac    300

ggcagcggct accatggcgg ctataaaggt aaatactacg gtaaagcgaa aaaatactat    360

tataaataca aaaacagcgg caaatataag tacctgaaaa aagctcgtaa ataccatcgt    420

aaaggctata aaaaatatta cggcggcggc agttcgtcta gtgaagaata taaaggtggt    480

tattaccccg gcaacaccta tcattatcat agtgggggca gttatcacgg cagcggctac    540

catggcggct ataaaggtaa atactacggt aaagcgaaaa aatactatta taaatacaaa    600

aacagcggca aatataagta cctgaaaaaa gctcgtaaat accatcgtaa aggctataaa    660

aaatattacg gcggcggcag ttcgtctagt gaagaatata aaggtggtta ttaccccggc    720

aacacctatc attatcatag tgggggcagt tatcacggca gcggctacca tggcggctat    780

aaaggtaaat actacggtaa agcgaaaaaa tactattata aatacaaaaa cagcggcaaa    840

tataagtacc tgaaaaaagc tcgtaaatac catcgtaaag gctataaaaa atattacggc    900

ggcggcagtt cgattcctgc agccggtatc ccggccggtg gcattccggc agccggcatt    960

ccggccgccg gcatcccggc atttggcatt cctgcagcag gcattcctgc agccggtatc   1020

ccggccggtg gcattccggc agccggcatt ccggccgccg gcatcccggc atttggcatt   1080

cctgcagcag gcattcctgc agccggtatc ccggccggtg gcattccggc agccggcatt   1140

ccggccgccg gcatcccggc atttggcatt cctgcagcag gcattcctgc agccggtatc   1200

ccggccggtg gcattccggc agccggcatt ccggccgccg gcatcccggc atttggcatt   1260

cctgcagcag gcattcctgc agccggtatc ccggccggtg gcattccggc agccggcatt   1320

ccggccgccg gcatcccggc atttggcatt cctgcagcag gcattcctgc agccggtatc   1380

ccggccggtg gcattccggc agccggcatt ccggccgccg gcatcccggc atttggcatt   1440

cctgcagcag gctctagtga agaatataaa ggtggttatt accccggcaa cacctatcat   1500

tatcatagtg ggggcagtta tcacggcagc ggctaccatg gcggctataa aggtaaatac   1560

tacggtaaag cgaaaaaata ctattataaa tacaaaaaca gcggcaaata taagtacctg   1620

aaaaaagctc gtaaatacca tcgtaaaggc tataaaaaat attacggcgg cggcagttcg   1680

tctagtgaag aatataaagg tggttattac cccggcaaca cctatcatta tcatagtggg   1740

ggcagttatc acggcagcgg ctaccatggc ggctataaag gtaaatacta cggtaaagcg   1800

aaaaaatact attataaata caaaaacagc ggcaaatata agtacctgaa aaaagctcgt   1860

aaataccatc gtaaaggcta taaaaaatat tacggcggcg gcagttcgtc tagtgaagaa   1920

tataaaggtg gttattaccc cggcaacacc tatcattatc atagtggggg cagttatcac   1980
```

```
ggcagcggct accatggcgg ctataaaggt aaatactacg gtaaagcgaa aaaatactat   2040

tataaataca aaaacagcgg caaatataag tacctgaaaa aagctcgtaa ataccatcgt   2100

aaaggctata aaaaatatta cggcggcggc agttcgtcta gtgaagaata taaaggtggt   2160

tattaccccg gcaacaccta tcattatcat agtgggggca gttatcacgg cagcggctac   2220

catggcggct ataaaggtaa atactacggt aaagcgaaaa aatactatta taaatacaaa   2280

aacagcggca aatataagta cctgaaaaaa gctcgtaaat accatcgtaa aggctataaa   2340

aaatattacg gcggcggcag ttcg                                          2364
```